(12) United States Patent
Choi et al.

(10) Patent No.: US 12,234,219 B2
(45) Date of Patent: Feb. 25, 2025

(54) ORGANIC ELECTROLUMINESCENT COMPOUND, A PLURALITY OF HOST MATERIALS, AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Eun-Joung Choi, Gyeonggi-do (KR);
Hyun-Ju Kang, Gyeonggi-do (KR);
Hong-Yeop Na, Gyeonggi-do (KR);
Su-Hyun Lee, Gyeonggi-do (KR);
Sang-Hee Cho, Gyeonggi-do (KR)

(73) Assignee: Rohm and Haas Electronic Materials Korea Ltd. (KR)

( * ) Notice: Subject to any disclaimer, the term of this patent is extended or adjusted under 35 U.S.C. 154(b) by 835 days.

(21) Appl. No.: 17/391,160

(22) Filed: Aug. 2, 2021

(65) Prior Publication Data
US 2022/0048886 A1    Feb. 17, 2022

(30) Foreign Application Priority Data
Aug. 14, 2020 (KR) .................. 10-2020-0102481

(51) Int. Cl.
| | | |
|---|---|---|
| *C07D 401/10* | (2006.01) |
| *H10K 50/11* | (2023.01) |
| *H10K 85/60* | (2023.01) |
| *H10K 101/00* | (2023.01) |
| *H10K 101/40* | (2023.01) |

(52) U.S. Cl.
CPC ......... *C07D 401/10* (2013.01); *H10K 85/622* (2023.02); *H10K 85/623* (2023.02); *H10K 85/624* (2023.02); *H10K 85/626* (2023.02); *H10K 85/633* (2023.02); *H10K 85/636* (2023.02); *H10K 85/6572* (2023.02); *H10K 85/6574* (2023.02); *H10K 85/6576* (2023.02); *H10K 50/11* (2023.02); *H10K 2101/40* (2023.02); *H10K 2101/90* (2023.02)

(58) Field of Classification Search
CPC .. C07D 401/10; H10K 85/624; H10K 85/636; H10K 85/633; H10K 85/6574; H10K 85/623; H10K 85/622; H10K 85/6576; H10K 85/626; H10K 85/6572; H10K 2101/90; H10K 2101/40; C07F 9/587; C07F 15/06; C09K 2211/1029; C09K 2211/1044; C09K 2211/187
See application file for complete search history.

(56) References Cited

U.S. PATENT DOCUMENTS

| | | |
|---|---|---|
| 2011/0097305 A1 | 4/2011 | Connors et al. |
| 2015/0144924 A1 | 5/2015 | Shin et al. |
| 2018/0208837 A1 | 7/2018 | Ahn |
| 2019/0123287 A1* | 4/2019 | Fuchiwaki ......... H10K 85/6572 |
| 2020/0028089 A1 | 1/2020 | Cho et al. |

FOREIGN PATENT DOCUMENTS

| | | |
|---|---|---|
| CN | 109748916 A | 5/2019 |
| KR | 20160026661 A | 3/2016 |
| KR | 20170003472 A | 1/2017 |
| KR | 20170123053 A | 11/2017 |
| WO | 2014104600 A1 | 7/2014 |

OTHER PUBLICATIONS

Search Report from China National Intellectual Property Administration for China Patent application No. 202110867909.7; Application Date: Jul. 29, 2021.

* cited by examiner

*Primary Examiner* — Shane Fang
(74) *Attorney, Agent, or Firm* — G. Creston Campbell

(57) ABSTRACT

An organic electroluminescent compound and a plurality of host materials produce an organic electroluminescent device having an improved luminous efficiency.

9 Claims, No Drawings

ORGANIC ELECTROLUMINESCENT COMPOUND, A PLURALITY OF HOST MATERIALS, AND ORGANIC ELECTROLUMINESCENT DEVICE COMPRISING THE SAME

TECHNICAL FIELD

The present disclosure relates to an organic electroluminescent compound, a plurality of host materials, and an organic electroluminescent device comprising the same.

BACKGROUND ART

A small molecular organic electroluminescent device (OLED) was first developed by Tang, et al., of Eastman Kodak in 1987 by using TPD/ALq3 bi-layer consisting of a light-emitting layer and a charge transport layer. Thereafter, the development of OLEDs was rapidly effected and OLEDs have been commercialized. At present, OLEDs primarily use phosphorescent materials having excellent luminous efficiency in panel implementation. An OLED having a high luminous efficiency property is required for long time use and high resolution of a display.

Meanwhile, Korean Patent Application Laying-Open No. 2015-0061976 discloses an indenopyrimidine derivative compound. However, the specific compounds disclosed in the aforementioned reference show device properties of a similar level to a small molecule of 4,4'-N,N'-dicarbazole-biphenyl (CBP). Thus, it is required to develop a light-emitting material having improved performances, for example, improved driving voltage, luminous efficiency, and/or power efficiency properties, as compared with the specific compounds disclosed in the aforementioned reference.

DISCLOSURE OF INVENTION

Technical Problem

The objective of the present disclosure is to provide an organic electroluminescent compound having a new structure suitable for applying it to an organic electroluminescent device. Another objective of the present disclosure is to provide an improved organic electroluminescent material capable of providing an organic electroluminescent device having an improved luminous efficiency property. Still another objective of the present disclosure is to provide an organic electroluminescent device having improved driving voltage and/or luminous efficiency properties by comprising a specific combination of compounds as host materials.

Solution to Problem

The present inventors found that the above objective can be achieved by a compound represented by the following formula 1. The compound represented by the following formula 1 can be applied to an organic electroluminescent device as a single host material, or in combination with a compound represented by the following formula 11 as a plurality of host materials.

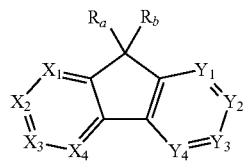

In formula 1,
$R_a$ and $R_b$, each independently, represent a substituted or unsubstituted (C1-C30)alkyl, a substituted or unsubstituted (C6-C30)aryl, or a substituted or unsubstituted (3- to 30-membered)heteroaryl; or $R_a$ and $R_b$ may be linked to each other to form a ring(s);
$X_1$ to $X_4$, each independently, represent N or $CR_c$, and at least two of $X_1$ to $X_4$ represent N;
$Y_1$ to $Y_4$, each independently, represent N or $CR_d$, and at least one of $Y_1$ to $Y_4$ represents N;
$R_c$ and $R_d$, each independently, are represented by -L-Ar;
L represents a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene;
Ar represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, or a substituted or unsubstituted (C1-C30)alkoxy; or is represented by the following formula 3 or 4:

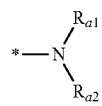

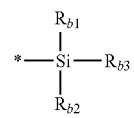

in formulas 3 and 4,
$R_{a1}$, $R_{a2}$, $R_{b1}$, $R_{b2}$, and $R_{b3}$, each independently, represent a substituted or unsubstituted (C6-C30)aryl, a substituted or unsubstituted (3- to 30-membered)heteroaryl, or a substituted or unsubstituted (C3-C30)cycloalkyl, and
* represents a site linked to L; or
at least two adjacent Ar's may be linked to each other to form a ring(s).

Advantageous Effects of Invention

The organic electroluminescent compound according to the present disclosure exhibits performances suitable for using it in an organic electroluminescent device. In addition, an organic electroluminescent device having improved luminous efficiency and/or lifetime properties compared to conventional organic electroluminescent devices is provided by comprising the compound according to the present disclosure as a single host material, or by comprising a specific combination of compounds according to the present disclosure as a plurality of host materials.

MODE FOR THE INVENTION

Hereinafter, the present disclosure will be described in detail. However, the following description is intended to explain the present disclosure and is not meant in any way to restrict the scope of the present disclosure.

The term "organic electroluminescent compound" in the present disclosure means a compound that may be used in an organic electroluminescent device, and may be comprised in any layer constituting an organic electroluminescent device, as necessary.

The term "an organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material (including a host material and a dopant material), an electron buffer material, a hole blocking material, an electron transport material, an electron injection material, etc.

The term "a plurality of organic electroluminescent materials" in the present disclosure means an organic electroluminescent material comprising a combination of at least two compounds, which may be comprised in any organic layer constituting an organic electroluminescent device. It may mean both a material before being comprised in an organic electroluminescent device (for example, before vapor deposition) and a material after being comprised in an organic electroluminescent device (for example, after vapor deposition). For example, a plurality of organic electroluminescent materials of the present disclosure may be a combination of at least two compounds, which may be comprised in at least one layer of a hole injection layer, a hole transport layer, a hole auxiliary layer, a light-emitting auxiliary layer, an electron blocking layer, a light-emitting layer, an electron buffer layer, a hole blocking layer, an electron transport layer, and an electron injection layer. The at least two compounds may be comprised in the same layer or different layers by means of the methods used in the art, and may be mixture-evaporated or co-evaporated, or may be individually evaporated.

The term "a plurality of host materials" in the present disclosure means a host material comprising a combination of at least two compounds, which may be comprised in any light-emitting layer constituting an organic electroluminescent device. It may mean both a material before being comprised in an organic electroluminescent device (for example, before vapor deposition) and a material after being comprised in an organic electroluminescent device (for example, after vapor deposition). For example, the plurality of host materials of the present disclosure is a combination of at least two host materials, and may selectively further comprise conventional materials comprised in an organic electroluminescent material. At least two compounds comprised in the plurality of host materials of the present disclosure may be comprised together in one light-emitting layer or may respectively be comprised in different light-emitting layers. For example, the at least two host materials may be mixture-evaporated or co-evaporated, or may be individually evaporated.

The organic electroluminescent material of the present disclosure may comprise at least one compound represented by formula 1. The compound represented by formula 1 may be comprised in a light-emitting layer, but is not limited thereto. When comprised in a light-emitting layer, the compound represented by formula 1 may be comprised as a host material. In addition, the compound represented by formula 1 may be comprised in an electron transport zone. Further, the compound represented by formula 1 may be comprised in an electron buffer layer, but is not limited thereto.

Herein, the term "(C1-C30)alkyl(ene)" is meant to be a linear or branched alkyl(ene) having 1 to 30 carbon atoms constituting the chain, in which the number of carbon atoms is preferably 1 to 10, and more preferably 1 to 6. The above alkyl may include methyl, ethyl, n-propyl, isopropyl, n-butyl, isobutyl, tert-butyl, sec-butyl, etc. The term "(C3-C30)cycloalkyl" is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, cyclopentylmethyl, cyclohexylmethyl, etc. The term "(3- to 7-membered)heterocycloalkyl" is meant to be a cycloalkyl having 3 to 7 ring backbone atoms, and including at least one heteroatom selected from the group consisting of B, N, O, S, Si, and P, and preferably the group consisting of O, S, and N. The above heterocycloalkyl may include tetrahydrofuran, pyrrolidine, thiolan, tetrahydropyran, etc. The term "(C6-C30)aryl(ene)" is meant to be a monocyclic or fused ring radical derived from an aromatic hydrocarbon having 6 to 30 ring backbone carbon atoms. The above aryl(ene) may be partially saturated, and may comprise a spiro structure. The above aryl may include phenyl, biphenyl, terphenyl, naphthyl, binaphthyl, phenylnaphthyl, naphthylphenyl, fluorenyl, phenylfluorenyl, diphenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, spiro[fluorene-benzofluoren]yl, azulenyl, tetramethyldihydrophenanthrenyl, etc. Specifically, the above aryl may include phenyl, 1-naphthyl, 2-naphthyl, 1-anthryl, 2-anthryl, 9-anthryl, benzanthryl, 1-phenanthryl, 2-phenanthryl, 3-phenanthryl, 4-phenanthryl, 9-phenanthryl, naphthacenyl, pyrenyl, 1-chrysenyl, 2-chrysenyl, 3-chrysenyl, 4-chrysenyl, 5-chrysenyl, 6-chrysenyl, benzo[c]phenanthryl, benzo[g]chrysenyl, 1-triphenylenyl, 2-triphenylenyl, 3-triphenylenyl, 4-triphenylenyl, 1-fluorenyl, 2-fluorenyl, 3-fluorenyl, 4-fluorenyl, 9-fluorenyl, benzo[a]fluorenyl, benzo[b]fluorenyl, benzo[c]fluorenyl, dibenzofluorenyl, 2-biphenyl, 3-biphenyl, 4-biphenyl, o-terphenyl, m-terphenyl-4-yl, m-terphenyl-3-yl, m-terphenyl-2-yl, p-terphenyl-4-yl, p-terphenyl-3-yl, p-terphenyl-2-yl, m-quaterphenyl, 3-fluoranthenyl, 4-fluoranthenyl, 8-fluoranthenyl, 9-fluoranthenyl, benzofluoranthenyl, o-tolyl, m-tolyl, p-tolyl, 2,3-xylyl, 3,4-xylyl, 2,5-xylyl, mesityl, o-cumenyl, m-cumenyl, p-cumenyl, p-tert-butylphenyl, p-(2-phenylpropyl)phenyl, 4'-methylbiphenyl, 4"-tert-butyl-p-terphenyl-4-yl, 9,9-dimethyl-1-fluorenyl, 9,9-dimethyl-2-fluorenyl, 9,9-dimethyl-3-fluorenyl, 9,9-dimethyl-4-fluorenyl, 9,9-diphenyl-1-fluorenyl, 9,9-diphenyl-2-fluorenyl, 9,9-diphenyl-3-fluorenyl, 9,9-diphenyl-4-fluorenyl, 11,11-dimethyl-1-benzo[a]fluorenyl, 11,11-dimethyl-2-benzo[a]fluorenyl, 11,11-dimethyl-3-benzo[a]fluorenyl, 11,11-dimethyl-4-benzo[a]fluorenyl, 11,11-dimethyl-5-benzo[a]fluorenyl, 11,11-dimethyl-6-benzo[a]fluorenyl, 11,11-dimethyl-7-benzo[a]fluorenyl, 11,11-dimethyl-8-benzo[a]fluorenyl, 11,11-dimethyl-9-benzo[a]fluorenyl, 11,11-dimethyl-10-benzo[a]

fluorenyl, 11,11-dimethyl-1-benzo[b]fluorenyl, 11,11-dimethyl-2-benzo[b]fluorenyl, 11,11-dimethyl-3-benzo[b]fluorenyl, 11,11-dimethyl-4-benzo[b]fluorenyl, 11,11-dimethyl-5-benzo[b]fluorenyl, 11,11-dimethyl-6-benzo[b]fluorenyl, 11,11-dimethyl-7-benzo[b]fluorenyl, 11,11-dimethyl-8-benzo[b]fluorenyl, 11,11-dimethyl-9-benzo[b]fluorenyl, 11,11-dimethyl-10-benzo[b]fluorenyl, 11,11-dimethyl-1-benzo[c]fluorenyl, 11,11-dimethyl-2-benzo[c]fluorenyl, 11,11-dimethyl-3-benzo[c]fluorenyl, 11,11-dimethyl-4-benzo[c]fluorenyl, 11,11-dimethyl-5-benzo[c]fluorenyl, 11,11-dimethyl-6-benzo[c]fluorenyl, 11,11-dimethyl-7-benzo[c]fluorenyl, 11,11-dimethyl-8-benzo[c]fluorenyl, 11,11-dimethyl-9-benzo[c]fluorenyl, 11,11-dimethyl-10-benzo[c]fluorenyl, 11,11-diphenyl-1-benzo[a]fluorenyl, 11,11-diphenyl-2-benzo[a]fluorenyl, 11,11-diphenyl-3-benzo[a]fluorenyl, 11,11-diphenyl-4-benzo[a]fluorenyl, 11,11-diphenyl-5-benzo[a]fluorenyl, 11,11-diphenyl-6-benzo[a]fluorenyl, 11,11-diphenyl-7-benzo[a]fluorenyl, 11,11-diphenyl-8-benzo[a]fluorenyl, 11,11-diphenyl-9-benzo[a]fluorenyl, 11,11-diphenyl-10-benzo[a]fluorenyl, 11,11-diphenyl-1-benzo[b]fluorenyl, 11,11-diphenyl-2-benzo[b]fluorenyl, 11,11-diphenyl-3-benzo[b]fluorenyl, 11,11-diphenyl-4-benzo[b]fluorenyl, 11,11-diphenyl-5-benzo[b]fluorenyl, 11,11-diphenyl-6-benzo[b]fluorenyl, 11,11-diphenyl-7-benzo[b]fluorenyl, 11,11-diphenyl-8-benzo[b]fluorenyl, 11,11-diphenyl-9-benzo[b]fluorenyl, 11,11-diphenyl-10-benzo[b]fluorenyl, 11,11-diphenyl-1-benzo[c]fluorenyl, 11,11-diphenyl-2-benzo[c]fluorenyl, 11,11-diphenyl-3-benzo[c]fluorenyl, 11,11-diphenyl-4-benzo[c]fluorenyl, 11,11-diphenyl-5-benzo[c]fluorenyl, 11,11-diphenyl-6-benzo[c]fluorenyl, 11,11-diphenyl-7-benzo[c]fluorenyl, 11,11-diphenyl-8-benzo[c]fluorenyl, 11,11-diphenyl-9-benzo[c]fluorenyl, 11,11-diphenyl-10-benzo[c]fluorenyl, 9,9,10,10-tetramethyl-9,10-dihydro-1-phenanthrenyl, 9,9,10,10-tetramethyl-9,10-dihydro-2-phenanthrenyl, 9,9,10,10-tetramethyl-9,10-dihydro-3-phenanthrenyl, 9,9,10,10-tetramethyl-9,10-dihydro-4-phenanthrenyl, etc.

The term "(3- to 30-membered)heteroaryl(ene)" is meant to be an aryl or an arylene having 3 to 30 ring backbone atoms, and including at least one, preferably 1 to 4 heteroatoms selected from the group consisting of B, N, O, S, Si, and P. The above heteroaryl(ene) may be a monocyclic ring, or a fused ring condensed with at least one benzene ring; may be partially saturated; may be one formed by linking at least one heteroaryl or aryl group to a heteroaryl group via a single bond(s); and may comprise a spiro structure. The above heteroaryl may include a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, and pyridazinyl, and a fused ring-type heteroaryl such as benzofuranyl, benzothiophenyl, isobenzofuranyl, dibenzofuranyl, dibenzothiophenyl, dibenzoselenophenyl, naphthobenzofuranyl, naphthobenzothiophenyl, benzofuroquinolinyl, benzofuroquinazolinyl, benzofuronaphthyridinyl, benzofuropyrimidinyl, naphthofuropyrimidinyl, benzothienoquinolinyl, benzothienoquinazolinyl, benzothienonaphthyridinyl, benzothienopyrimidinyl, naphthothienopyrimidinyl, pyrimidoindolyl, benzopyrimidoindolyl, benzofuropyrazinyl, naphthofuropyrazinyl, benzothienopyrazinyl, naphthothienopyrazinyl, pyrazinoindolyl, benzopyrazinoindolyl, benzimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, benzocarbazolyl, dibenzocarbazolyl, phenoxazinyl, phenanthridinyl, benzodioxolyl, dihydroacridinyl, benzotriazolphenazinyl, imidazopyridyl, chromenoquinazolinyl, thiochromenoquinazolinyl, dimethylbenzoperimidinyl, indolocarbazolyl, indenocarbazolyl, etc. More specifically, the above heteroaryl may include 1-pyrrolyl, 2-pyrrolyl, 3-pyrrolyl, pyrazinyl, 2-pyridyl, 2-pyrimidinyl, 4-pyrimidinyl, 5-pyrimidinyl, 6-pyrimidinyl, 1,2,3-triazin-4-yl, 1,2,4-triazin-3-yl, 1,3,5-triazin-2-yl, 1-imidazolyl, 2-imidazolyl, 1-pyrazolyl, 1-indolidinyl, 2-indolidinyl, 3-indolidinyl, 5-indolidinyl, 6-indolidinyl, 7-indolidinyl, 8-indolidinyl, 2-imidazopyridyl, 3-imidazopyridyl, 5-imidazopyridyl, 6-imidazopyridyl, 7-imidazopyridyl, 8-imidazopyridyl, 3-pyridyl, 4-pyridyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 3-quinoxalinyl, 5-quinoxalinyl, 6-quinoxalinyl, 1-carbazolyl, 2-carbazolyl, 3-carbazolyl, 4-carbazolyl, 9-carbazolyl, azacarbazolyl-1-yl, azacarbazolyl-2-yl, azacarbazolyl-3-yl, azacarbazolyl-4-yl, azacarbazolyl-5-yl, azacarbazolyl-6-yl, azacarbazolyl-7-yl, azacarbazolyl-8-yl, azacarbazolyl-9-yl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-tert-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-tert-butyl-1-indolyl, 4-tert-butyl-1-indolyl, 2-tert-butyl-3-indolyl, 4-tert-butyl-3-indolyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-naphtho-[1,2-b]-benzofuranyl, 2-naphtho-[1,2-b]-benzofuranyl, 3-naphtho-[1,2-b]-benzofuranyl, 4-naphtho-[1,2-b]-benzofuranyl, 5-naphtho-[1,2-b]-benzofuranyl, 6-naphtho-[1,2-b]-benzofuranyl, 7-naphtho-[1,2-b]-benzofuranyl, 8-naphtho-[1,2-b]-benzofuranyl, 9-naphtho-[1,2-b]-benzofuranyl, 10-naphtho-[1,2-b]-benzofuranyl, 1-naphtho-[2,3-b]-benzofuranyl, 2-naphtho-[2,3-b]-benzofuranyl, 3-naphtho-[2,3-b]-benzofuranyl, 4-naphtho-[2,3-b]-benzofuranyl, 5-naphtho-[2,3-b]-benzofuranyl, 6-naphtho-[2,3-b]-benzofuranyl, 7-naphtho-[2,3-b]-benzofuranyl, 8-naphtho-[2,3-b]-benzofuranyl, 9-naphtho-[2,3-b]-benzofuranyl, 10-naphtho-[2,3-b]-benzofuranyl, 1-naphtho-[2,1-b]-benzofuranyl, 2-naphtho-[2,1-b]-benzofuranyl, 3-naphtho-[2,1-b]-benzofuranyl, 4-naphtho-[2,1-b]-benzofuranyl, 5-naphtho-[2,1-b]-benzofuranyl, 6-naphtho-[2,1-b]-benzofuranyl, 7-naphtho-[2,1-b]-benzofuranyl, 8-naphtho-[2,1-b]-benzofuranyl, 9-naphtho-[2,1-b]-benzofuranyl, 10-naphtho-[2,1-b]-benzofuranyl, 1-naphtho-[1,2-b]-benzothiophenyl, 2-naphtho-[1,2-b]-benzothiophenyl, 3-naphtho-[1,2-b]-benzothiophenyl, 4-naphtho-[1,2-b]-benzothiophenyl, 5-naphtho-[1,2-b]-benzothiophenyl, 6-naphtho-[1,2-b]-benzothiophenyl, 7-naphtho-[1,2-b]-benzothiophenyl, 8-naphtho-[1,2-b]-benzothiophenyl, 9-naphtho-[1,2-b]-benzothiophenyl, 10-naphtho-

[1,2-b]-benzothiophenyl, 1-naphtho-[2,3-b]-benzothiophenyl, 2-naphtho-[2,3-b]-benzothiophenyl, 3-naphtho-[2,3-b]-benzothiophenyl, 4-naphtho-[2,3-b]-benzothiophenyl, 5-naphtho-[2,3-b]-benzothiophenyl, 1-naphtho-[2,1-b]-benzothiophenyl, 2-naphtho-[2,1-b]-benzothiophenyl, 3-naphtho-[2,1-b]-benzothiophenyl, 4-naphtho-[2,1-b]-benzothiophenyl, 5-naphtho-[2,1-b]-benzothiophenyl, 6-naphtho-[2,1-b]-benzothiophenyl, 7-naphtho-[2,1-b]-benzothiophenyl, 8-naphtho-[2,1-b]-benzothiophenyl, 9-naphtho-[2,1-b]-benzothiophenyl, 10-naphtho-[2,1-b]-benzothiophenyl, 2-benzofuro[3,2-d]pyrimidinyl, 6-benzofuro[3,2-d]pyrimidinyl, 7-benzofuro[3,2-d]pyrimidinyl, 8-benzofuro[3,2-d]pyrimidinyl, 9-benzofuro[3,2-d]pyrimidinyl, 2-benzothio[3,2-d]pyrimidinyl, 6-benzothio[3,2-d]pyrimidinyl, 7-benzothio[3,2-d]pyrimidinyl, 8-benzothio[3,2-d]pyrimidinyl, 9-benzothio[3,2-d]pyrimidinyl, 2-benzofuro[3,2-d]pyrazinyl, 6-benzofuro[3,2-d]pyrazinyl, 7-benzofuro[3,2-d]pyrazinyl, 8-benzofuro[3,2-d]pyrazinyl, 9-benzofuro[3,2-d]pyrazinyl, 2-benzothio[3,2-d]pyrazinyl, 6-benzothio[3,2-d]pyrazinyl, 7-benzothio[3,2-d]pyrazinyl, 8-benzothio[3,2-d]pyrazinyl, 9-benzothio[3,2-d]pyrazinyl, 1-silafluorenyl, 2-silafluorenyl, 3-silafluorenyl, 4-silafluorenyl, 1-germafluorenyl, 2-germafluorenyl, 3-germafluorenyl, 4-germafluorenyl, 1-dibenzoselenophenyl, 2-dibenzoselenophenyl, 3-dibenzoselenophenyl, 4-dibenzoselenophenyl, etc. Furthermore, "halogen" includes F, Cl, Br, and I.

In addition, "ortho (o-)," "meta (m-)," and "para (p-)" are prefixes, which represent the relative positions of substituents respectively. Ortho indicates that two substituents are adjacent to each other, and for example, when two substituents in a benzene derivative occupy positions 1 and 2, it is called an ortho position. Meta indicates that two substituents are at positions 1 and 3, and for example, when two substituents in a benzene derivative occupy positions 1 and 3, it is called a meta position. Para indicates that two substituents are at positions 1 and 4, and for example, when two substituents in a benzene derivative occupy positions 1 and 4, it is called a para position.

Herein, "substituted" in the expression "substituted or unsubstituted" means that a hydrogen atom in a certain functional group is replaced with another atom or another functional group, i.e., a substituent, and also includes that the hydrogen atom is replaced with a group formed by a linkage of two or more substituents of the above substituents. For example, the "group formed by a linkage of two or more substituents" may be pyridine-triazine. That is, pyridine-triazine may be interpreted as a heteroaryl substituent, or as substituents in which two heteroaryl substituents are linked. Herein, the substituent(s) of the substituted alkyl(ene), the substituted aryl(ene), the substituted heteroaryl(ene), the substituted cycloalkyl(ene), the substituted alkoxy, the substituted trialkylsilyl, the substituted dialkylarylsilyl, the substituted alkyldiarylsilyl, the substituted triarylsilyl, the substituted fused ring group of an aliphatic ring(s) and an aromatic ring(s), the substituted mono- or di-alkylamino, the substituted mono- or di-alkenylamino, the substituted alkylalkenylamino, the substituted mono- or di-arylamino, the substituted alkylarylamino, the substituted mono- or di-heteroarylamino, the substituted alkylheteroarylamino, the substituted alkenylarylamino, the substituted alkenylheteroarylamino, and the substituted arylheteroarylamino, each independently, are at least one selected from the group consisting of deuterium; a halogen; a cyano; a carboxyl; a nitro; a hydroxyl; a phosphineoxide; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (5- to 30-membered)heteroaryl unsubstituted or substituted with a (C6-C30)aryl(s); a (C6-C30)aryl unsubstituted or substituted with deuterium, a (C1-C30)alkyl(s), a (C6-C30)aryl(s), and/or a (5- to 30-membered)heteroaryl(s); a tri(C1-C30)alkylsilyl; a tri(C6-C30)arylsilyl; a di(C1-C30)alkyl(C6-C30)arylsilyl; a (C1-C30)alkyldi(C6-C30)arylsilyl; a fused ring group of a (C3-C30) aliphatic ring(s) and a (C6-C30) aromatic ring(s); an amino; a mono- or di-(C1-C30)alkylamino; a mono- or di-(C2-C30)alkenylamino; a mono- or di-(C6-C30)arylamino unsubstituted or substituted with a (C1-C30)alkyl(s); a mono- or di-(3- to 30-membered)heteroarylamino; a (C1-C30)alkyl(C2-C30)alkenylamino; a (C1-C30)alkyl(C6-C30)arylamino; a (C1-C30)alkyl(3- to 30-membered)heteroarylamino; a (C2-C30)alkenyl(C6-C30)arylamino; a (C2-C30)alkenyl(3- to 30-membered)heteroarylamino; a (C6-C30)aryl(3- to 30-membered)heteroarylamino; a (C1-C30)alkylcarbonyl; a (C1-C30)alkoxycarbonyl; a (C6-C30)arylcarbonyl; a (C6-C30)arylphosphine; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl. According to one embodiment of the present disclosure, the substituent(s), each independently, are at least one selected from the group consisting of a (C1-C20)alkyl; a (C5-C25) cycloalkyl; a (5- to 25-membered)heteroaryl unsubstituted or substituted with a (C6-C25)aryl(s); a (C6-C25)aryl unsubstituted or substituted with deuterium, a (C1-C20)alkyl(s), and/or a (C6-C18)aryl(s); and an unsubstituted mono- or di-(C6-C25)arylamino. According to another embodiment of the present disclosure, the substituent(s), each independently, are at least one selected from the group consisting of a (C1-C10)alkyl; a (C5-C20)cycloalkyl; a (5- to 20-membered)heteroaryl unsubstituted or substituted with a (C6-C18)aryl(s); a (C6-C20)aryl unsubstituted or substituted with deuterium, a (C1-C10)alkyl(s), and/or a (C6-C18) aryl(s); and an unsubstituted di(C6-C18)arylamino. For example, the substituent(s) may be at least one selected from the group consisting of a methyl; a tert-butyl; a cyclohexyl; a phenyl unsubstituted or substituted with at least one selected from the group consisting of deuterium, a methyl(s), and a tert-butyl(s); a naphthyl; a anthracenyl; a fluoranthenyl; a fluorenyl substituted with a phenyl(s); a pyridyl substituted with a phenyl(s); a benzoimidazolyl substituted with a phenyl(s); a phenoxazinyl; and a diphenylamino.

Herein, a ring formed by a linkage of adjacent substituents means that at least two adjacent substituents are linked to or fused with each other to form a substituted or unsubstituted, mono- or polycyclic, (3- to 30-membered) alicyclic or aromatic ring, or the combination thereof. Preferably, the ring may be a substituted or unsubstituted, mono- or polycyclic, (3- to 26-membered) alicyclic or aromatic ring, or the combination thereof. More preferably, the ring may be a mono- or polycyclic, (5- to 25-membered) aromatic ring unsubstituted or substituted with at least one of a (C6-C18) aryl(s) and a (3- to 20-membered)heteroaryl(s). In addition, the formed ring may contain at least one heteroatom selected from B, N, O, S, Si, and P, preferably at least one heteroatom selected from N, O, and S. For example, the ring may be a benzene ring, a cyclopentane ring, an indane ring, a fluorene ring, a phenanthrene ring, an indole ring, a xanthene ring, etc.

In the present disclosure, heteroaryl, heteroarylene, and heterocycloalkyl may, each independently, contain at least one heteroatom selected from B, N, O, S, Si, and P. In addition, the heteroatom may be bonded to at least one selected from the group consisting of hydrogen, deuterium, a halogen, a cyano, a substituted or unsubstituted (C1-C30) alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C2-C30)alkenylamino, a substituted or unsubstituted mono- or di-(C6-C30)arylamino, a substituted or unsubstituted mono- or di-(3- to 30-membered)heteroarylamino, a substituted or unsubstituted (C1-C30)alkyl(C2-C30)alkenylamino, a substituted or unsubstituted (C1-C30)alkyl(C6-C30)arylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, and a substituted or unsubstituted (C6-C30)aryl(3- to 30-membered)heteroarylamino.

A plurality of host materials of the present disclosure comprise a first host material and a second host material, in which the first host material comprises the compound represented by formula 1, and the second host material comprises the compound represented by formula 11. According to one embodiment of the present disclosure, the compound represented by formula 1 and the compound represented by formula 11 are different from each other.

In formula 1, $R_a$ and $R_b$, each independently, represent a substituted or unsubstituted (C1-C30)alkyl, a substituted or unsubstituted (C6-C30)aryl, or a substituted or unsubstituted (3- to 30-membered)heteroaryl; or $R_a$ and $R_b$ may be linked to each other to form a ring(s). $R_a$ and $R_b$ may be the same as or different from each other. According to one embodiment of the present disclosure, $R_a$ and $R_b$, each independently, represent a substituted or unsubstituted (C1-C20) alkyl, a substituted or unsubstituted (C6-C25)aryl, or a substituted or unsubstituted (5- to 25-membered)heteroaryl; or $R_a$ and $R_b$ may be linked to each other to form a ring(s). According to another embodiment of the present disclosure, $R_a$ and $R_b$, each independently, represent an unsubstituted (C1-C10)alkyl, or an unsubstituted (C6-C18)aryl; or $R_a$ and $R_b$ may be linked to each other to form a ring(s). For example, $R_a$ and $R_b$, each independently, may be a methyl, an ethyl, a propyl, a phenyl, or a naphthyl; or $R_a$ and $R_b$ may be linked to each other to form a cyclopentane ring(s), an indane ring(s), or a fluorene ring(s).

In formula 1, $X_1$ to $X_4$, each independently, represent N or $CR_c$, and at least two of $X_1$ to $X_4$ represent N. According to one embodiment of the present disclosure, any two of $X_1$ to $X_4$ represent N.

In formula 1, $Y_1$ to $Y_4$, each independently, represent N or $CR_d$, and at least one of $Y_1$ to $Y_4$ represents N. According to one embodiment of the present disclosure, any one or two of $Y_1$ to $Y_4$ represent N.

$R_c$ and $R_d$, each independently, are represented by -L-Ar.

L represents a single bond, a substituted or unsubstituted (C1-C30)alkylene, a substituted or unsubstituted (C6-C30) arylene, a substituted or unsubstituted (3- to 30-membered) heteroarylene, or a substituted or unsubstituted (C3-C30) cycloalkylene.

According to one embodiment of the present disclosure, L represents a single bond, a substituted or unsubstituted (C6-C25)arylene, or a substituted or unsubstituted (5- to 25-membered)heteroarylene. According to another embodiment of the present disclosure, L represents a single bond, an unsubstituted (C6-C18)arylene, or a (5- to 20-membered) heteroarylene unsubstituted or substituted with a (C6-C18) aryl(s). For example, L may be a single bond, a phenylene, a naphthylene, a biphenylene, a pyridylene, a pyrimidinylene, a triazinylene substituted with a phenyl(s), a quinazolinylene, or a carbazolylene, etc.

Ar represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, or a substituted or unsubstituted (C1-C30)alkoxy; or is represented by the following formula 3 or 4; or at least two adjacent Ar's may be linked to each other to form a ring(s). According to one embodiment of the present disclosure, at least one of Ar's represents a substituted or unsubstituted (C6-C30)aryl, a substituted or unsubstituted (3- to 30-membered)heteroaryl, a substituted or unsubstituted (C3-C30)cycloalkyl, or a substituted or unsubstituted (C1-C30)alkoxy; or is represented by the following formula 3 or 4. According to another embodiment of the present disclosure, Ar represents hydrogen, a substituted or unsubstituted (C1-C20)alkyl, a substituted or unsubstituted (C6-C25)aryl, or a substituted or unsubstituted (5- to 25-membered)heteroaryl; or is represented by the following formula 3 or 4; or at least two adjacent Ar's may be linked to each other to form a ring(s). According to still another embodiment of the present disclosure, Ar represents hydrogen, an unsubstituted (C1-C10)alkyl, a (C6-C18)aryl unsubstituted or substituted with a (C1-C6)alkyl(s), or a (5- to 20-membered)heteroaryl unsubstituted or substituted with a (C6-C18)aryl(s); or is represented by the following formula 3 or 4; or at least two adjacent Ar's may be linked to each other to form a ring(s). For example, Ar may be hydrogen, a tert-butyl, a phenyl unsubstituted or substituted with a tert-butyl(s), a naphthyl, a biphenyl, a dimethylfluorenyl, a phenanthrenyl, an anthracenyl, a terphenyl, a pyridyl, a pyrimidinyl, a diphenyltriazinyl, a quinoxalinyl, a quinazolinyl substituted with a phenyl(s), a carbazolyl substituted with a phenyl(s), a dibenzofuranyl, or a dibenzothiophenyl, etc.; or may be represented by the following formula 3; or two adjacent Ar's may be linked to each other to form a benzene ring(s) or a phenanthrene ring(s).

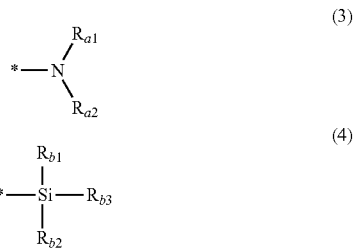

In formulas 3 and 4, $R_{a1}$, $R_{a2}$, $R_{b1}$, $R_{b2}$, and $R_{b3}$, each independently, represent a substituted or unsubstituted (C6-C30)aryl, a substituted or unsubstituted (3- to 30-membered) heteroaryl, or a substituted or unsubstituted (C3-C30)cycloalkyl. According to one embodiment of the present disclosure, $R_{a1}$, $R_{a2}$, $R_{b1}$, $R_{b2}$, and $R_{b3}$, each independently, represent a substituted or unsubstituted (C6-C25)aryl. According to another embodiment of the present disclosure, $R_{a1}$, $R_{a2}$, $R_{b1}$, $R_{b2}$, and $R_{b3}$, each independently, represent an unsubstituted (C6-C25)aryl. For example, $R_{a1}$ and $R_{a2}$, each independently, may be a phenyl, a naphthyl, or a biphenyl, etc.

In formulas 3 and 4, * represents a site linked to L.

According to one embodiment of the present disclosure, the formula 1 may be represented by at least one of the following formulas 1-1 to 1-3.

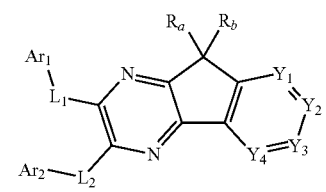
(1-1)

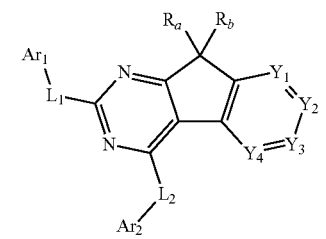
(1-2)

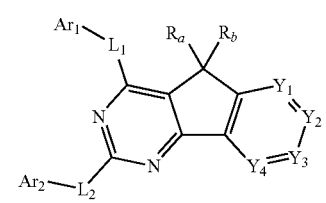
(1-3)

According to one embodiment of the present disclosure, the formula 1 may be represented by at least one of the following formulas 1-4 to 1-10. According to another embodiment of the present disclosure, the formula 1 may be represented by at least one of the following formulas 1-4 and 1-9.

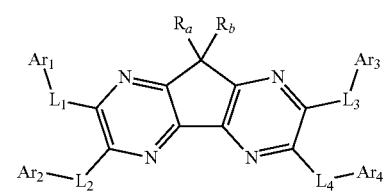
(1-4)

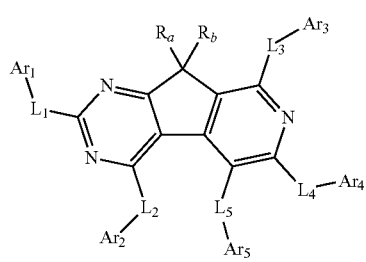
(1-5)

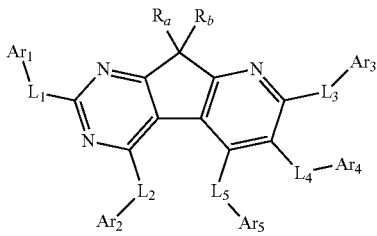
(1-6)

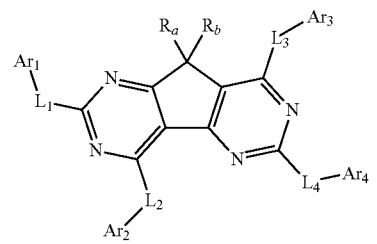
(1-7)

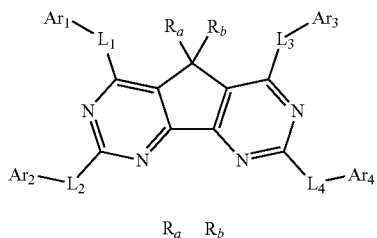
(1-8)

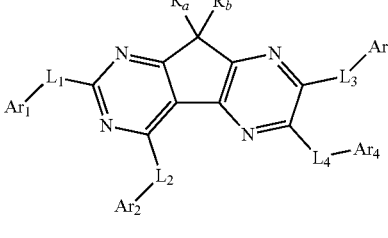
(1-9)

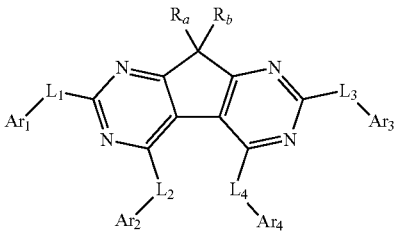
(1-10)

In formulas 1-1 to 1-10, $R_a$, $R_b$, and $Y_1$ to $Y_4$ are as defined in formula 1; $L_1$ to $L_5$, each independently, are the same as the definition of L in formula 1; and $Ar_1$ to $Ar_5$, each independently, are the same as the definition of Ar in formula 1.

In formulas 1-1 to 1-10, $Ar_1$ to $Ar_5$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, or a substituted or unsubstituted (C1-C30)alkoxy; or are each independently represented by formula 3 or 4; or $Ar_1$ and $Ar_2$ may be linked to each other to form a ring(s), $Ar_a$ and $Ar_4$ may be linked to each other to form a ring(s), or $Ar_4$ and $Ar_5$ may be linked to form a ring(s). According to one embodiment of the present disclosure, $Ar_1$ to $Ar_5$, each independently, represent hydrogen, a substituted or unsubstituted (C1-C20)alkyl, a substituted or unsubstituted (C6-C25)aryl, or a substituted or unsubstituted (5- to 25-membered)heteroaryl; or are each independently represented by formula 3 or 4; or $Ar_1$ and $Ar_2$ may be linked to each other to form a ring(s), $Ar_a$ and $Ar_4$ may be linked to each other to form a ring(s), or $Ar_4$ and $Ar_5$ may be linked to each other to form a ring(s). According to another embodiment of the present disclosure, $Ar_1$ to $Ar_5$, each independently, represent hydrogen, an unsubstituted (C1-C10)alkyl, a (C6-C18)aryl unsubstituted or substituted with a (C1-C6)alkyl(s), or a (5- to 20-membered)heteroaryl unsubstituted or substituted with a (C6-C18)aryl(s); or are each independently represented by formula 3 or 4; or $Ar_1$ and $Ar_2$ may be linked to each other to form a ring(s), $Ar_3$ and $Ar_4$ may be linked to each other to form a ring(s), or $Ar_4$ and $Ar_5$ may be linked to each other to form a ring(s). For example, $Ar_1$ to $Ar_5$, each independently, may be hydrogen, a tert-butyl, a phenyl unsubstituted or substituted with a tert-butyl(s), a naphthyl, a biphenyl, a dimethylfluorenyl, a phenanthrenyl, an anthracenyl, a terphenyl, a pyridyl, a pyrimidinyl, a diphenyltriazinyl, a quinoxalinyl, a quinazolinyl substituted with a phenyl(s), a carbazolyl substituted with a phenyl(s), a dibenzofuranyl, or a dibenzothiophenyl, etc.; or may be represented by formula 3; or $Ar_1$ and $Ar_2$ may be linked to each other to form a benzene ring(s) or a phenanthrene ring(s), $Ar_3$ and $Ar_4$ may be linked to each other to form a benzene ring(s) or a phenanthrene ring(s), or $Ar_4$ and $Ar_5$ may be linked to each other to form a benzene ring(s) or a phenanthrene ring(s).

According to one embodiment of the present disclosure, the formula 1 may be represented by at least one of the following formulas 2-1 to 2-4.

(2-1)

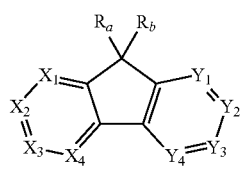

(2-2)

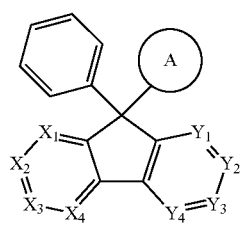

(2-3)

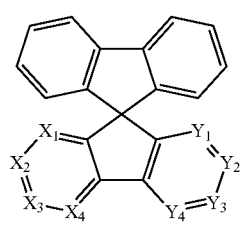

(2-4)

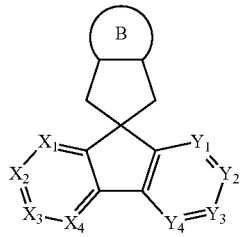

In formulas 2-1 to 2-4, $X_1$ to $X_4$ and $Y_1$ to $Y_4$ are as defined in formula 1; $R_a$ represents a methyl, an ethyl, an n-propyl, an isopropyl, an n-butyl, an isobutyl, or a tert-butyl, and $R_b$ represents a methyl, an ethyl, an n-propyl, an isopropyl, an n-butyl, an isobutyl, a tert-butyl, or a phenyl. According to one embodiment of the present disclosure, $R_a$ represents a methyl, an ethyl, or an n-propyl, and $R_b$ represents a methyl, an ethyl, an n-propyl, or a phenyl.

In formula 2-2, ring A represents a benzene or a naphthalene.

In formula 2-4, ring B is absent, or represents a benzene.

The compound represented by formula 1 may be at least one selected from the following compounds, but is not limited thereto.

C-1

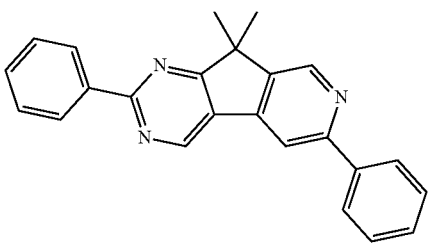

C-2

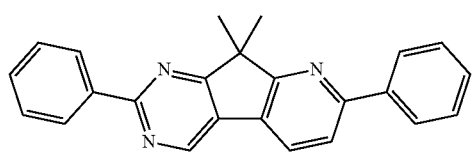

C-3

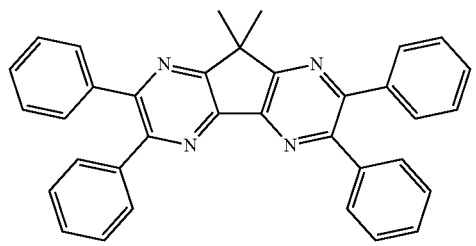

C-4

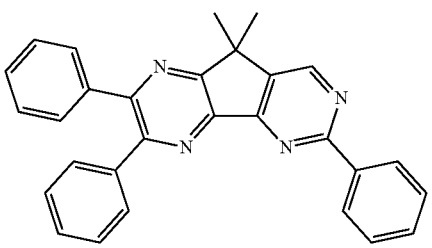

-continued

C-5

C-6

C-7

C-8

C-9

C-10

C-11

C-12

C-13

C-14

C-15
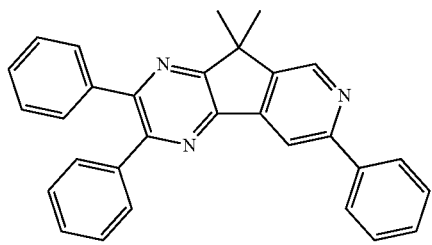
C-21
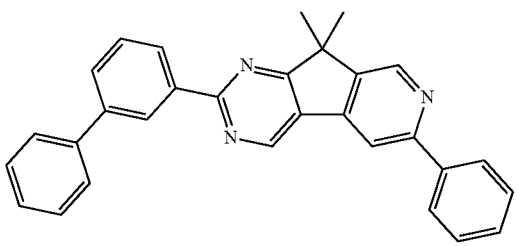
C-16
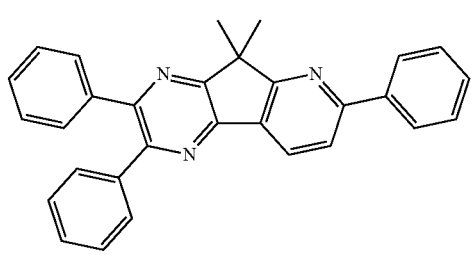
C-22
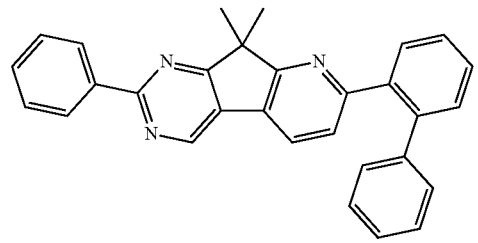
C-17
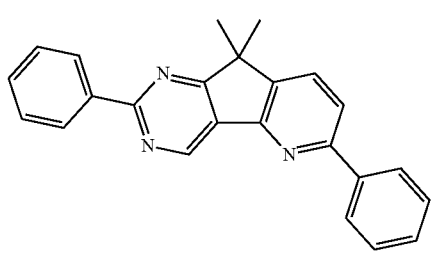
C-23
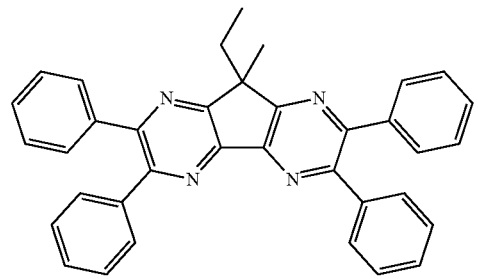
C-18
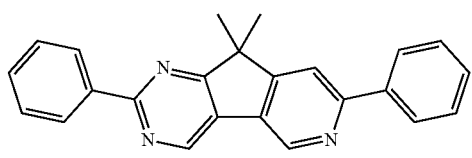
C-24
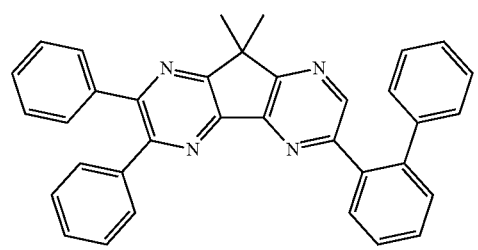
C-19
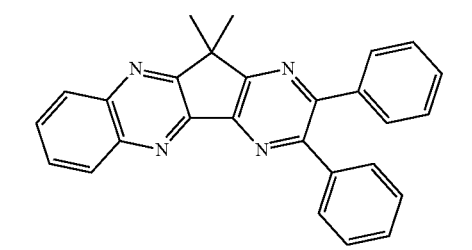
C-25
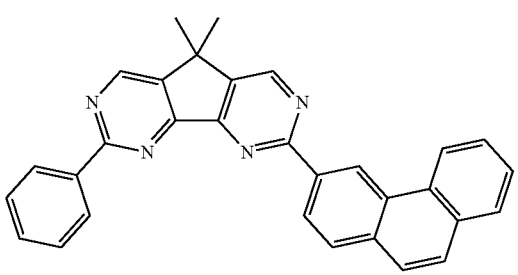
C-20
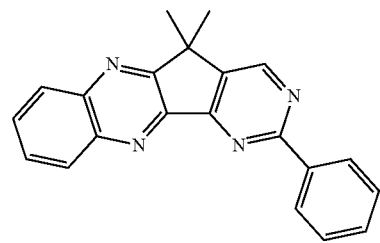
C-26
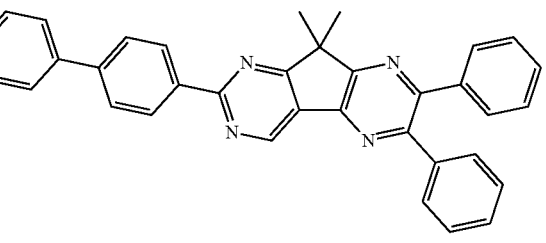

C-27
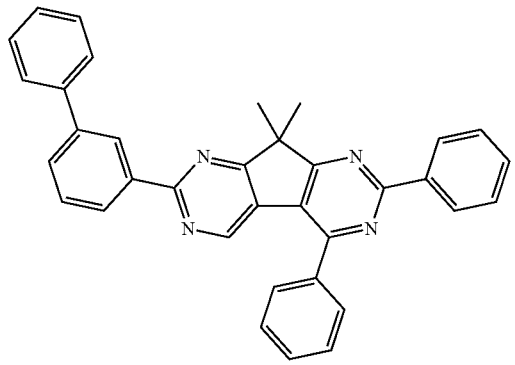
C-28
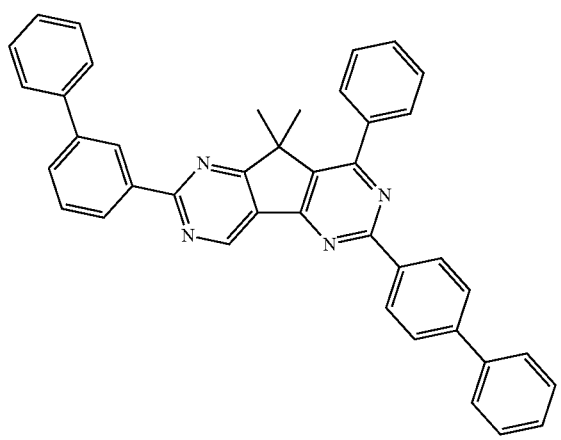
C-29
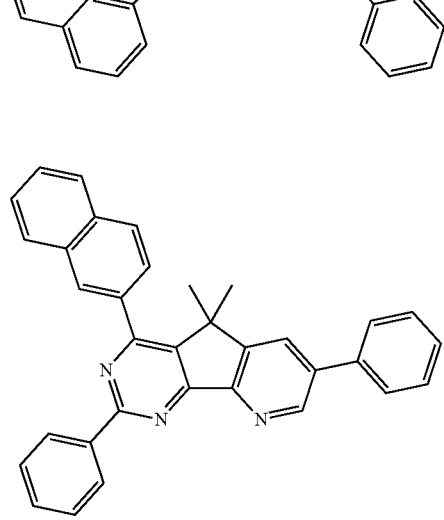
C-30
C-31
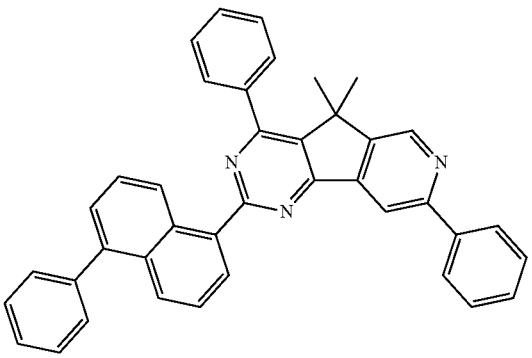
C-32
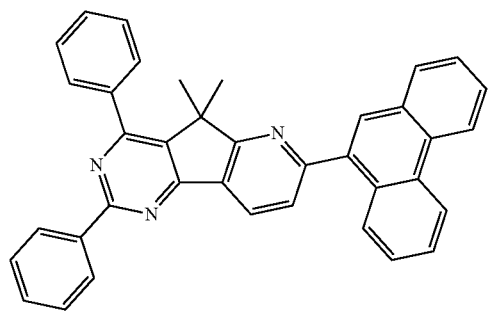
C-33
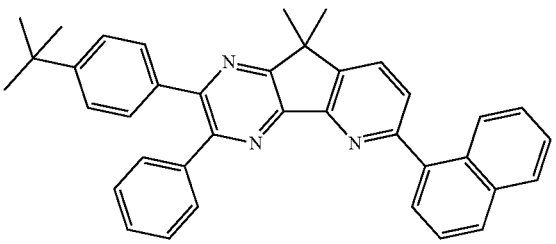
C-34
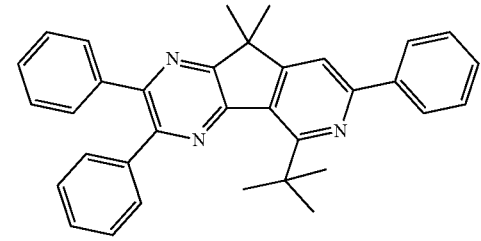
C-35
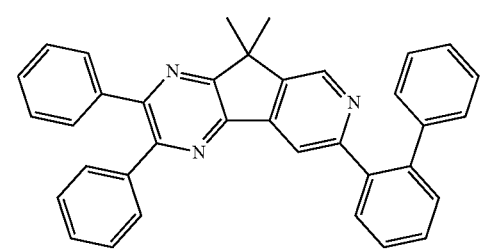

C-36
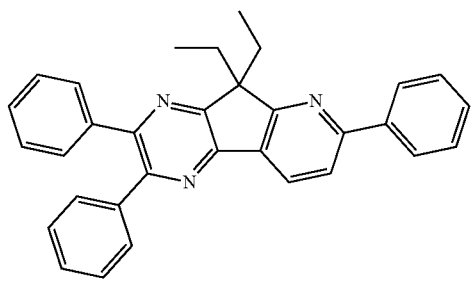
C-37
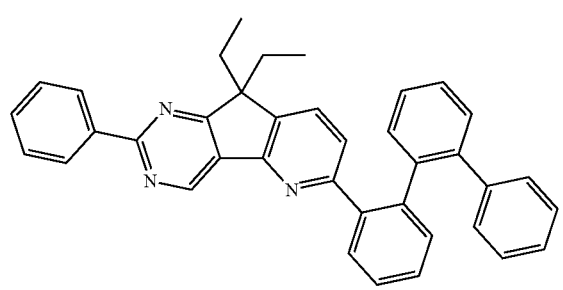
C-38
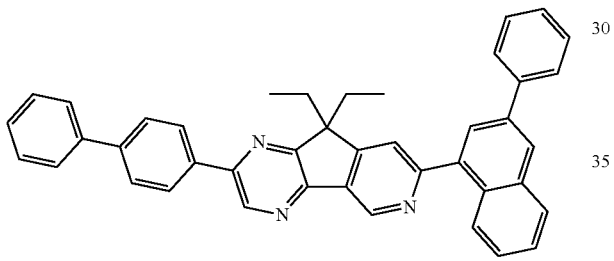
C-39
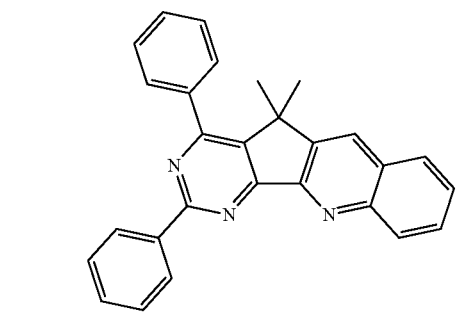
C-40
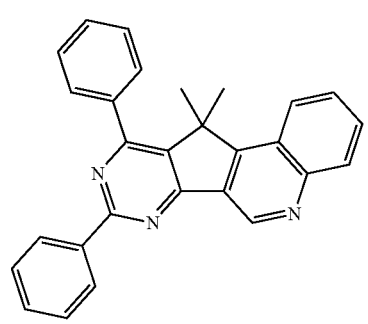
C-41
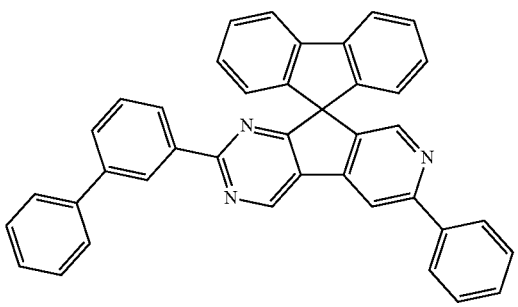
C-42
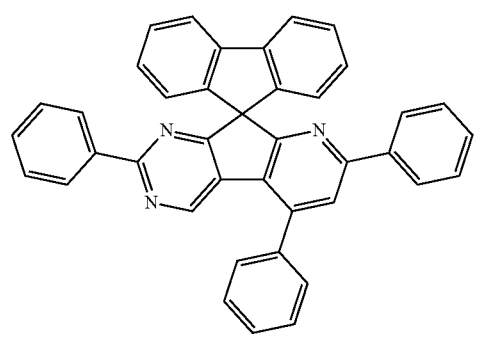
C-43
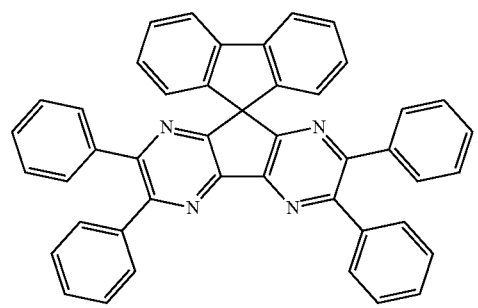
C-44
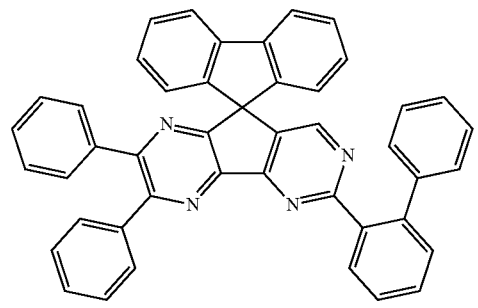
C-45
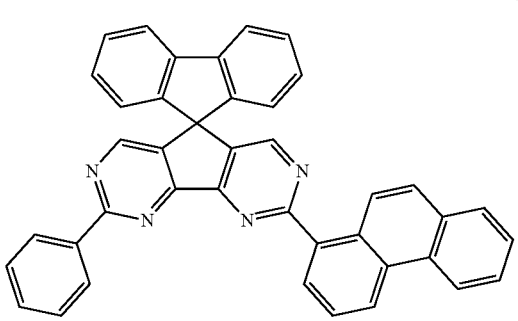

-continued
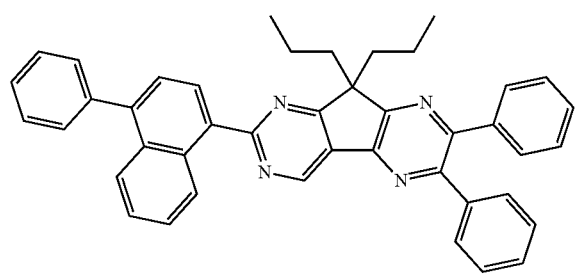
C-46
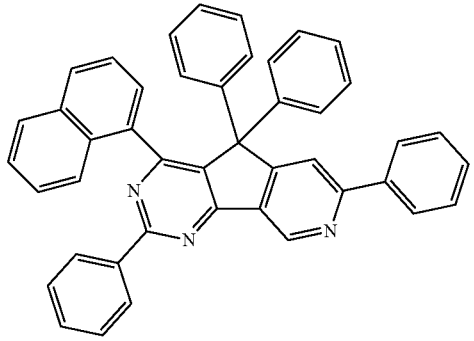
C-50
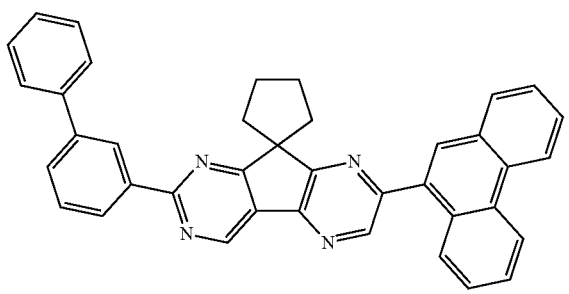
C-47
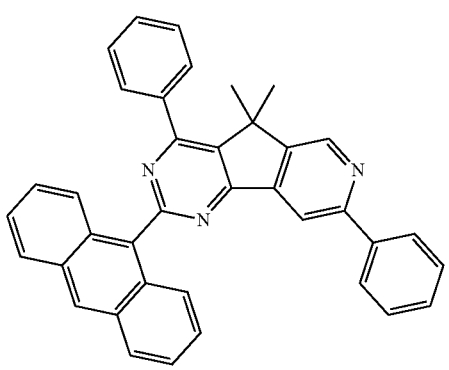
C-51
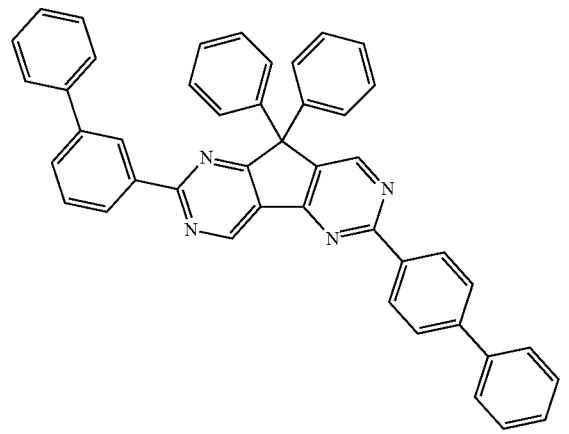
C-48
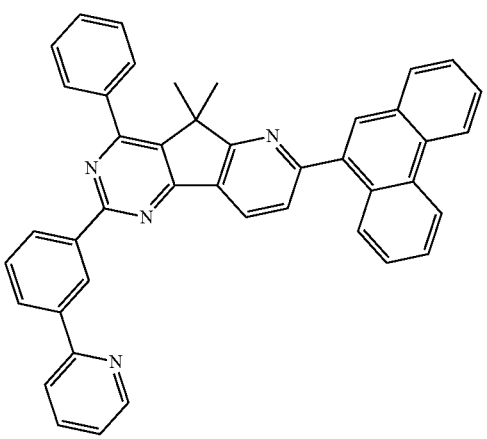
C-52
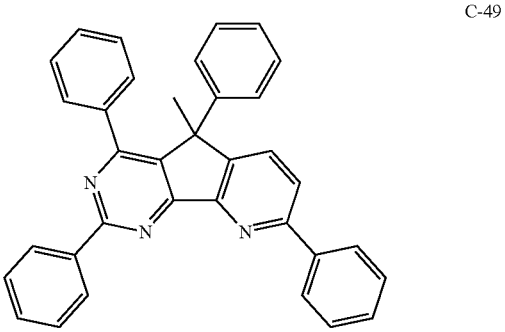
C-49
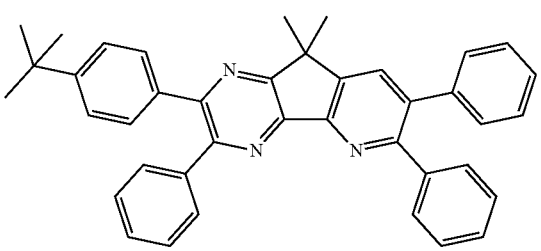
C-53

C-54
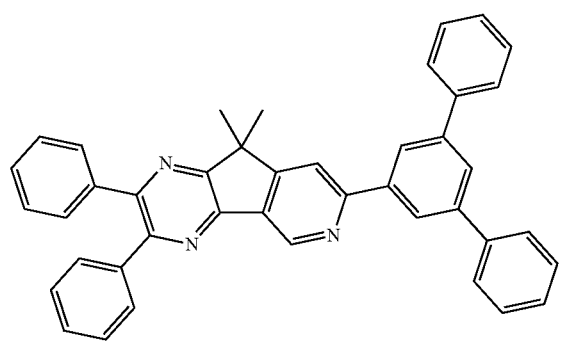
C-55
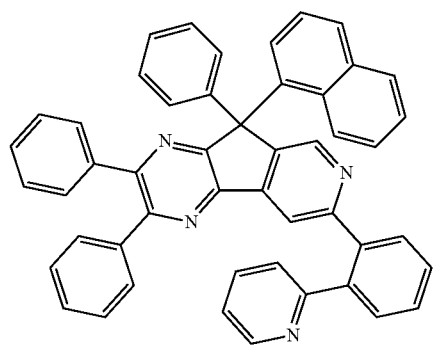
C-56
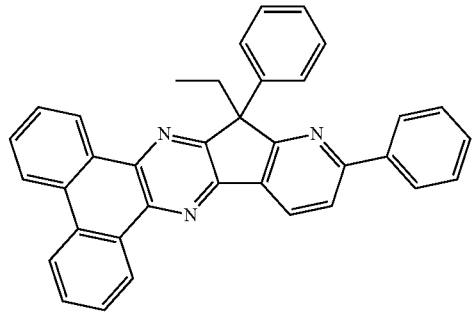
C-57
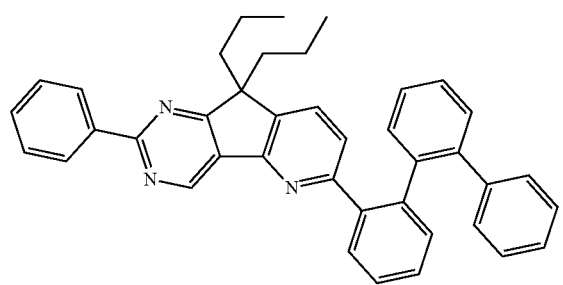
C-58
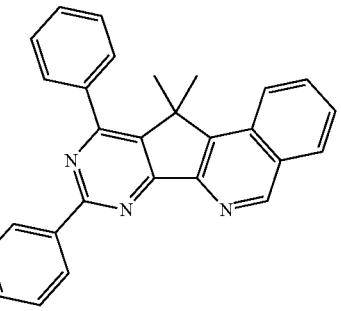
C-59
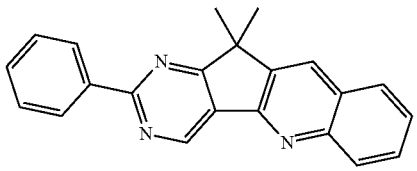
C-60
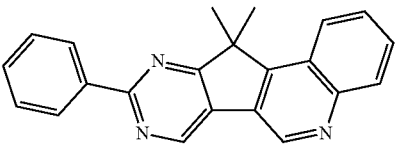
C-61
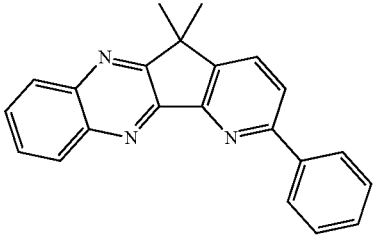
C-62
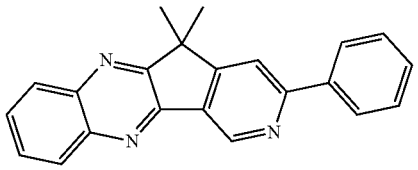
C-63
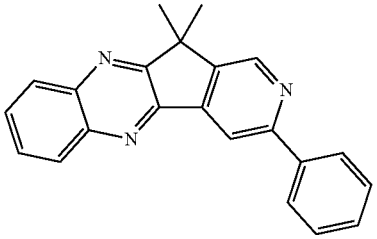
C-64
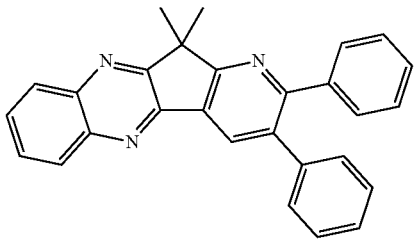

C-65
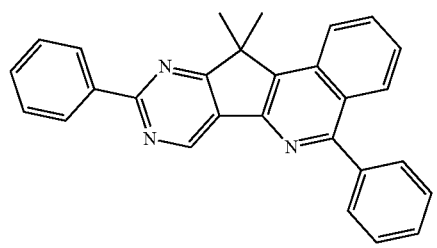
C-66
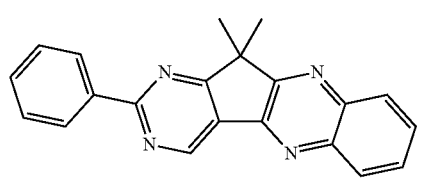
C-67
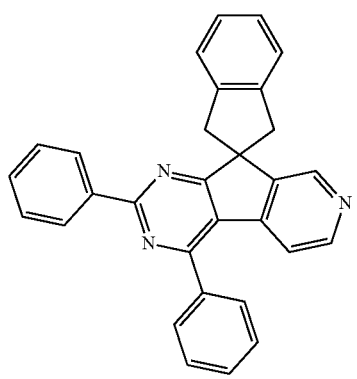
C-68
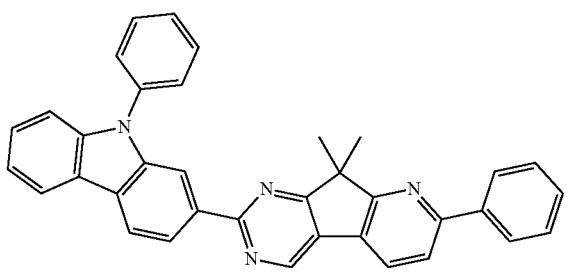
C-69
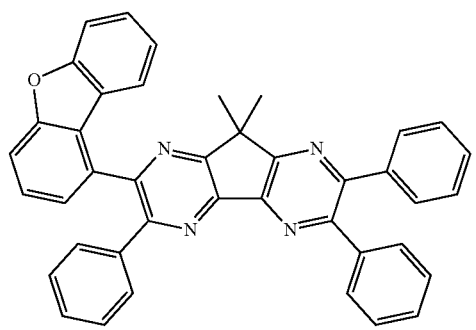
C-70
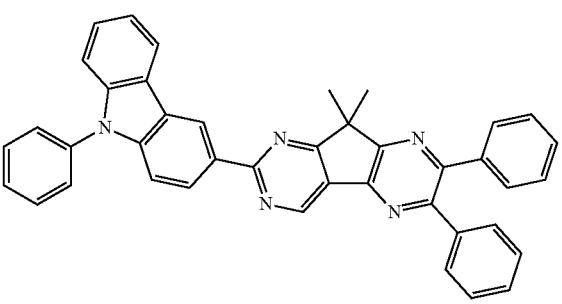
C-71
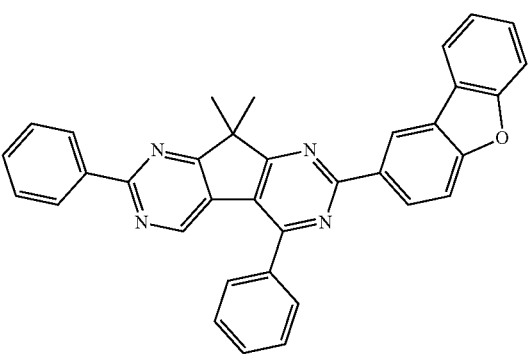
C-72
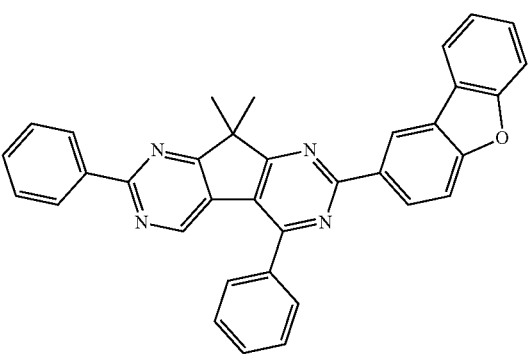
C-73
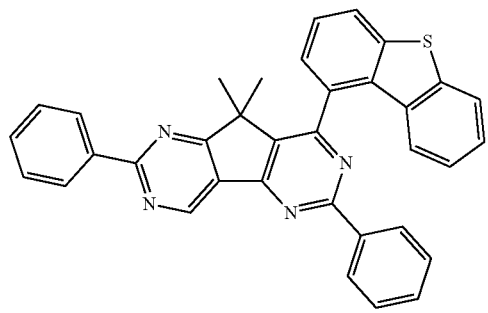

C-74
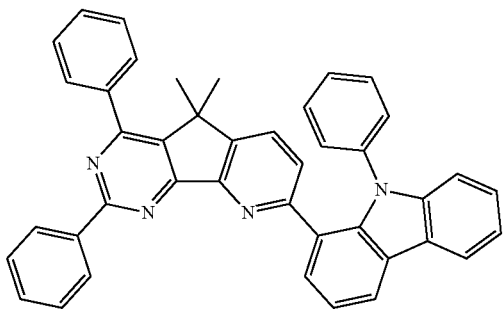
C-78
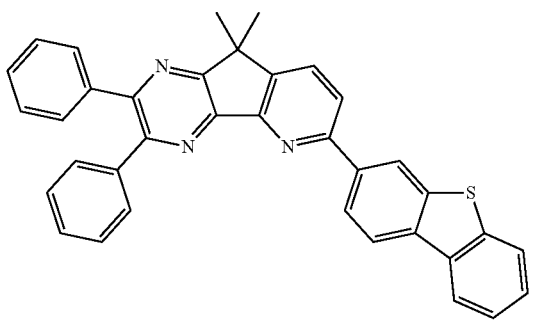
C-75
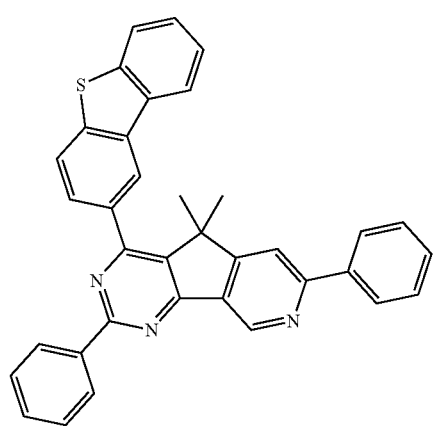
C-79
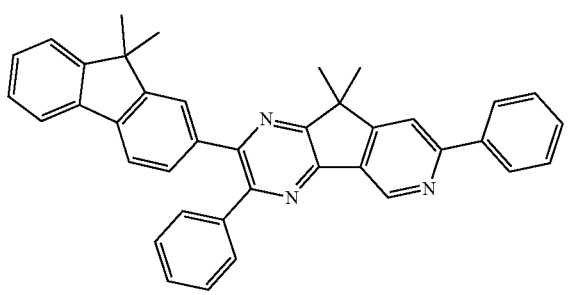
C-76
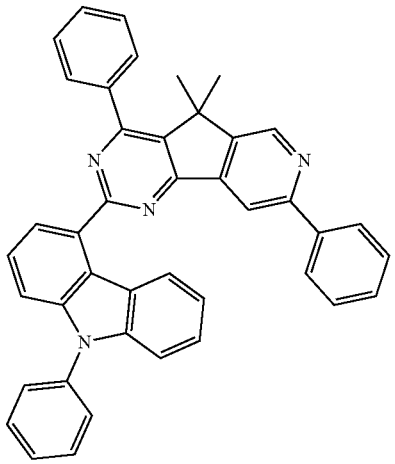
C-80
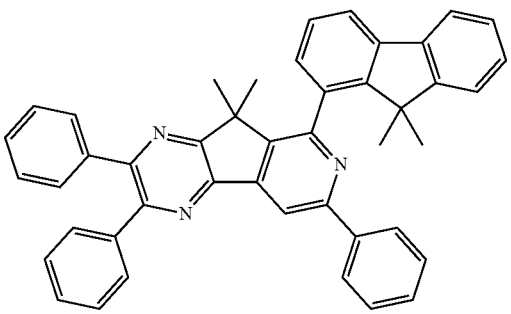
C-81
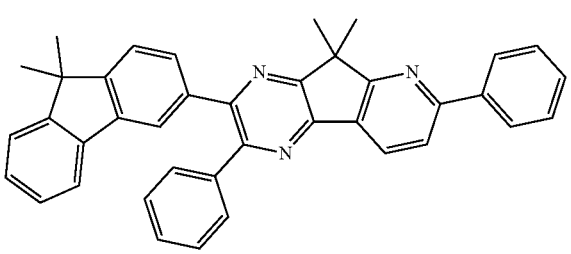
C-77
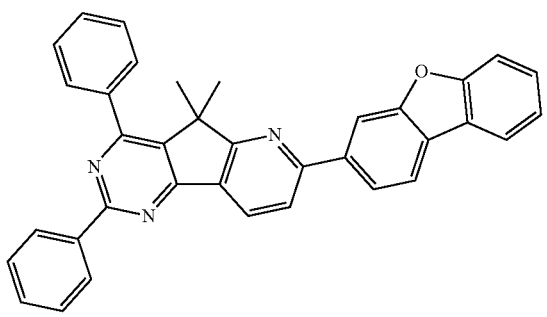
C-82
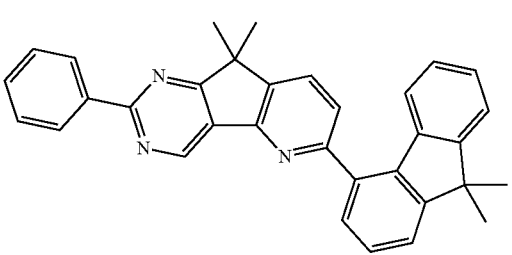

-continued
C-83
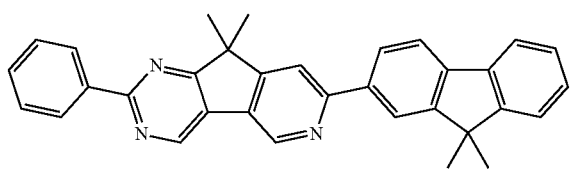
C-84
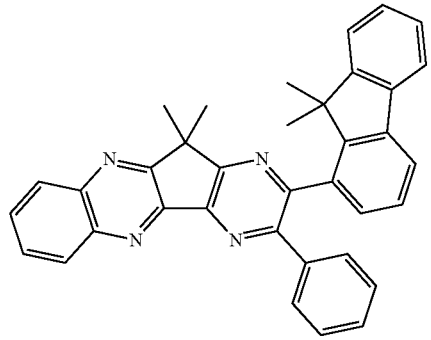
C-85
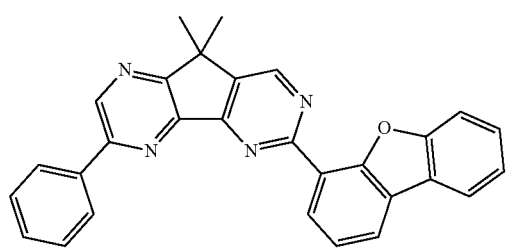
C-86
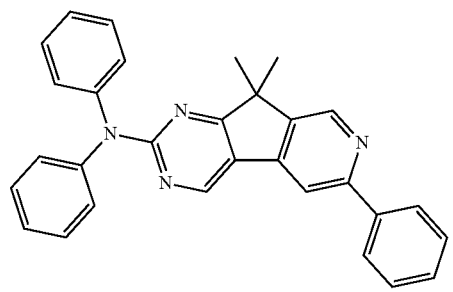
C-87
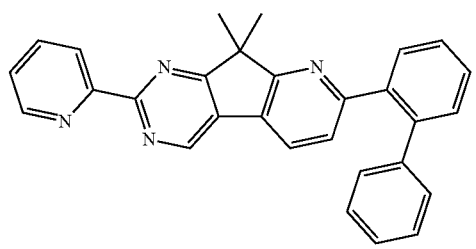
C-88
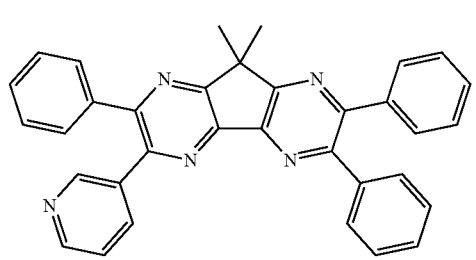
-continued
C-89
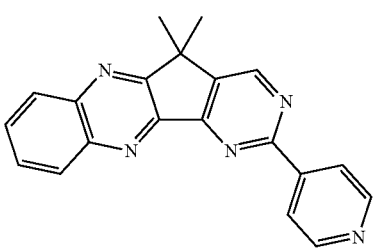
C-90
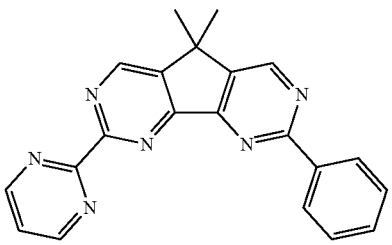
C-91
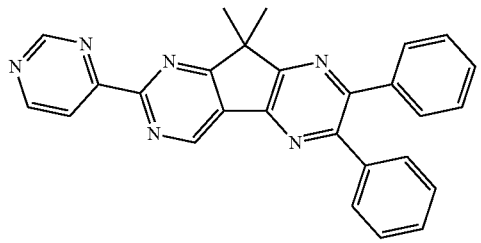
C-92
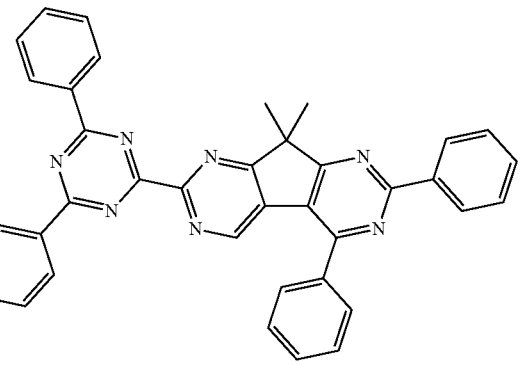
C-93
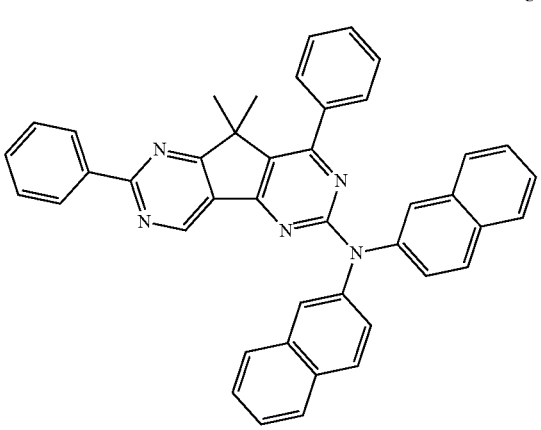

C-94
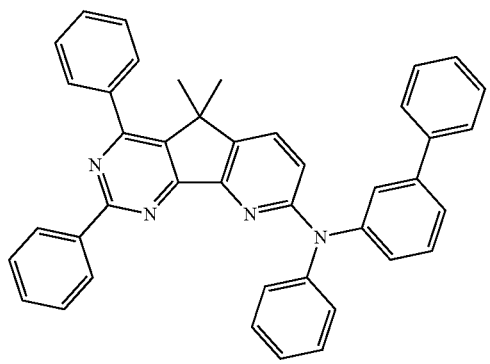
C-98
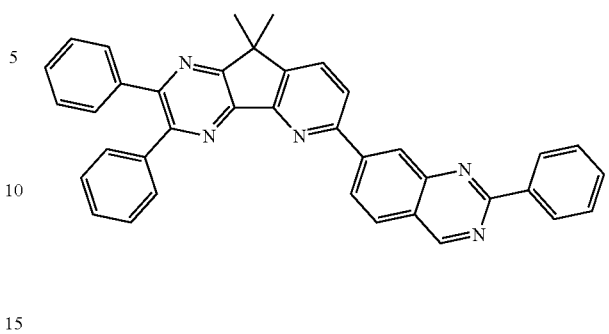
C-95
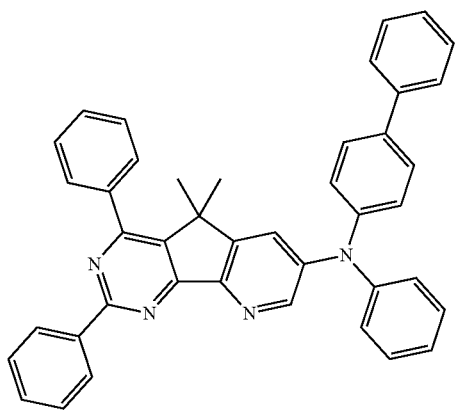
C-99
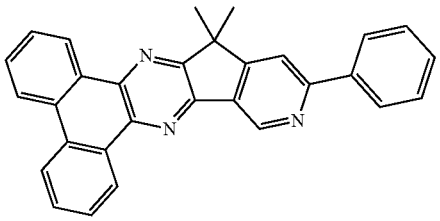
C-96
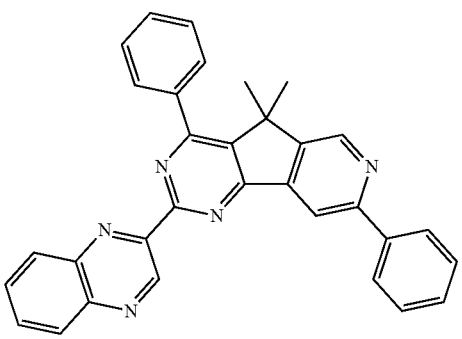
C-100
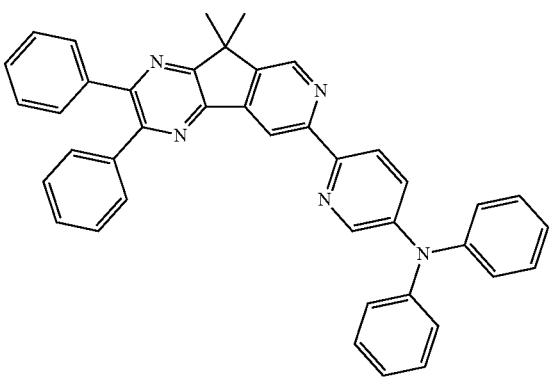
C-97
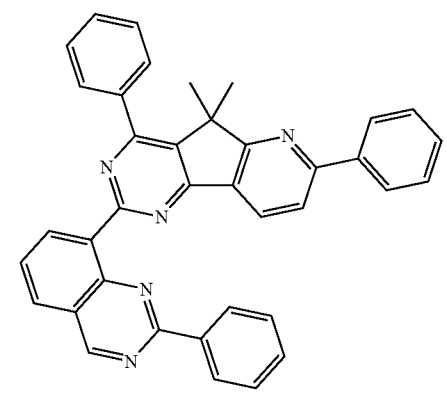
C-101
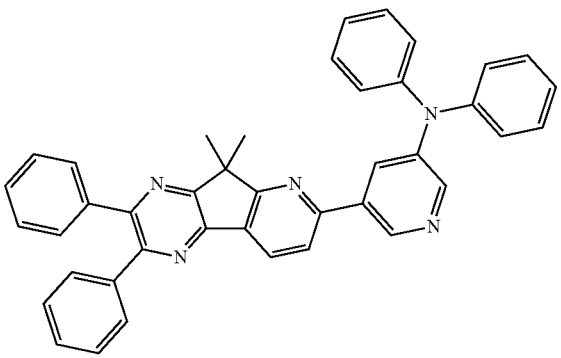

C-102

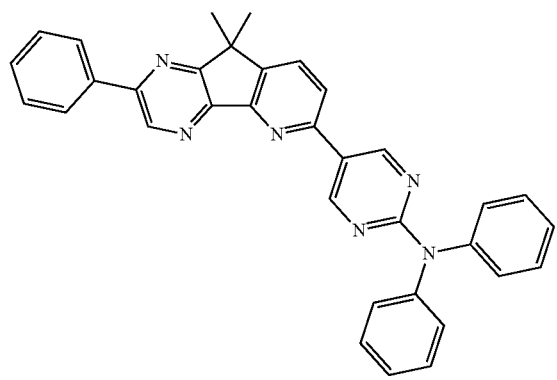

The compound represented by formula 1 according to the present disclosure may be produced by a synthetic method known to one skilled in the art, and for example, by referring to International Patent Publication No. WO 2009/126584 (published on Oct. 15, 2009), Korean Patent Application Laying-Open No. 2017-003472 (published on Jan. 9, 2017), Korean Patent Application Laying-Open No. 2017-0123053 (published on Nov. 7, 2017) etc., or according to the following reaction schemes 1 to 3, but is not limited thereto.

[Reaction Scheme 1]

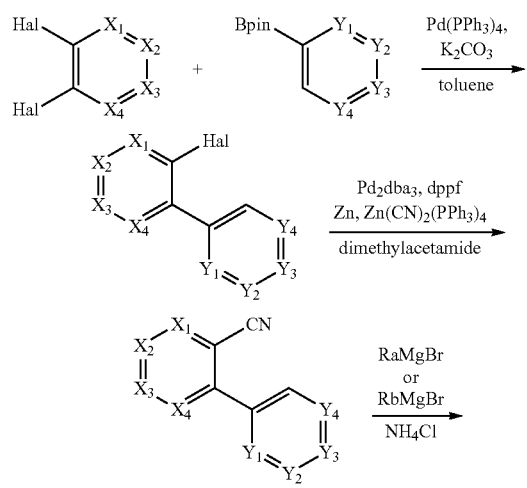

[Reaction Scheme 2]

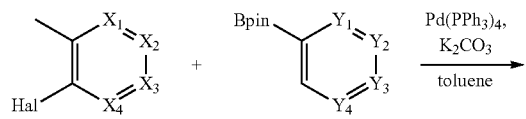
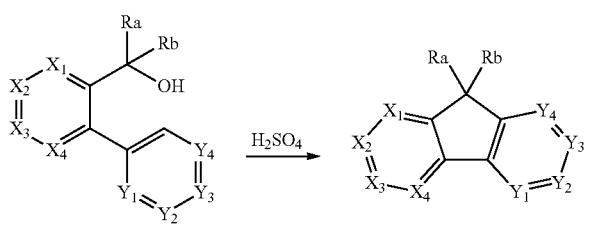

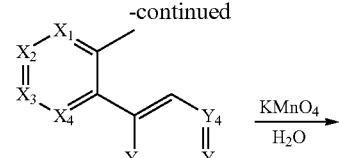
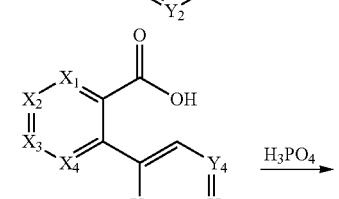
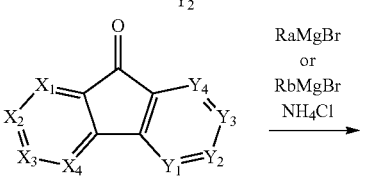

[Reaction Scheme 3]

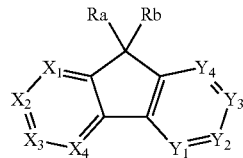

In reaction schemes 1 to 3, each of the substituents is as defined in formula 1; and Hal represents a halogen.

Although illustrative synthesis examples of the compound represented by formula 1 of the present disclosure are described above, one skilled in the art will be able to readily understand that all of them are based on a Buchwald- Hartwig cross-coupling reaction, an N-arylation reaction, a H-mont-mediated etherification reaction, a Miyaura borylation reaction, a Suzuki cross-coupling reaction, an Intramolecular acid-induced cyclization reaction, a Pd(II)-catalyzed oxidative cyclization reaction, a Grignard reaction, a Heck reaction, a Cyclic Dehydration reaction, an $SN_1$ substitution reaction, an $SN_2$ substitution reaction, and a Phosphine-mediated reductive cyclization reaction, etc., and the reactions above proceed even when substituents which are defined in formula 1 above, but are not specified in the specific synthesis examples, are bonded.

The present disclosure provides an organic electroluminescent material comprising the organic electroluminescent compound represented by formula 1, and an organic electroluminescent device comprising the material. The material may consist of the organic electroluminescent compound of the present disclosure alone, or may further comprise conventional materials contained in an organic electroluminescent material.

The organic electroluminescent compound of formula 1 of the present disclosure may be comprised in at least one layer of the light-emitting layer, the hole injection layer, the hole transport layer, the hole auxiliary layer, the light-emitting auxiliary layer, the electron transport layer, the electron buffer layer, the electron injection layer, the interlayer, the hole blocking layer, and the electron blocking layer, preferably in the light-emitting layer. When used in the light-emitting layer, the organic electroluminescent compound of formula 1 of the present disclosure may be comprised as a host material. Preferably, the light-emitting layer may further comprise one or more dopants. If necessary, the organic electroluminescent compound of the present disclosure may be used as a co-host material. That is, the light-emitting layer may further comprise an organic electroluminescent compound other than the organic electroluminescent compound of formula 1 of the present disclosure (a first host material) as a second host material. In this case, the weight ratio of the first host material and the second host material is about 1:99 to about 99:1. When at least two materials are comprised in one layer, they may be mixture-evaporated to form a layer or may be separately co-evaporated at the same time to form a layer.

The second host material may be any known host and, for example, may comprise a compound represented by the following formula 11, but is not limited thereto.

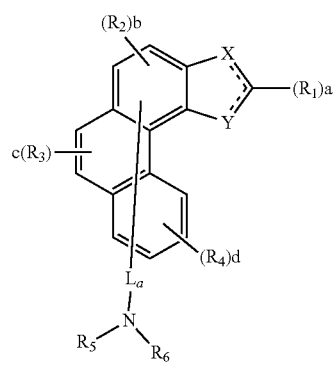

(11)

In formula 11,

X and Y, each independently, represent —N═, —NR$_7$—, —O—, or —S—, with the proviso that any one of X and Y represents —N═, and the other one of X and Y represents —NR$_7$—, —O—, or —S—;

R$_1$ represents a substituted or unsubstituted (C6-C30)aryl, or a substituted or unsubstituted (3- to 30-membered) heteroaryl;

R$_2$ to R$_7$, each independently, represent hydrogen, deuterium, a halogen, a cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of a (C3-C30) aliphatic ring(s) and a (C6-C30) aromatic ring(s), a substituted or unsubstituted mono- or di-(C1-C30)alkylamino, a substituted or unsubstituted mono- or di-(C2-C30)alkenylamino, a substituted or unsubstituted (C1-C30) alkyl(C2-C30)alkenylamino, a substituted or unsubstituted mono- or di-(C6-C30)arylamino, a substituted or unsubstituted (C1-C30)alkyl(C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C2-C30) alkenyl(C6-C30)arylamino, a substituted or unsubstituted (C2-C30)alkenyl(3- to 30-membered) heteroarylamino, or a substituted or unsubstituted (C6-C30)aryl(3- to 30-membered)heteroarylamino; or may be linked to an adjacent substituent to form a ring(s);

L$_a$ represents a single bond, a substituted or unsubstituted (C6-C30)arylene, or a substituted or unsubstituted (3- to 30-membered)heteroarylene; and a represents 1, b and c, each independently, represent an integer of 1 or 2, and d represents an integer of 1 to 4, in which if b to d are an integer of 2 or more, each of R$_2$ to each of R$_4$ may be the same or different.

In formula 11, according to one embodiment of the present disclosure, any one of X and Y represents —N═, and the other one of X and Y represents —O— or —S—. For example, X represents —N═, and Y represents —O—; X represents —O—, and Y represents —N═; or X represents —S—, and Y represents —N═.

In formula 11, according to one embodiment of the present disclosure, R$_1$ represents a substituted or unsubstituted (C6-C30)aryl, or a substituted or unsubstituted (5- to 25-membered)heteroaryl. According to another embodiment of the present disclosure, R$_1$ represents a substituted or unsubstituted (C6-C30)aryl, or a substituted (5- to 20-membered)heteroaryl. For example, R$_1$ may be an unsubstituted phenyl, an unsubstituted biphenyl, an unsubstituted naphthyl, a fluorenyl substituted with a methyl(s), a benzofluorenyl substituted with a methyl(s), an unsubstituted dibenzofuranyl, an unsubstituted dibenzothiophenyl, a spiro[fluorene-fluoren]yl, a spiro[fluorene-benzofluoren]yl, or an unsubstituted pyridyl.

In formula 11, according to one embodiment of the present disclosure, R$_2$ to R$_7$, each independently, represent hydrogen, a substituted or unsubstituted (C6-C25)aryl, a substituted or unsubstituted (3- to 25-membered)heteroaryl, or a substituted or unsubstituted mono- or di-(C6-C25) arylamino; or may be linked to an adjacent substituent to form a substituted or unsubstituted, mono- or polycyclic, (C3-C30) alicyclic or aromatic ring, in which carbon atoms of the formed alicyclic or aromatic ring may be replaced with at least one heteroatom selected from nitrogen, oxygen, and sulfur. According to another embodiment of the present disclosure, $R_2$ to $R_7$, each independently, represent hydrogen, a substituted or unsubstituted (C6-C25)aryl, a substituted or unsubstituted (5- to 25-membered)heteroaryl, a substituted or unsubstituted di(C6-C18)arylamino, a substituted or unsubstituted mono- or di-(3- to 30-membered)heteroarylamino, or a substituted or unsubstituted (C6-C30)aryl(3- to 30-membered)heteroarylamino; or may be linked to each other to form a substituted or unsubstituted, mono- or polycyclic, (C3-C25) alicyclic or aromatic ring, in which carbon atoms of the formed alicyclic or aromatic ring may be replaced with at least one heteroatom selected from nitrogen and sulfur, and the heteroaryl may contain at least one heteroatom selected from B, N, O, S, Si, and P. Specifically, $R_1$, $R_5$, and $R_6$, each independently, may be a substituted or unsubstituted phenyl, a substituted or unsubstituted naphthyl, a substituted or unsubstituted biphenyl, a substituted or unsubstituted terphenyl, a substituted or unsubstituted phenanthrenyl, a substituted or unsubstituted fluorenyl, a substituted or unsubstituted benzofluorenyl, a substituted or unsubstituted triphenylenyl, a substituted or unsubstituted spirobifluorenyl, a substituted or unsubstituted pyridyl, a substituted or unsubstituted triazinyl, a substituted or unsubstituted pyrimidinyl, a substituted or unsubstituted quinolyl, a substituted or unsubstituted quinazolinyl, a substituted or unsubstituted quinoxalinyl, a substituted or unsubstituted benzoquinazolinyl, a substituted or unsubstituted benzoquinoxalinyl, a substituted or unsubstituted benzofuropyrimidinyl, a substituted or unsubstituted carbazolyl, a substituted or unsubstituted dibenzothiophenyl, a substituted or unsubstituted benzothiophenyl, a substituted or unsubstituted dibenzofuranyl, a substituted or unsubstituted benzofuranyl, a substituted or unsubstituted naphthyridinyl, a substituted or unsubstituted benzonaphthofuranyl, or a substituted or unsubstituted benzonaphthothiophenyl. For example, at least one of $R_5$ and $R_6$, each independently, may be at least one selected from the group consisting of a substituted or unsubstituted phenyl, a substituted or unsubstituted o-biphenyl, a substituted or unsubstituted m-biphenyl, a substituted or unsubstituted p-biphenyl, a substituted or unsubstituted fluorenyl, a substituted or unsubstituted naphthyl, a substituted or unsubstituted phenanthrenyl, a substituted or unsubstituted dibenzofuranyl, a substituted or unsubstituted dibenzothiophenyl, or a substituted or unsubstituted benzofluorenyl. For example, $R_1$ may be a phenyl, a biphenyl, or a pyridyl; $R_2$ and $R_3$ may be hydrogen; $R_4$ may be hydrogen or a phenyl; $R_5$ and $R_6$, each independently, may be a substituted phenyl, a naphthyl, a biphenyl, a phenanthrenyl, a dimethylfluorenyl, a diphenylfluorenyl, a naphthylphenyl, a phenylnaphthyl, a dimethylbenzofluorenyl, a terphenyl, a spirobifluorenyl, a benzofuranyl, a benzothiophenyl, a dibenzothiophenyl, a dibenzofuranyl unsubstituted or substituted with a phenyl(s), a carbazolyl substituted with a phenyl(s), or a benzonaphthofuranyl; and the substituent(s) of the substituted phenyl may be at least one of a phenyl substituted with at least one of deuterium, a methyl(s), and a tert-butyl(s); an anthracenyl; a fluoranthenyl; a phenylfluorenyl; a cyclohexyl; a pyridyl substituted with a phenyl(s); a phenoxazinyl; and a benzoimidazolyl substituted with a phenyl(s).

In formula 11, according to one embodiment of the present disclosure, a to c, each independently, represent 1, and d represents 1 or 2.

In formula 11, according to one embodiment of the present disclosure, $L_a$ represents a single bond, or a substituted or unsubstituted (C6-C18)arylene. According to another embodiment of the present disclosure, $L_a$ represents a single bond, or an unsubstituted (C6-C12)arylene. For example, $L_a$ may be a single bond, or an unsubstituted phenylene.

According to one embodiment of the present disclosure, the formula 11 may be represented by at least one of the following formulas 11-1 to 11-3.

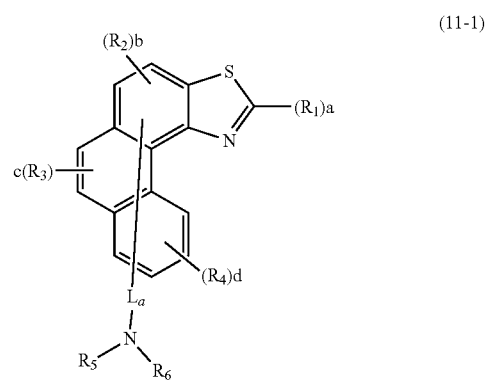

(11-1)

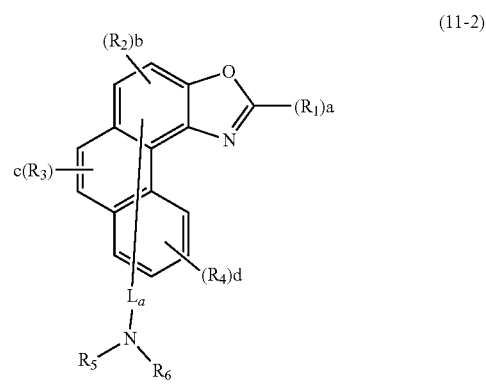

(11-2)

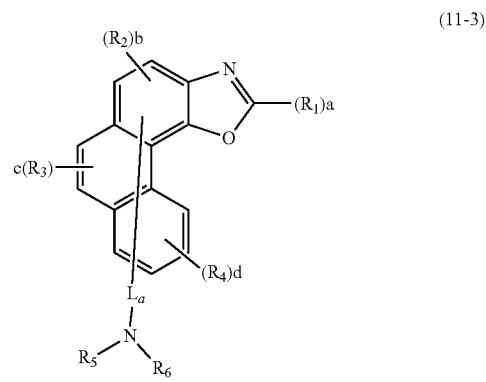

(11-3)

In formulas 11-1 to 11-3, $R_1$ to $R_6$, $L_a$, and a to d are as defined in formula 11.

The compound represented by formula 11 may be at least one selected from the following compounds, but is not limited thereto.

H1-1
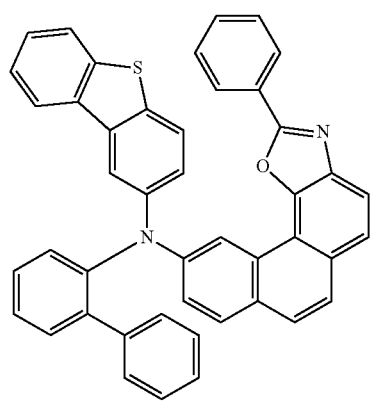
H1-2
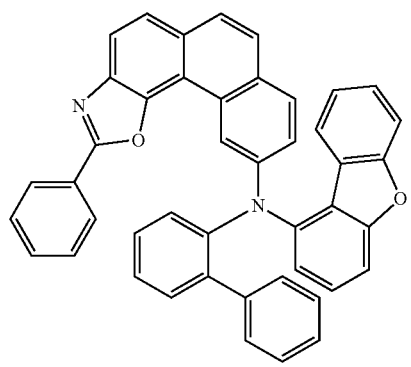
H1-3
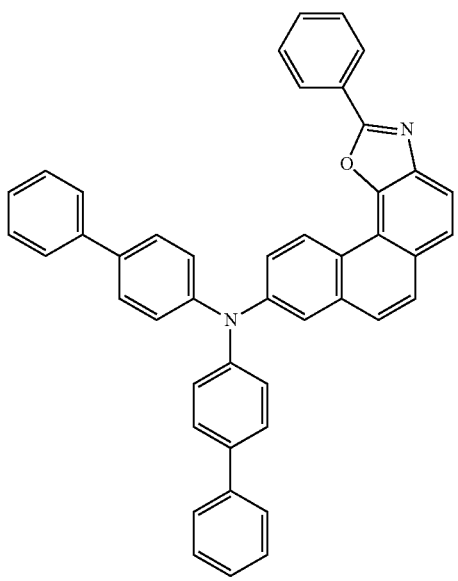
H1-4
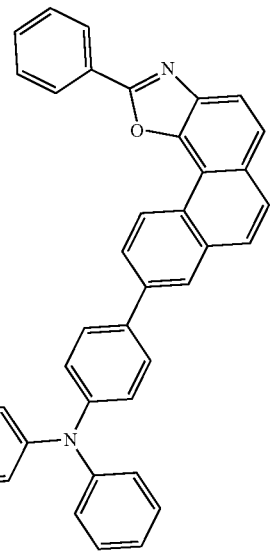
H1-5
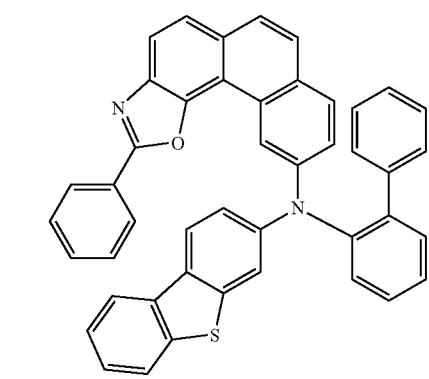
H1-6
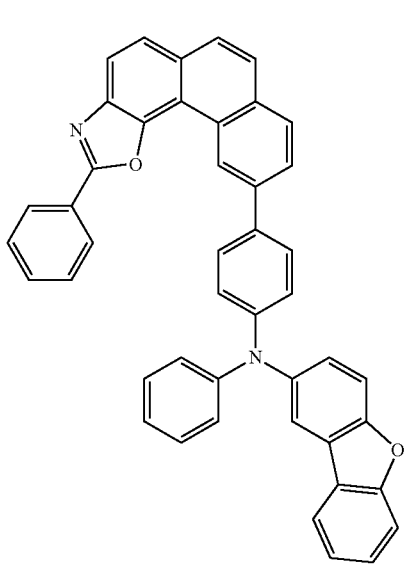

-continued
H1-7
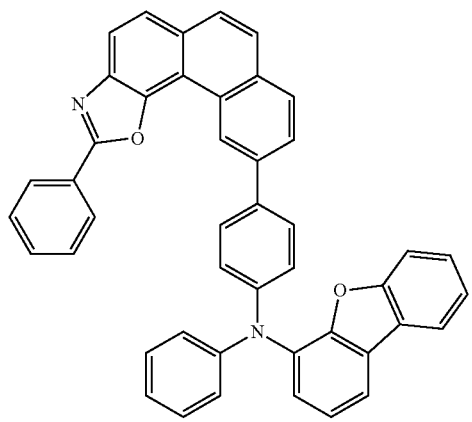
H1-8
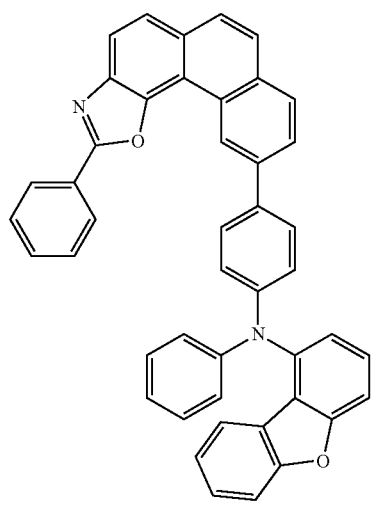
H1-9
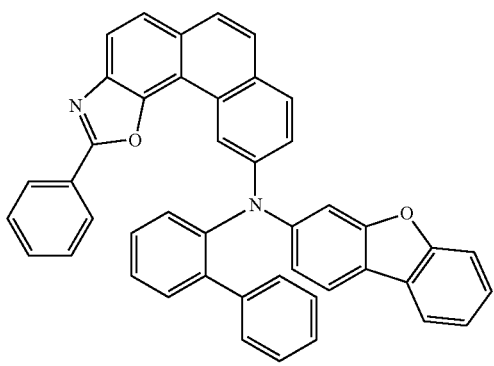
-continued
H1-10
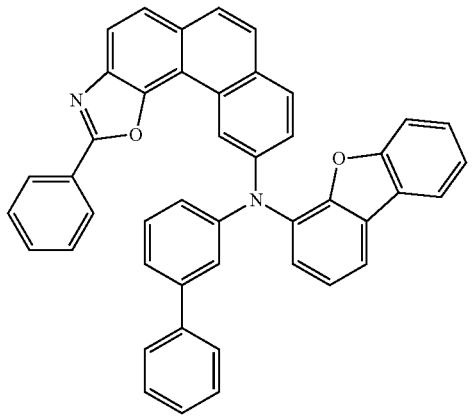
H1-11
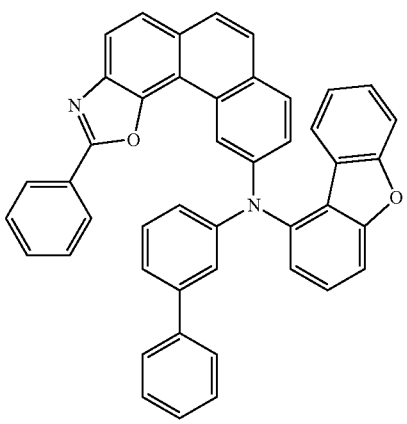
H1-12
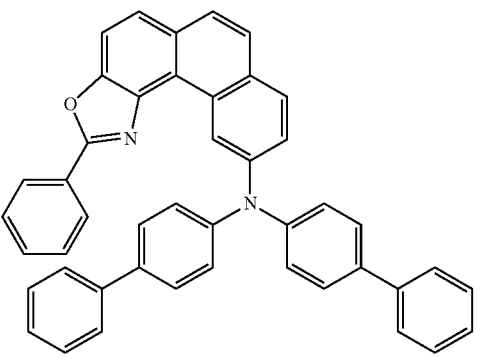
H1-13
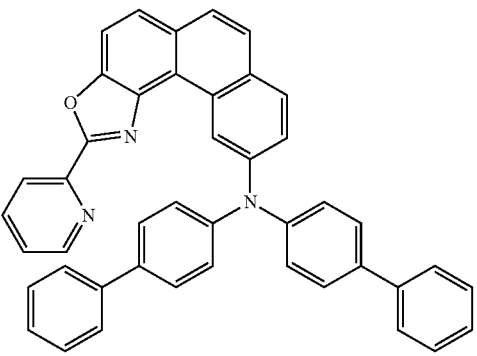

H1-14
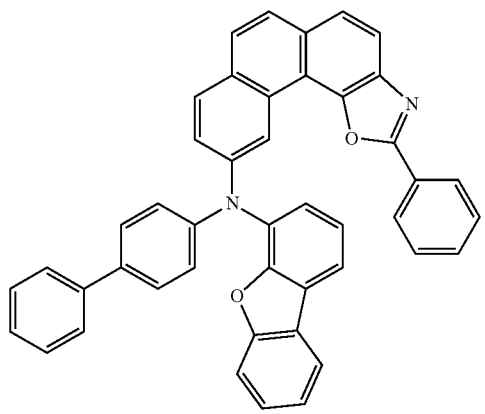
H1-15
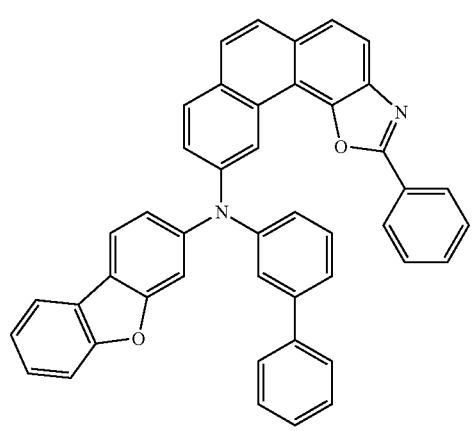
H1-16
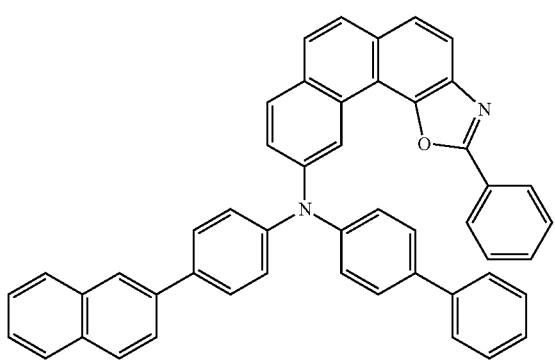
H1-17
H1-18
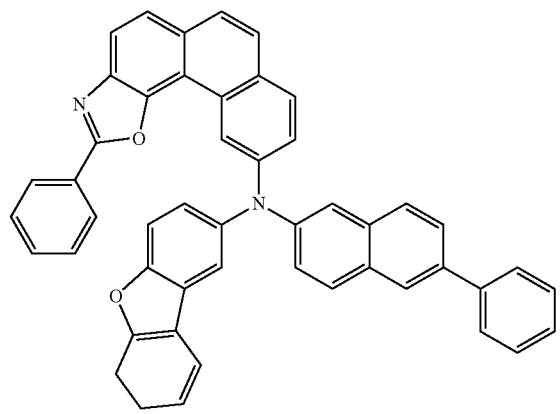
H1-19
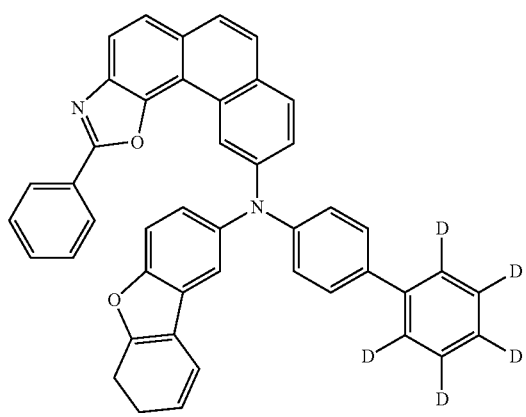
H1-20
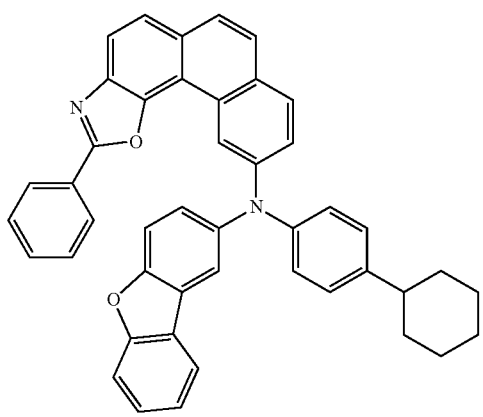

H1-21
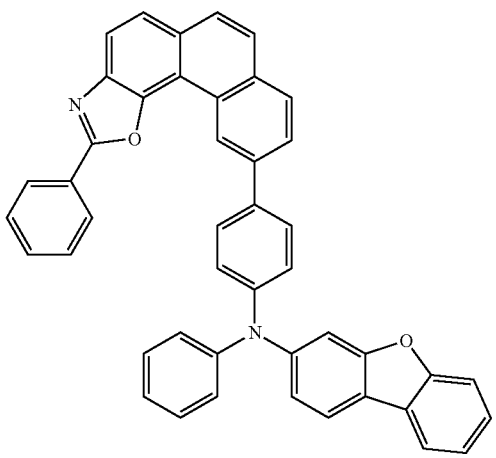
H1-22
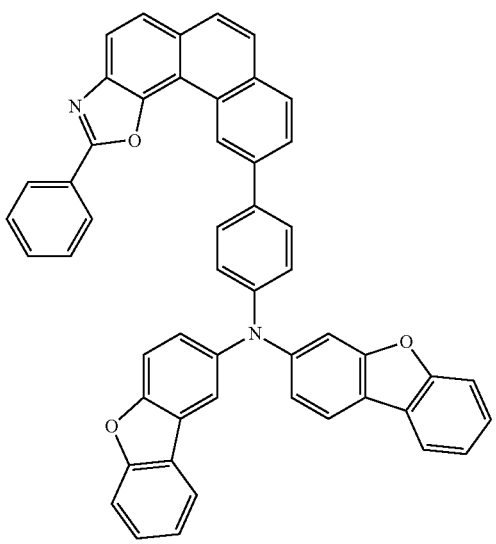
H1-23
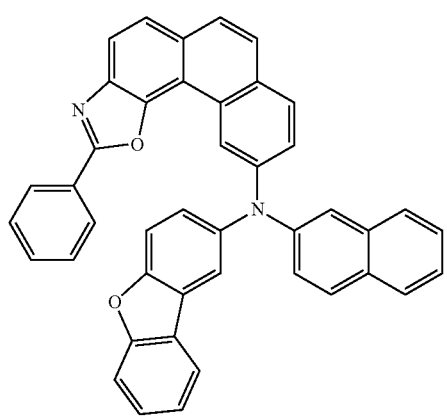
H1-24
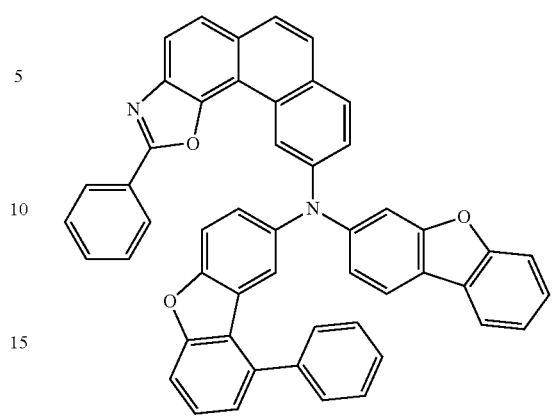
H1-25
H1-26
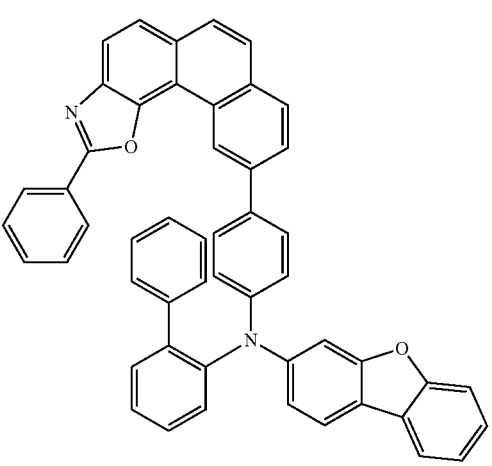

H1-27
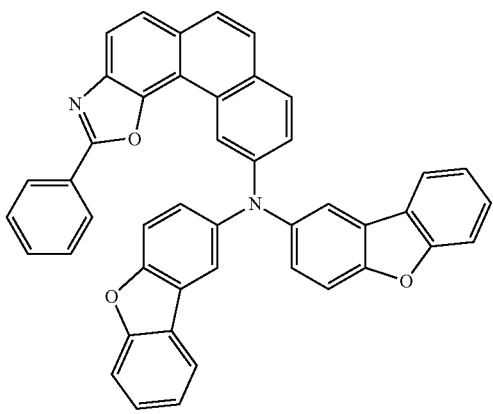
H1-28
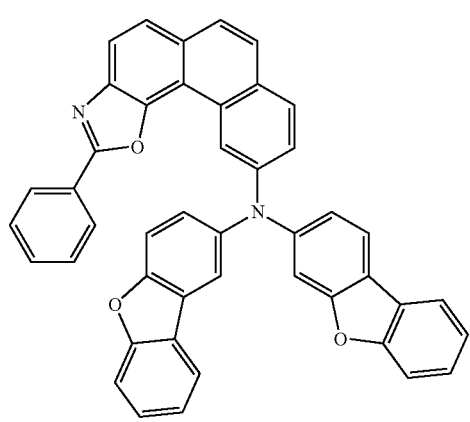
H1-29
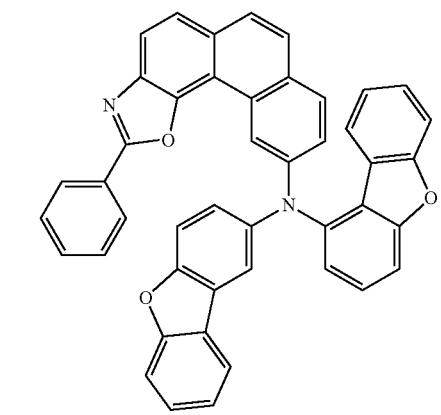
H1-30
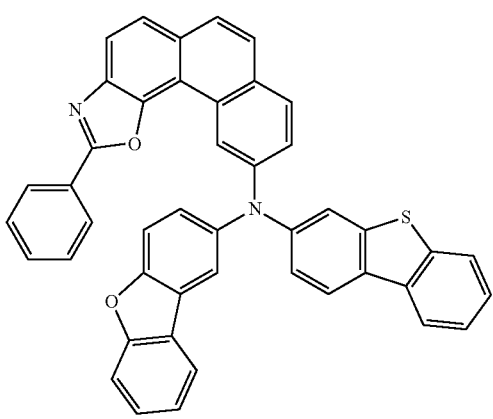
H1-31
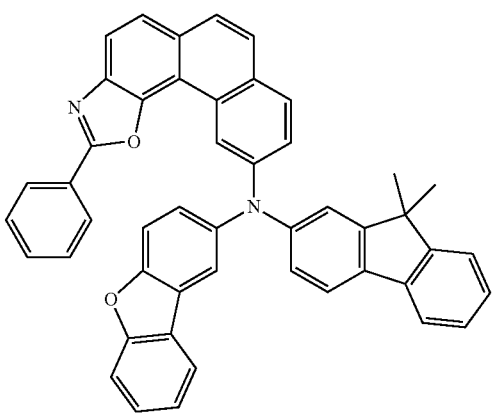
H1-32
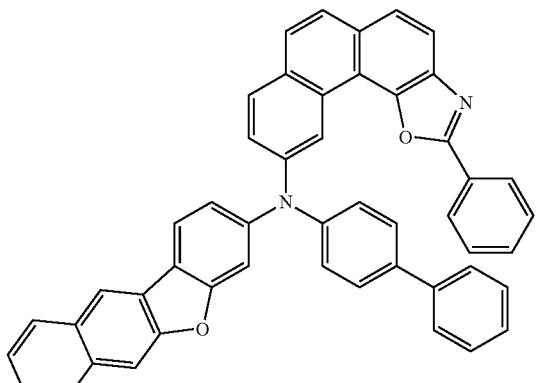
H1-33
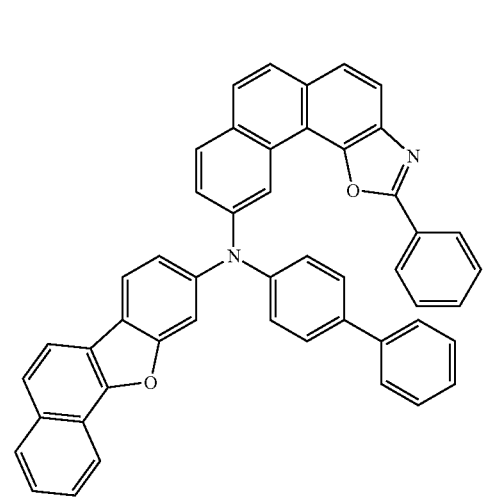

H1-34
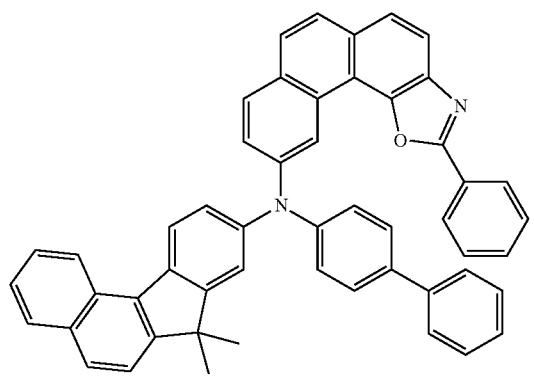
H1-35
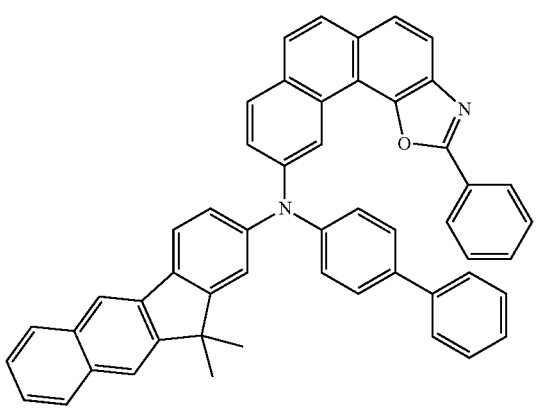
H1-36
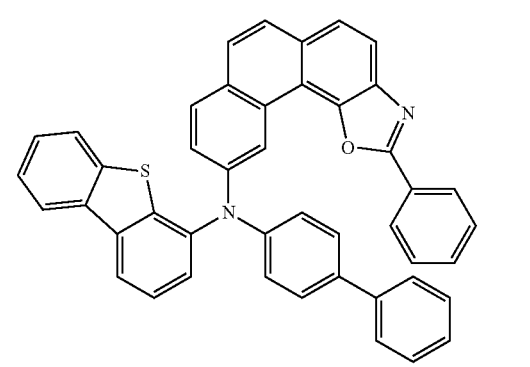
H1-37
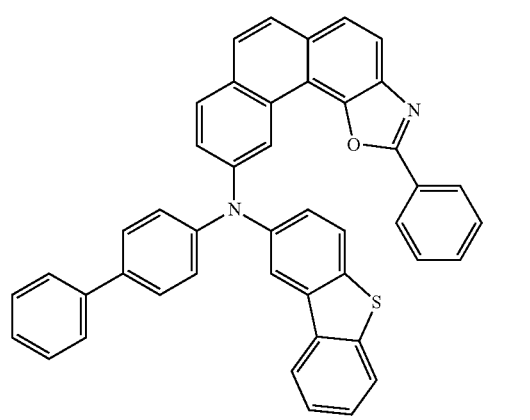
H1-38
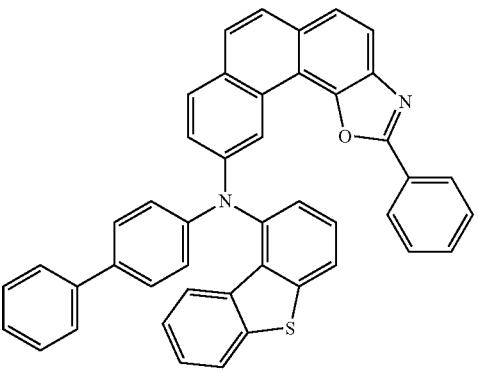
H1-39
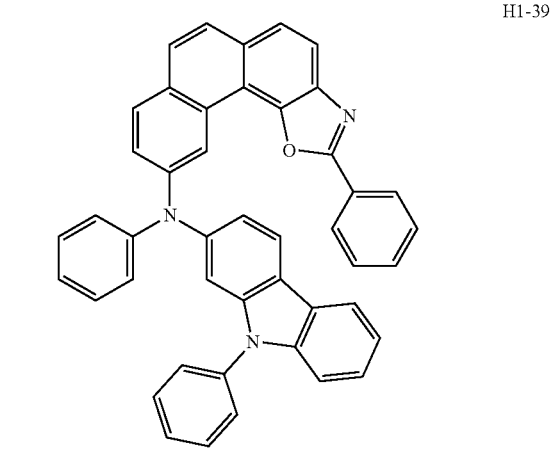
H1-40
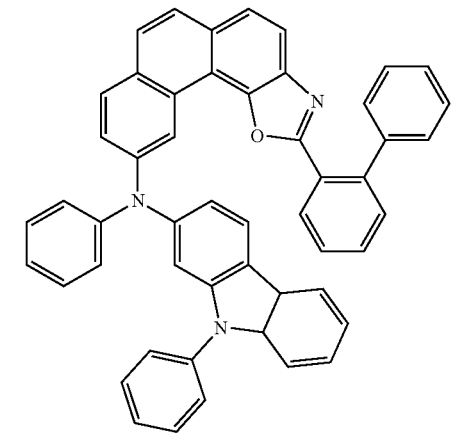

H1-41
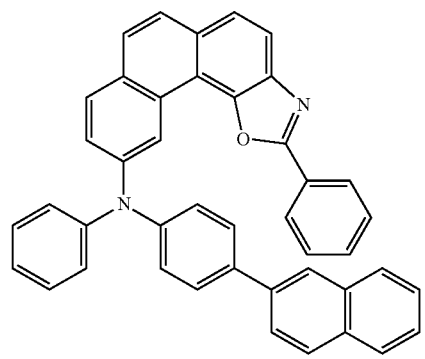
H1-42
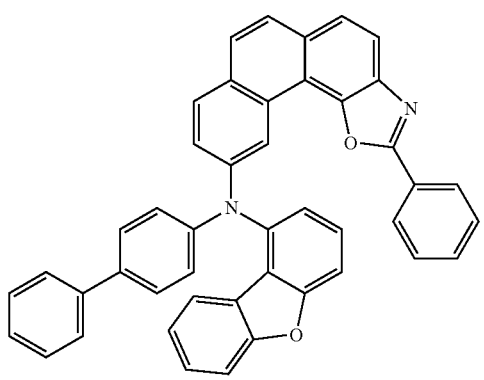
H1-43
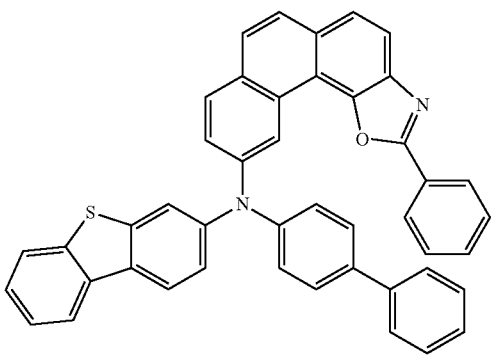
H1-44
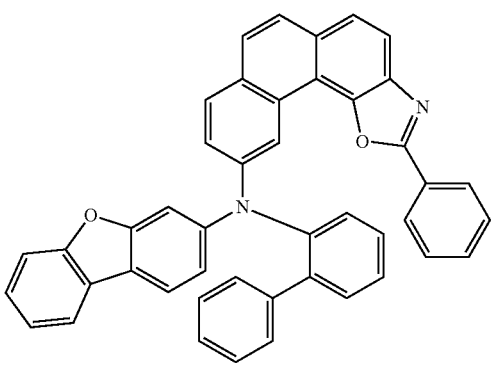
H1-45
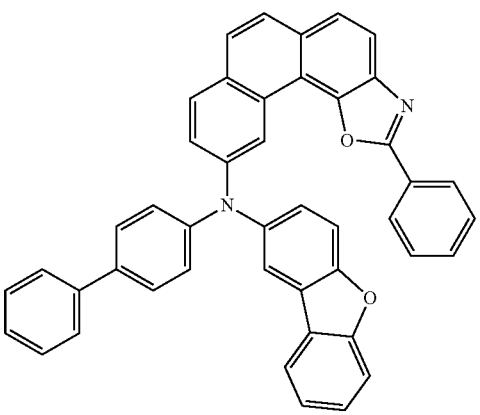
H1-46
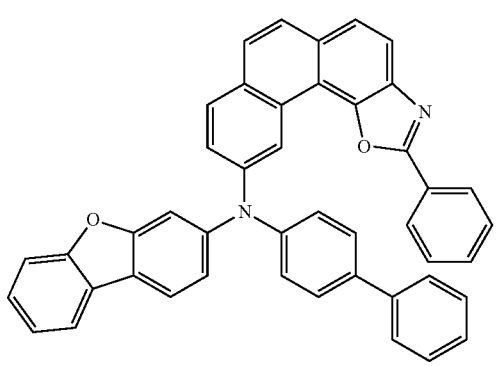
H1-47
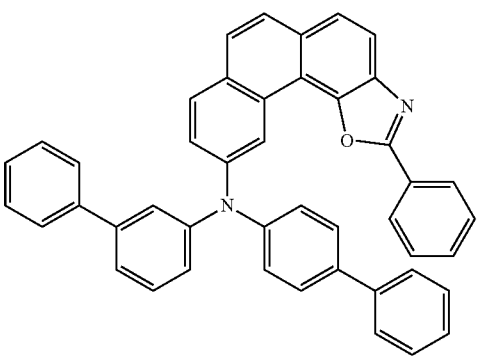
H1-48
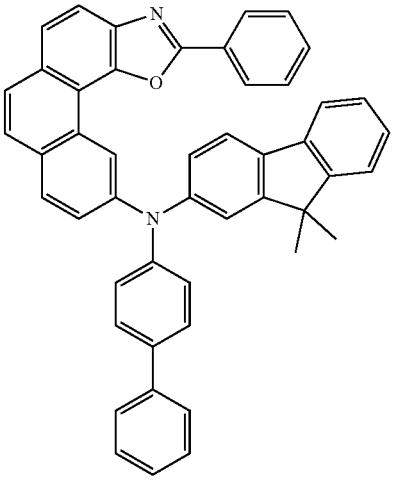

H1-49
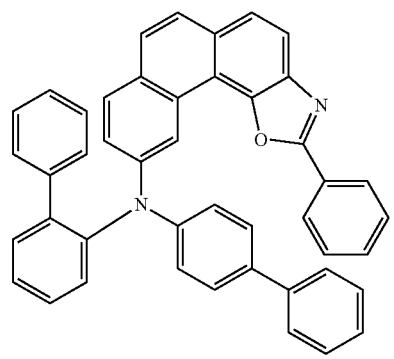
H1-50
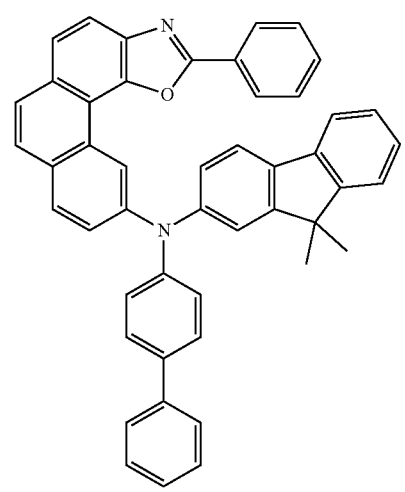
H1-51
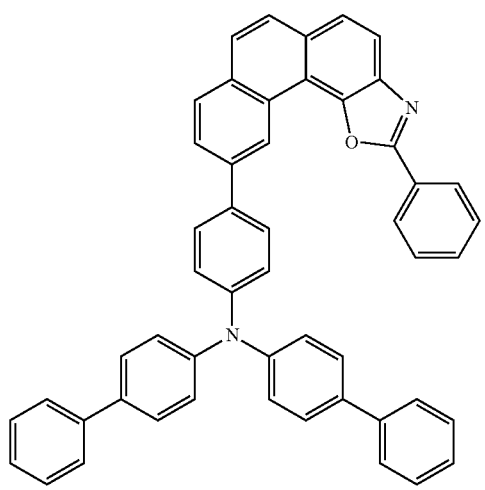
H1-52
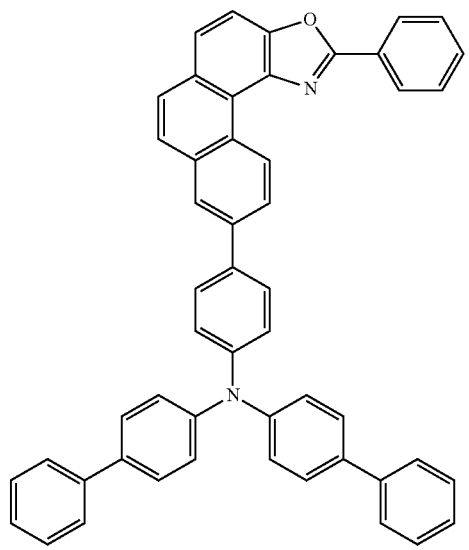
H1-53
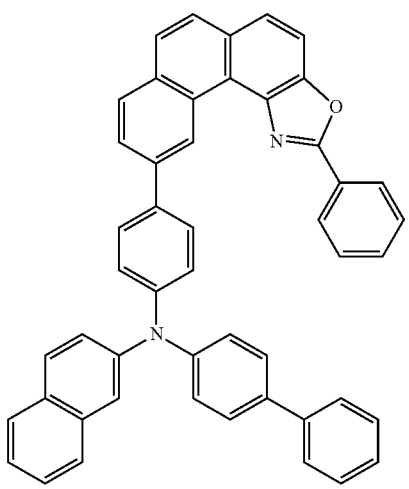
H1-54
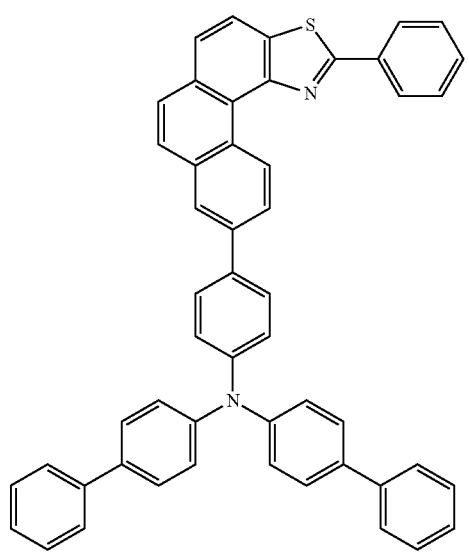

H1-55
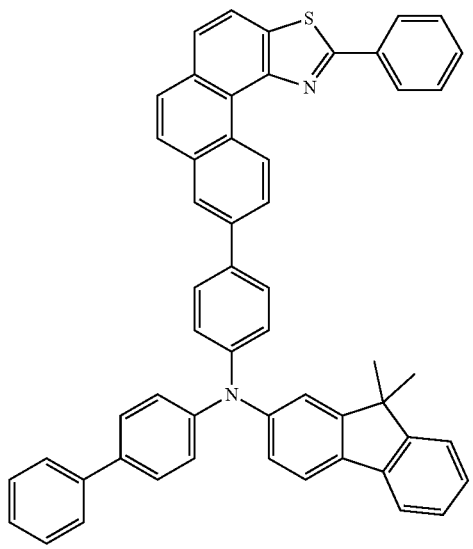
H1-56
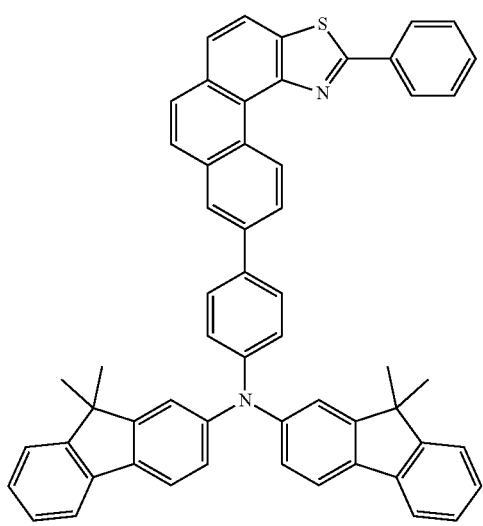
H1-57
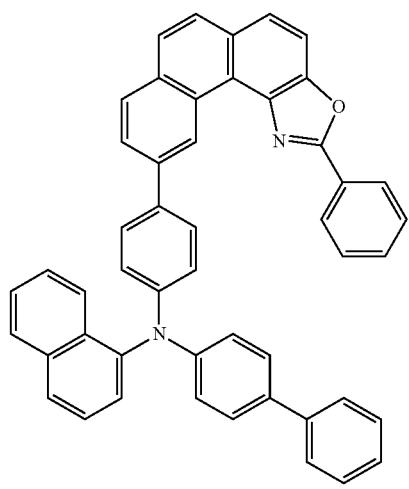
H1-58
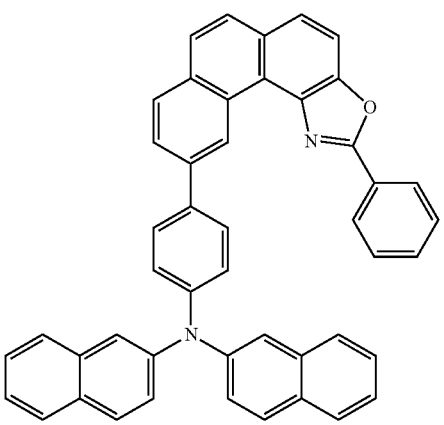
H1-59
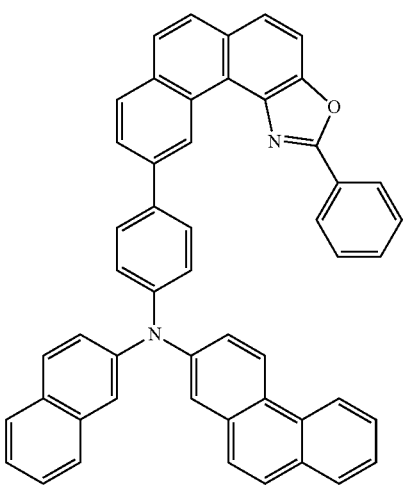
H1-60
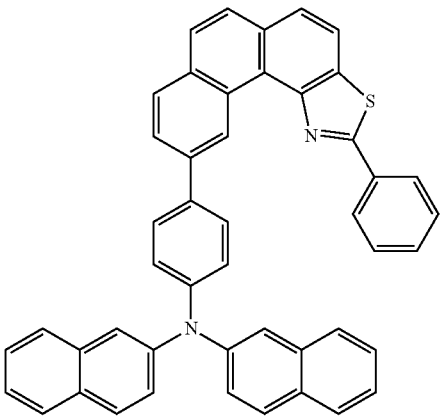

H1-61
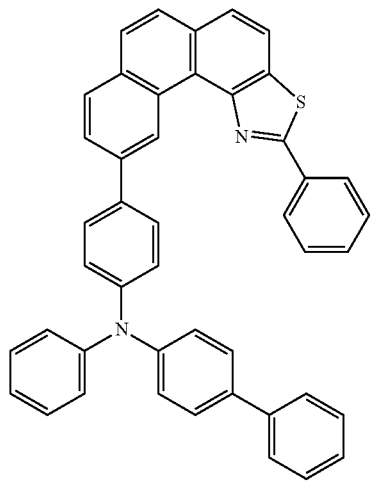
H1-64
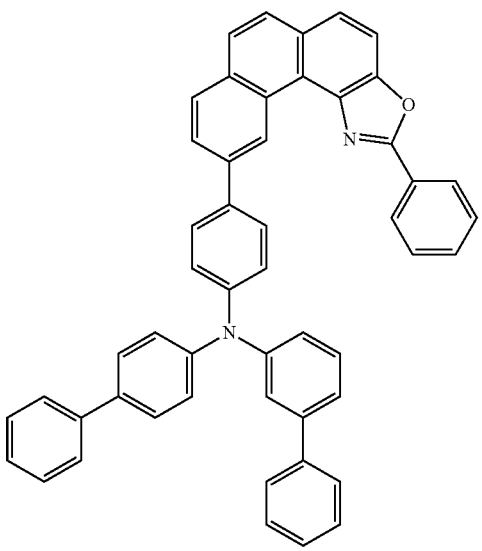
H1-62
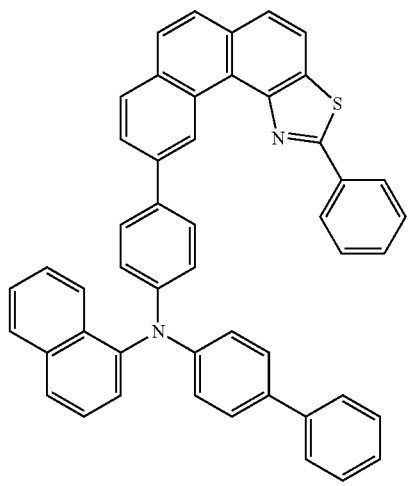
H1-63
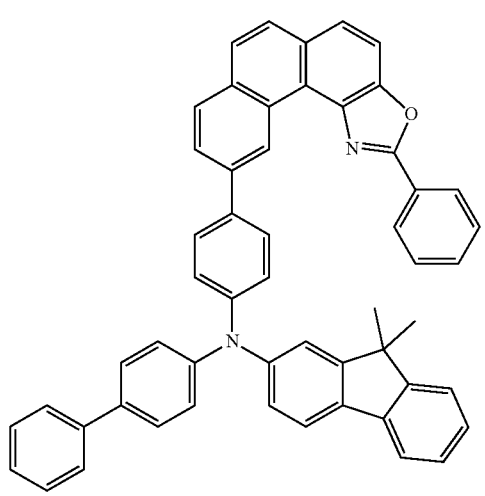
H1-65
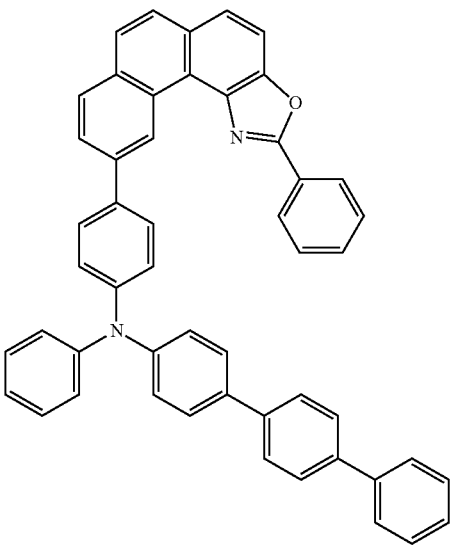

H1-66
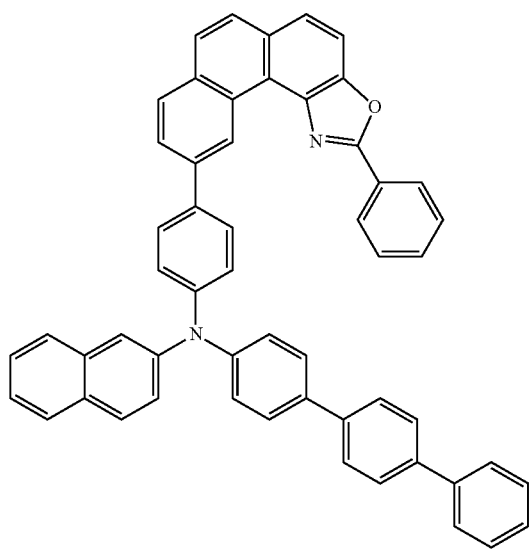
H1-67
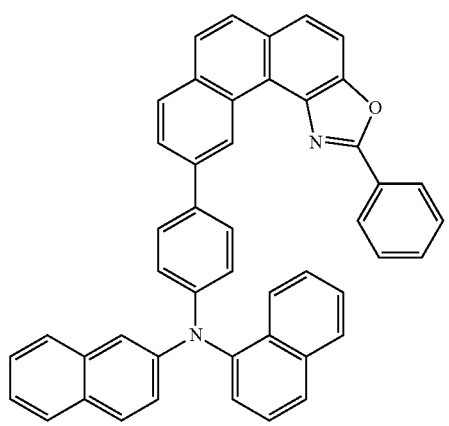
H1-68
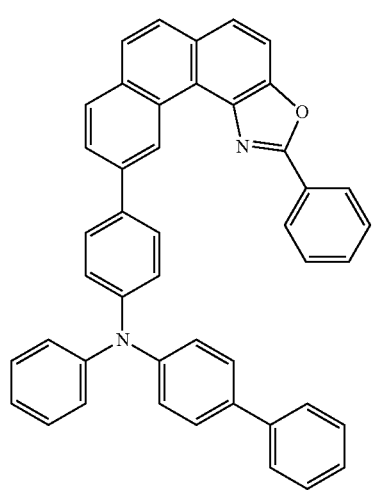
H1-69
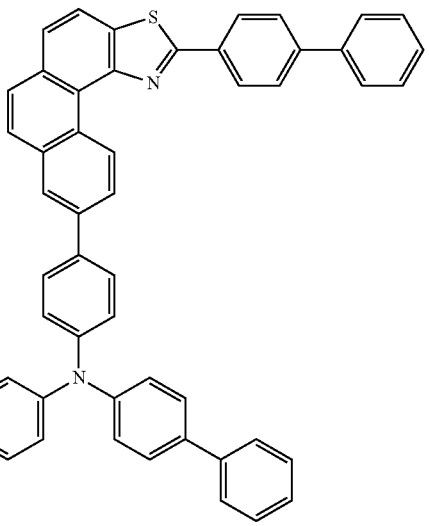
H1-70
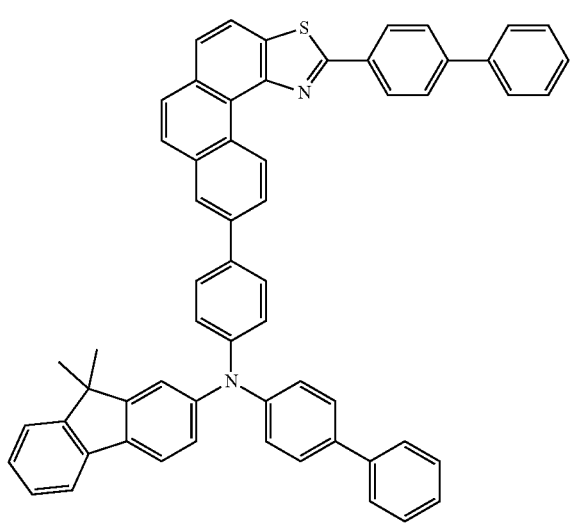
H1-71
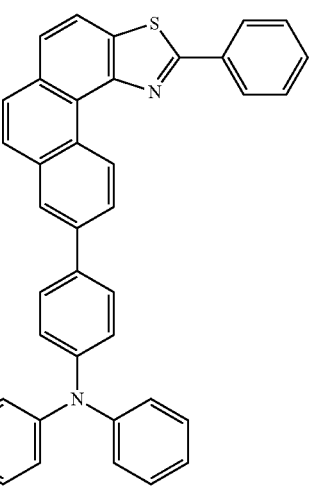

H1-72
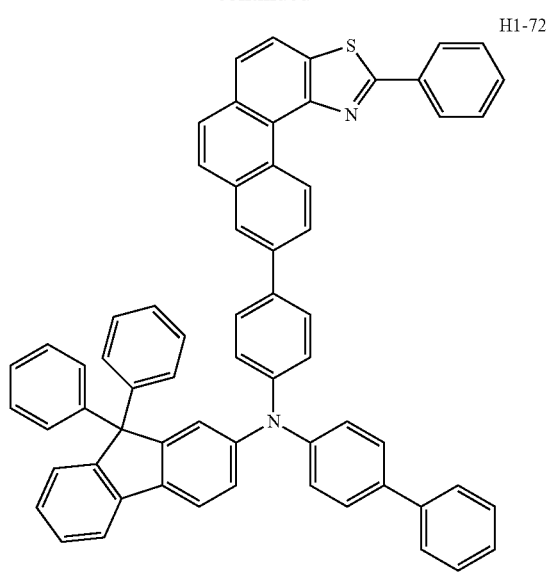
H1-73
H1-74
H1-75
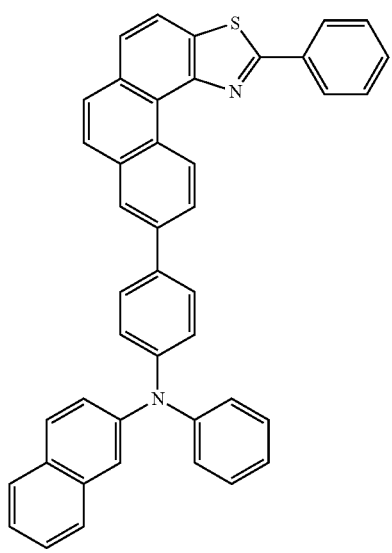
H1-76
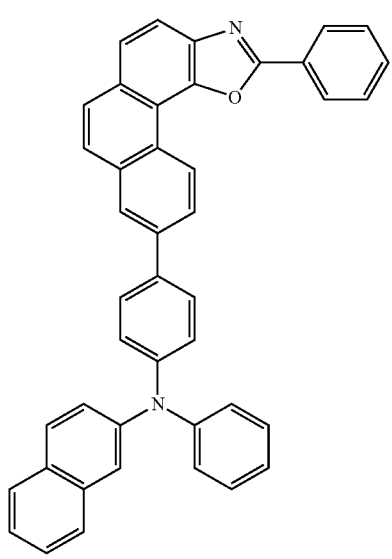
H1-77
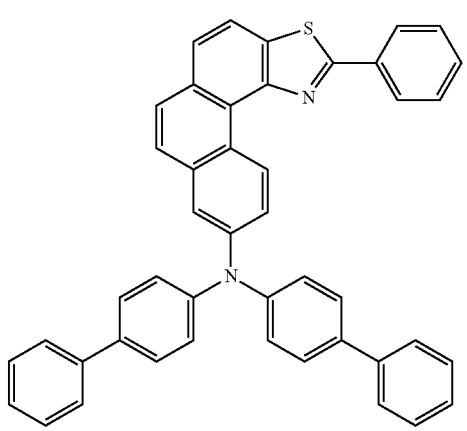

H1-78
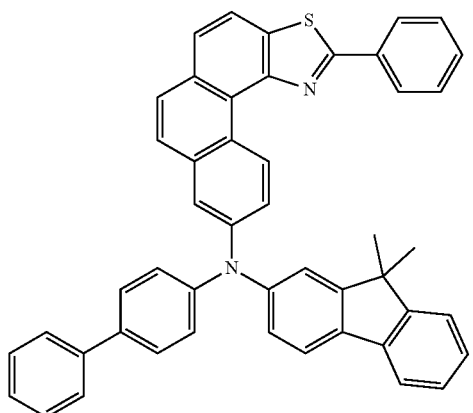
H1-79
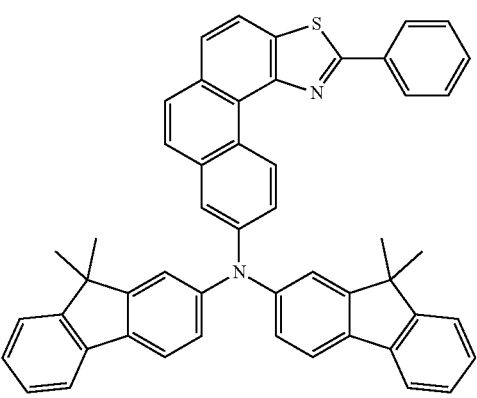
H1-80
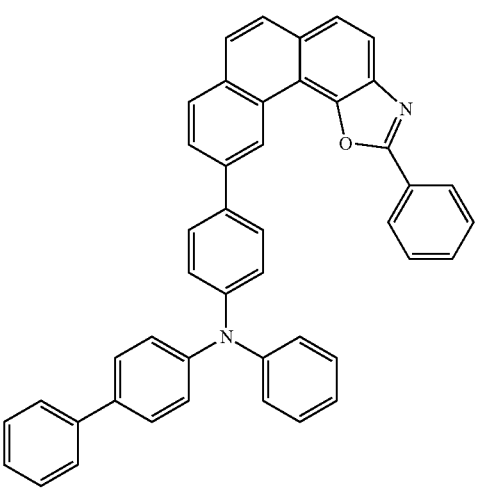
H1-81
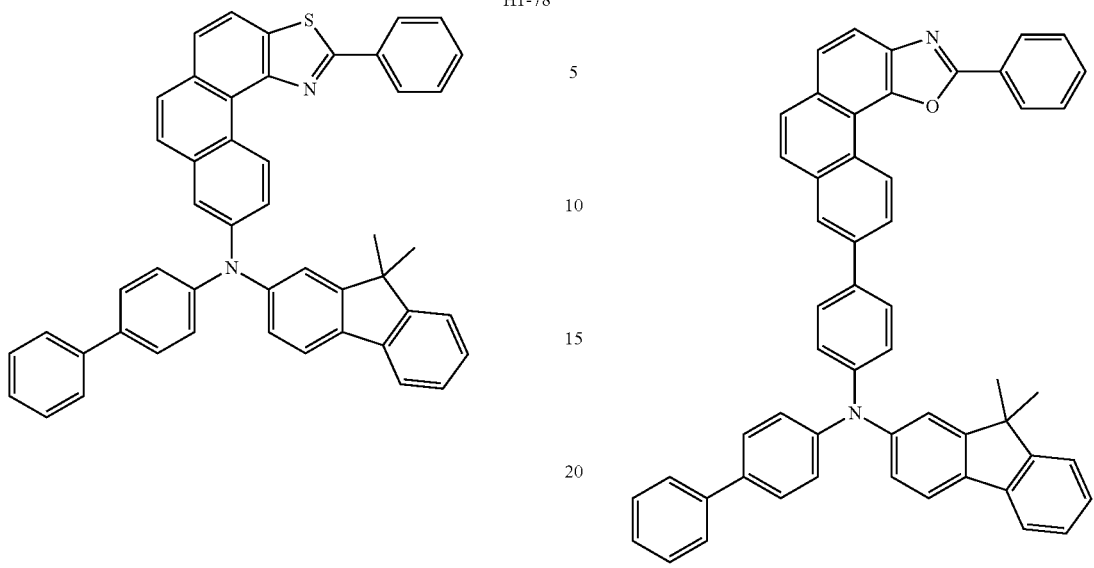
H1-82
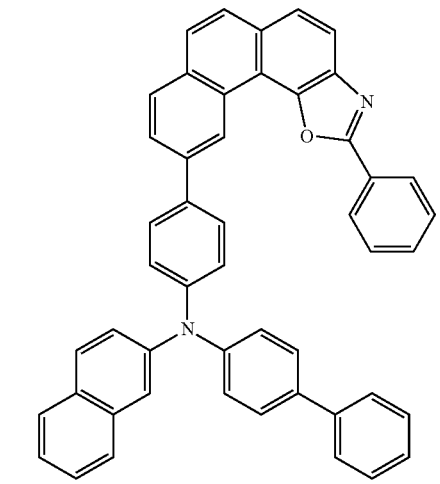
H1-83
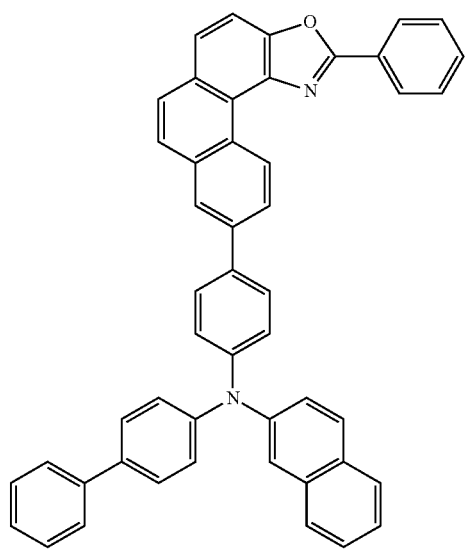

H1-84
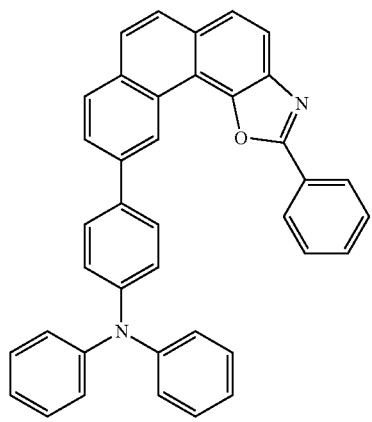
H1-85
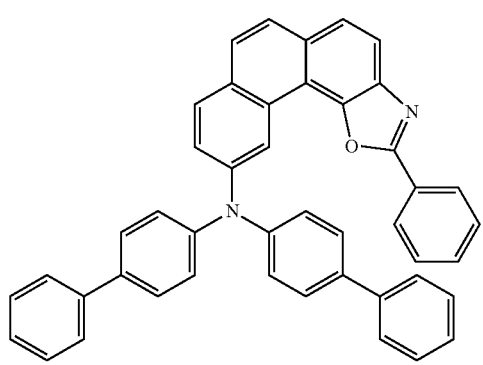
H1-86
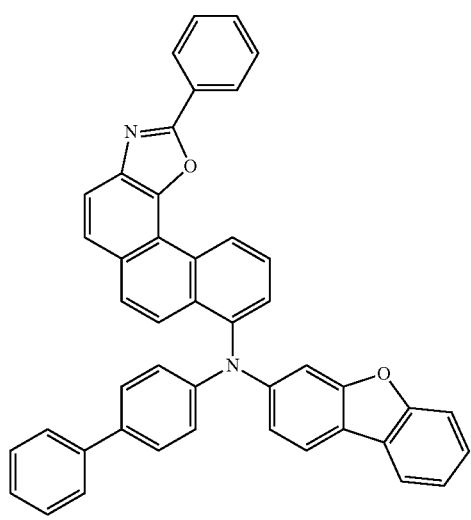
H1-87
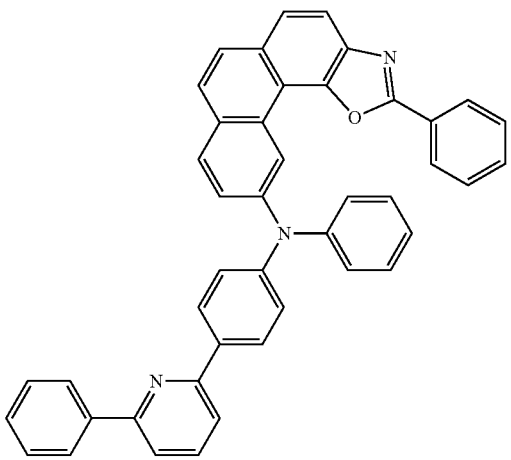
H1-88
H1-89
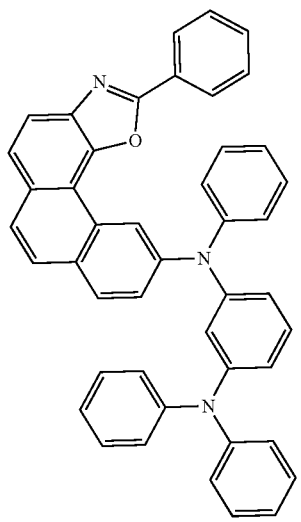

H1-90
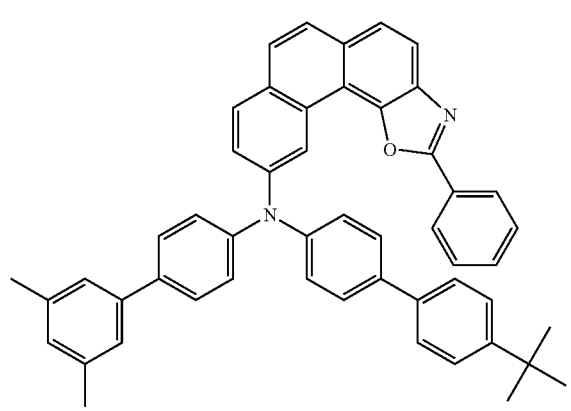
H1-91
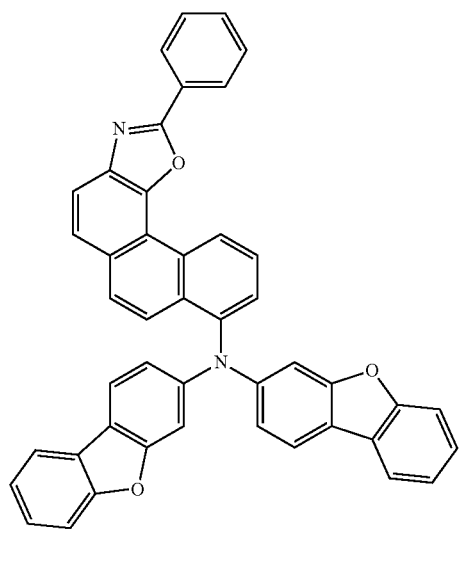
H1-92
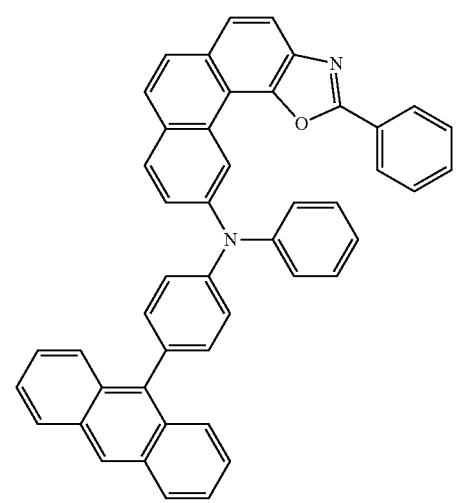
H1-93
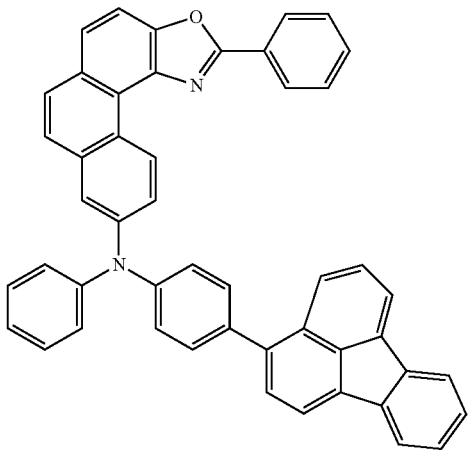
H1-94
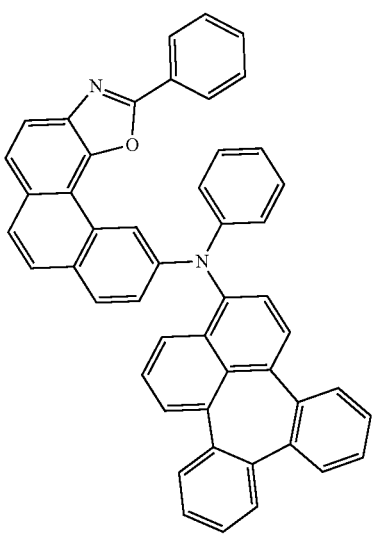
H1-95
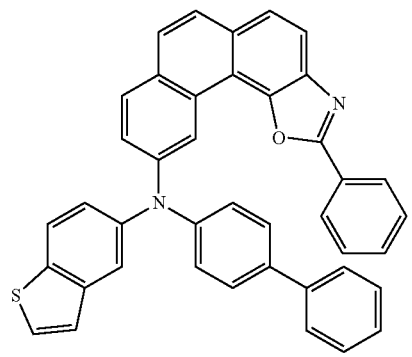

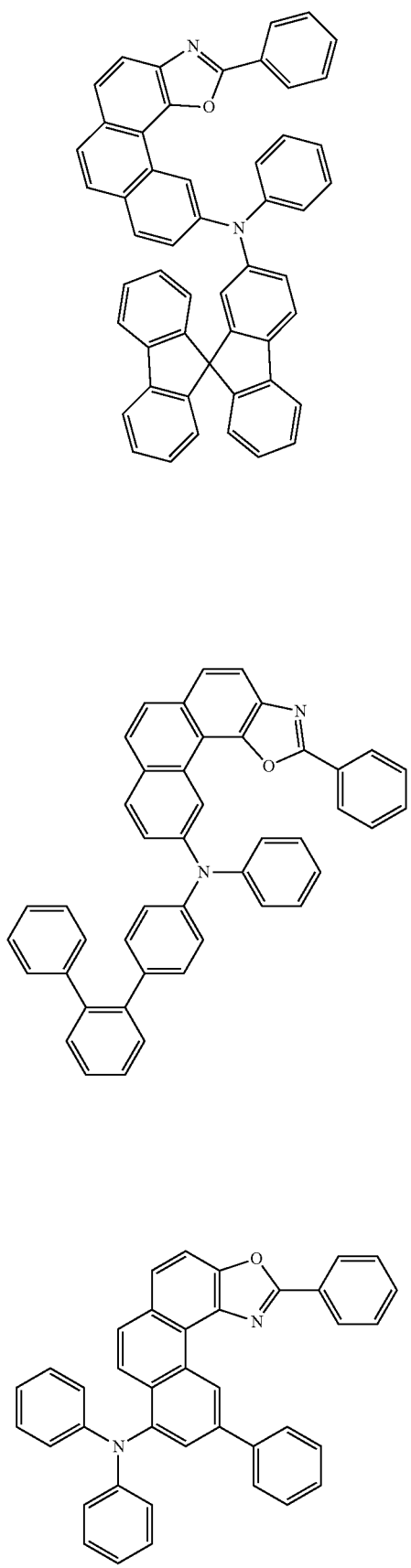
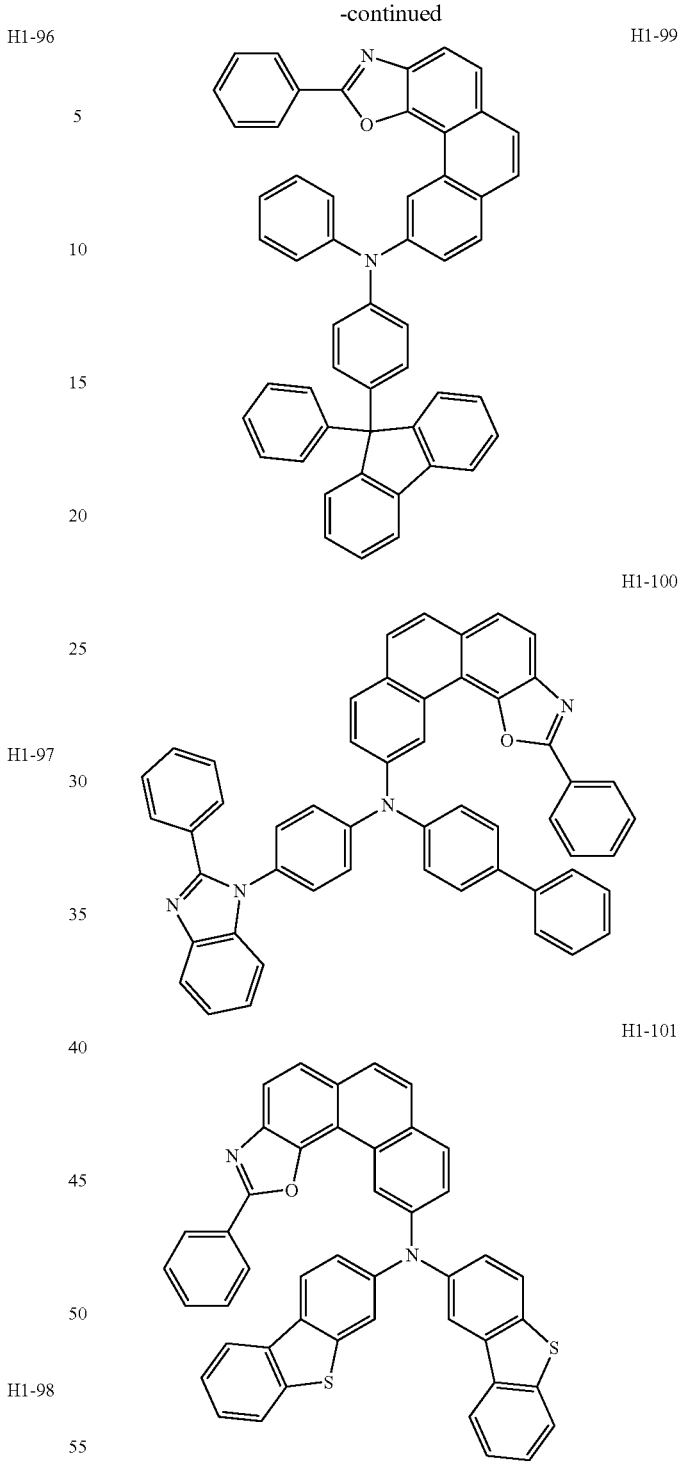

The combination of at least one of compounds C-1 to C-102 and at least one of compounds H1-1 to H1-101 may be used in an organic electroluminescent device.

The compound represented by formula 11 according to the present disclosure may be produced by a synthetic method known to one skilled in the art, and for example, by referring to Korean Patent Application Laying-Open No. 2017-0022865 (published on Mar. 2, 2017), and Korean Patent Application Laying-Open No. 2018-0099487 (published on Sep. 5, 2018), but is not limited thereto.

The dopant comprised in the organic electroluminescent device of the present disclosure may be at least one phosphorescent or fluorescent dopant, and is preferably phosphorescent dopant. The phosphorescent dopant material applied to the organic electroluminescent device of the present disclosure is not particularly limited, but may be preferably selected from the metallated complex compounds of iridium (Ir), osmium (Os), copper (Cu), and platinum (Pt), more preferably selected from ortho-metallated complex compounds of iridium (Ir), osmium (Os), copper (Cu), and platinum (Pt), and even more preferably ortho-metallated iridium complex compounds.

The dopant comprised in the organic electroluminescent device of the present disclosure may comprise a compound represented by the following formula 101, but is not limited thereto.

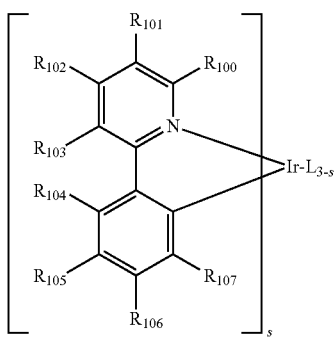

(101)

In formula 101,

L is selected from the following structures 1 to 3:

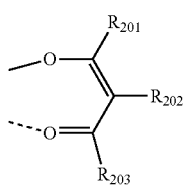

[Structure 1]

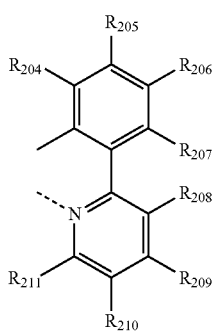

[Structure 2]

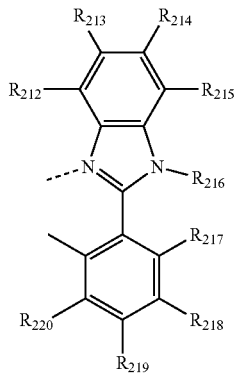

[Structure 3]

$R_{100}$ to $R_{103}$, each independently, represent hydrogen, deuterium, a halogen, a (C1-C30)alkyl unsubstituted or substituted with deuterium and/or a halogen(s), a substituted or unsubstituted (C3-C30)cycloalkyl, a substituted or unsubstituted (C6-C30)aryl, a cyano, a substituted or unsubstituted (3- to 30-membered)heteroaryl, or a substituted or unsubstituted (C1-C30)alkoxy; or adjacent ones of $R_{100}$ to $R_{103}$ may be linked to each other to form a ring(s), e.g., a substituted or unsubstituted, quinoline, benzofuropyridine, benzothienopyridine, indenopyridine, benzofuroquinoline, benzothienoquinoline, or indenoquinoline, together with pyridine;

$R_{104}$ to $R_{107}$, each independently, represent hydrogen, deuterium, a halogen, a (C1-C30)alkyl unsubstituted or substituted with deuterium and/or a halogen(s), a substituted or unsubstituted (C3-C30)cycloalkyl, a substituted or unsubstituted (C6-C30)aryl, a substituted or unsubstituted (3- to 30-membered)heteroaryl, a cyano, or a substituted or unsubstituted (C1-C30)alkoxy; or adjacent ones of $R_{104}$ to $R_{107}$ may be linked to each other to form a ring(s), e.g., a substituted or unsubstituted, naphthalene, fluorene, dibenzothiophene, dibenzofuran, indenopyridine, benzofuropyridine, or benzothienopyridine, together with benzene;

$R_{201}$ to $R_{220}$, each independently, represent hydrogen, deuterium, a halogen, a (C1-C30)alkyl unsubstituted or substituted with deuterium and/or a halogen(s), a substituted or unsubstituted (C3-C30)cycloalkyl, or a substituted or unsubstituted (C6-C30)aryl; or adjacent ones of $R_{201}$ to $R_{220}$ may be linked to each other to form a substituted or unsubstituted ring(s); and s represents an integer of 1 to 3.

The specific examples of the dopant compound are as follows, but are not limited thereto.
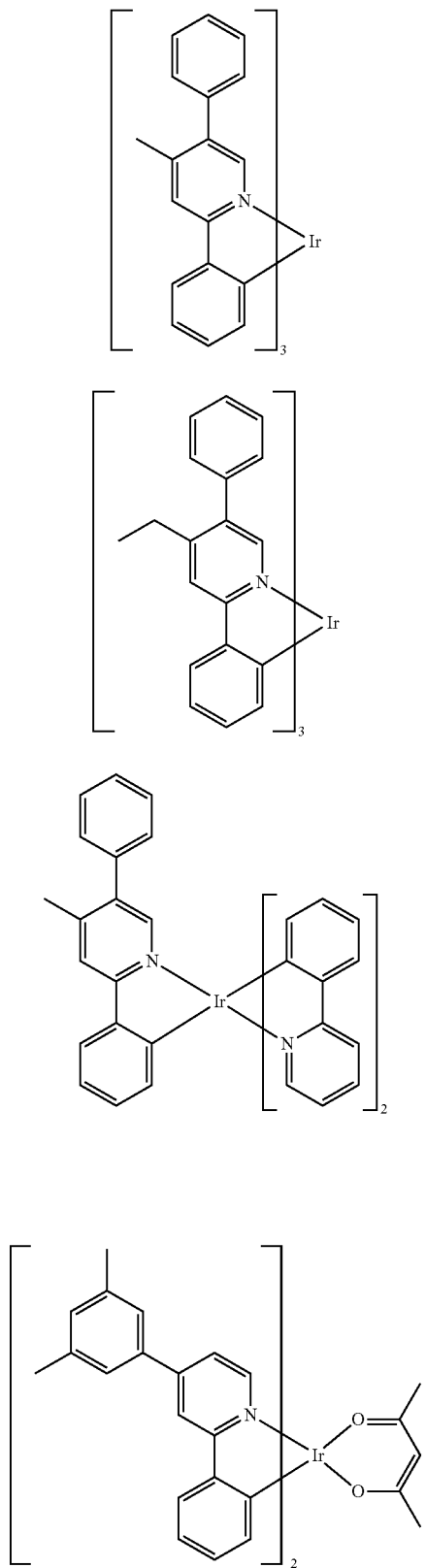
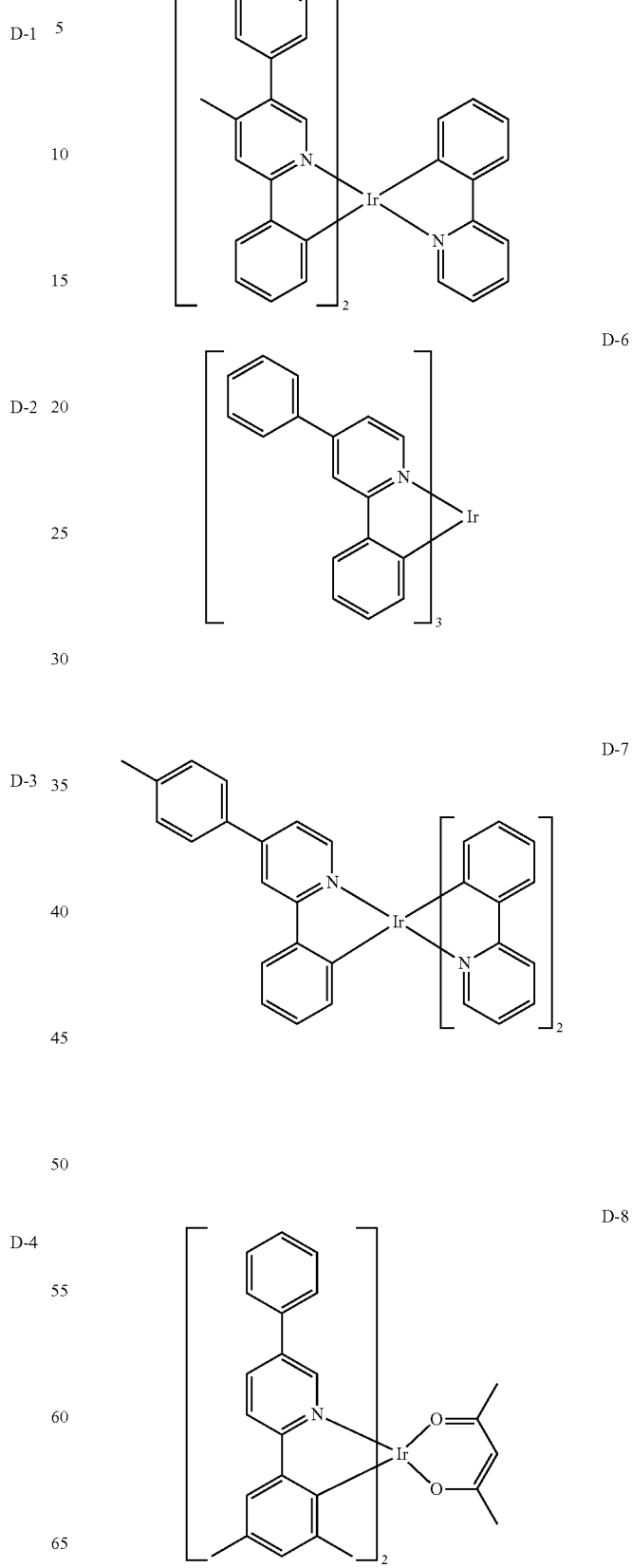

D-9
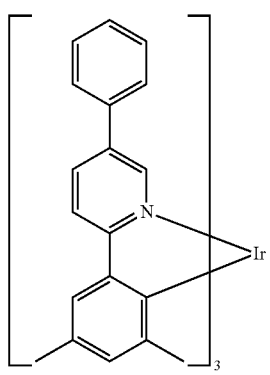
D-10
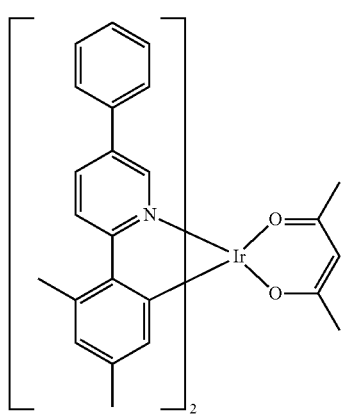
D-11
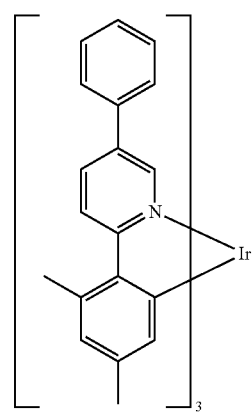
D-12
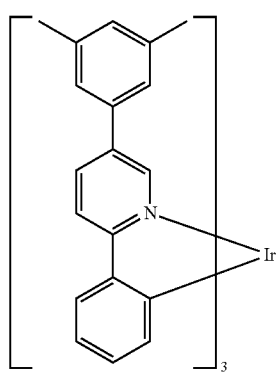
D-13
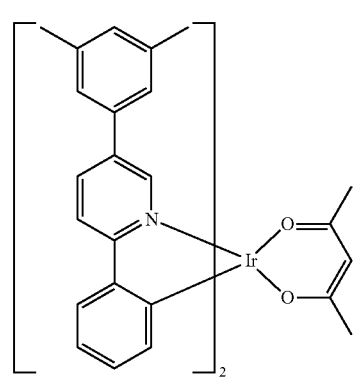
D-14
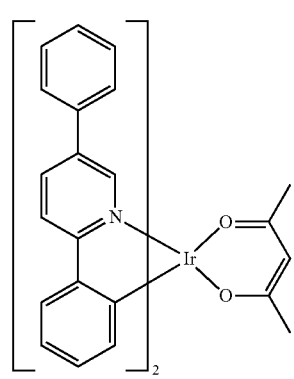
D-15
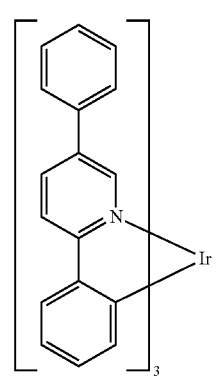
D-16
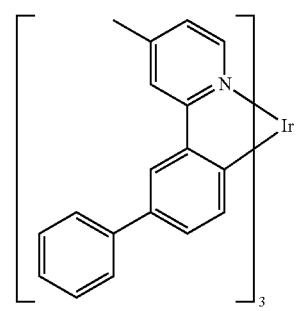

D-17
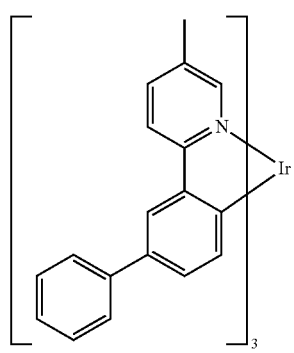
D-18
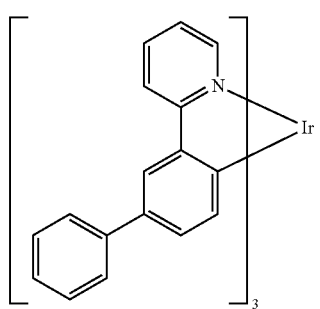
D-19
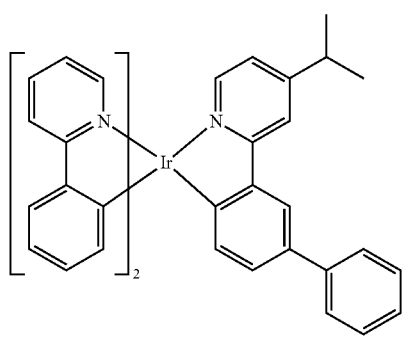
D-20
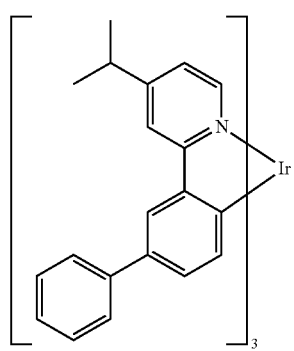
D-21
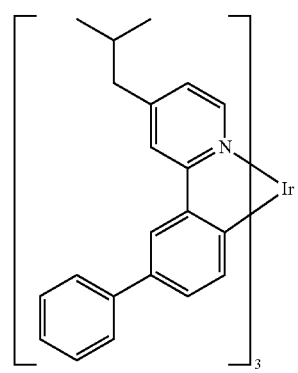
D-22
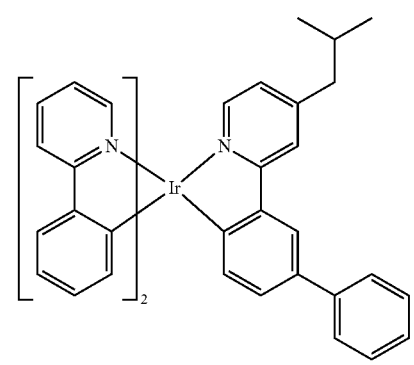
D-23
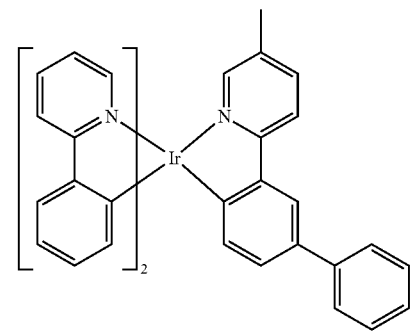
D-24
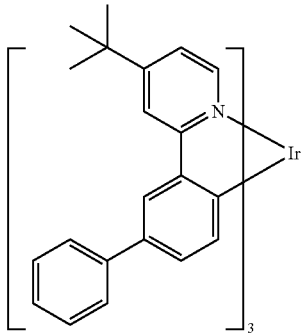

D-25
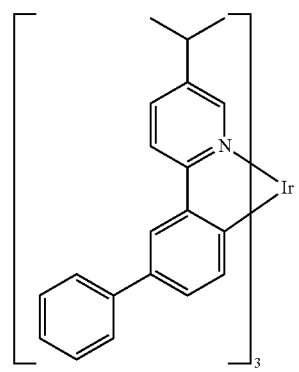
D-26
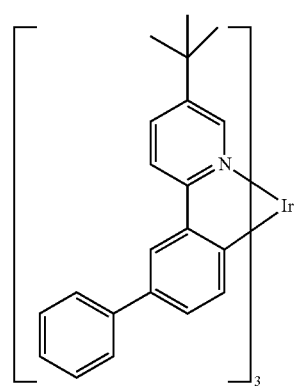
D-27
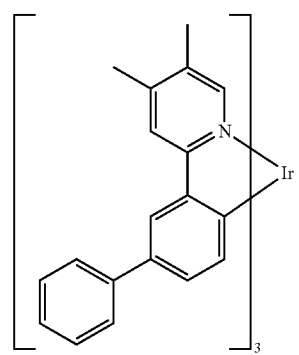
D-28
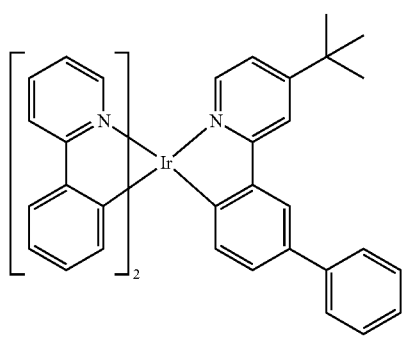
D-29
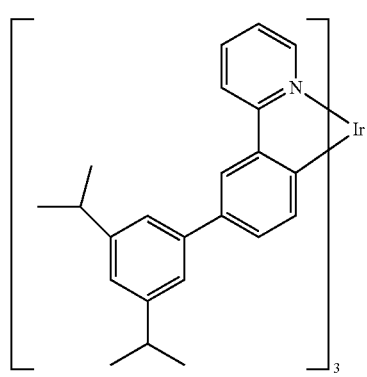
D-30
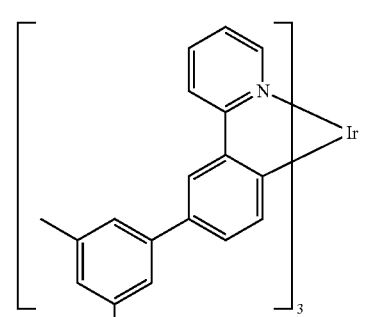
D-31
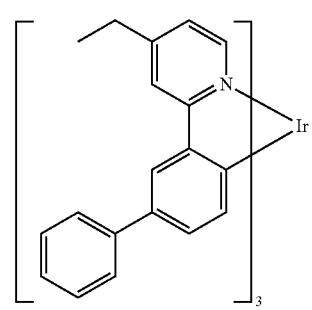
D-32
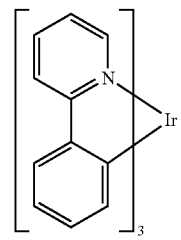
D-33
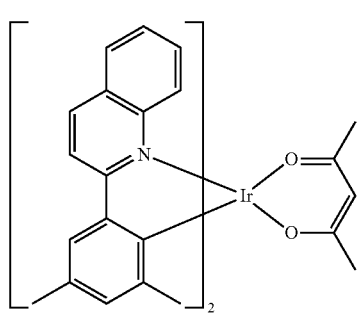

D-34
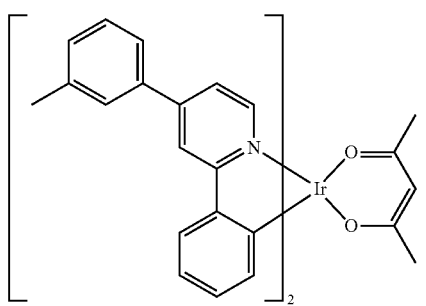
D-35
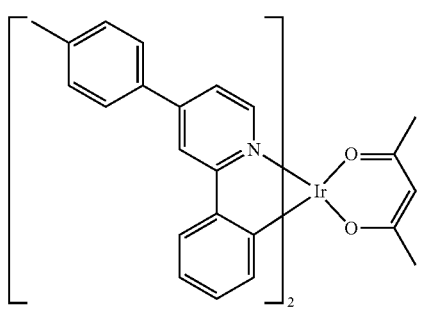
D-36
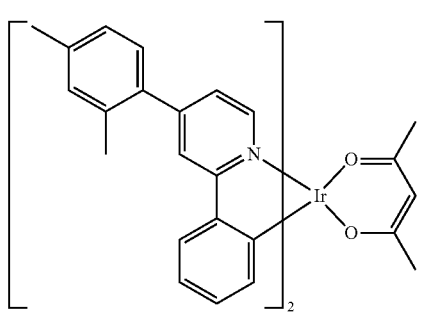
D-37
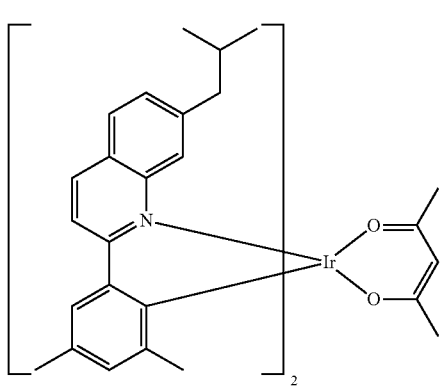
D-38
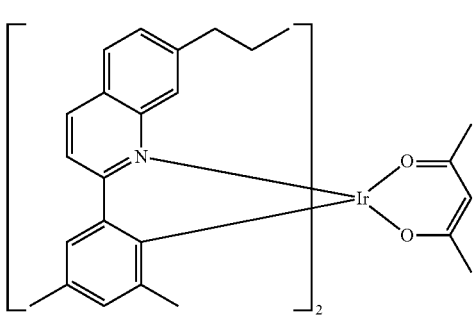
D-39
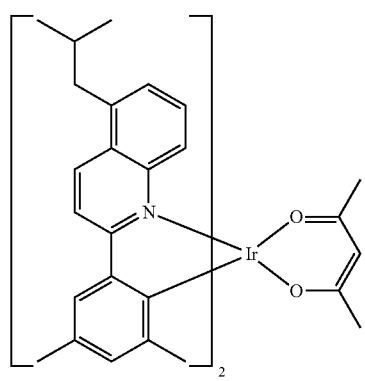
D-40
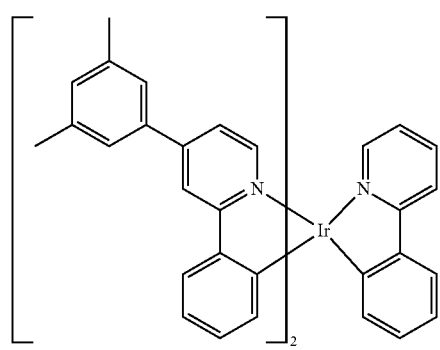
D-41
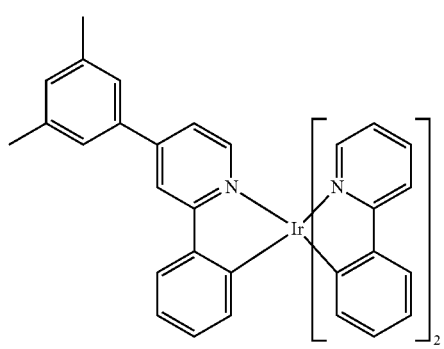
D-42
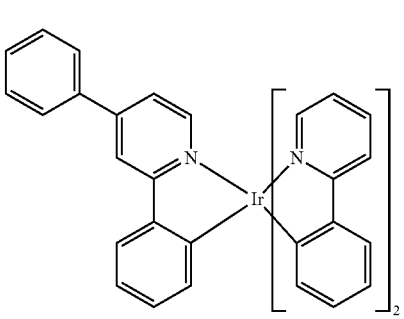

-continued
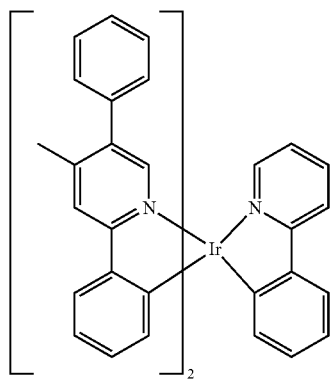
D-43
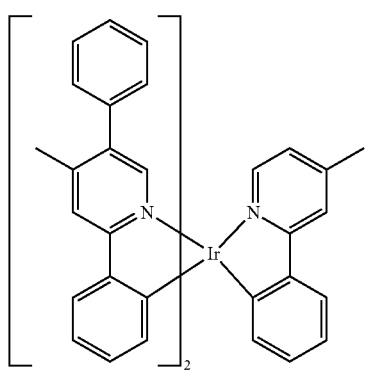
D-44
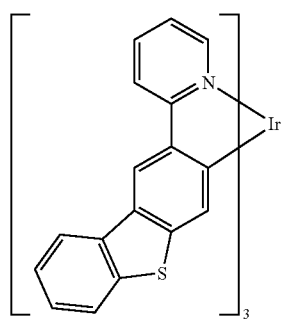
D-45
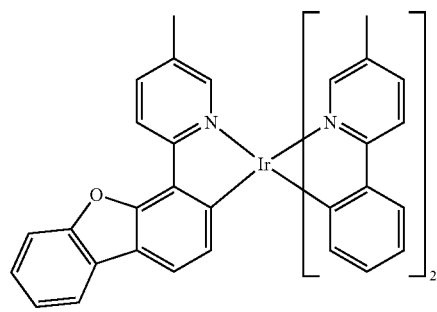
D-46
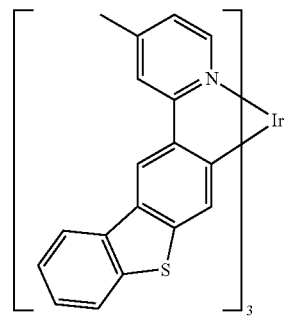
D-47
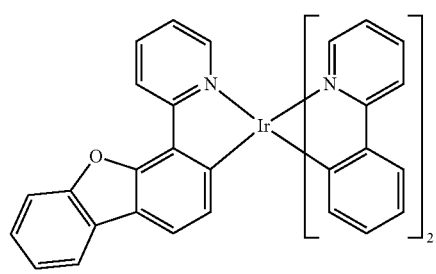
D-48
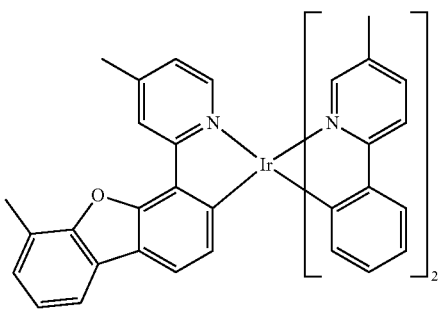
D-49
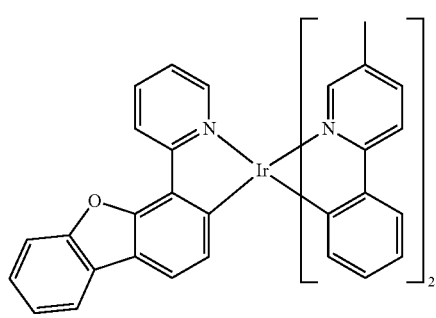
D-50
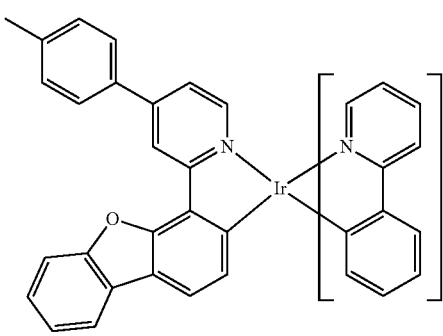
D-51

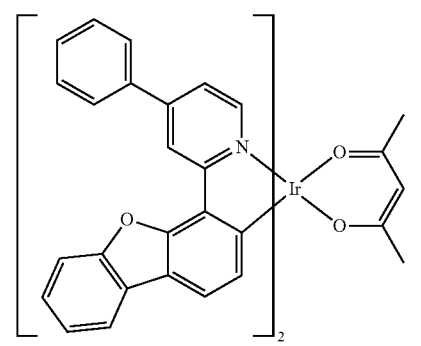 D-52
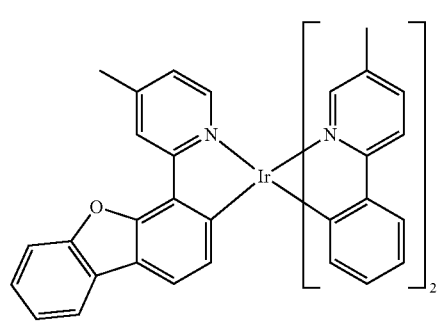 D-53
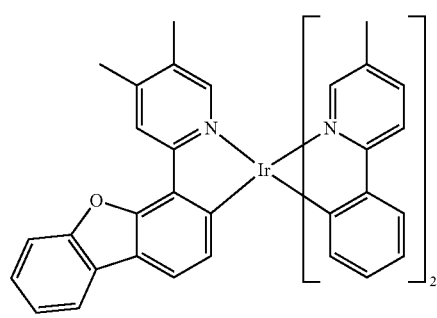 D-54
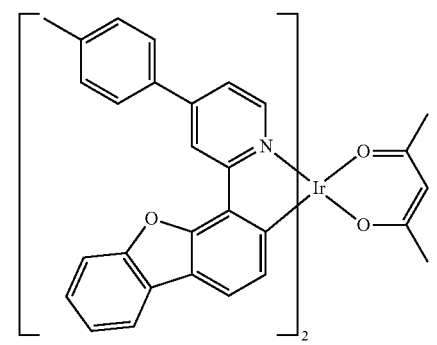 D-55
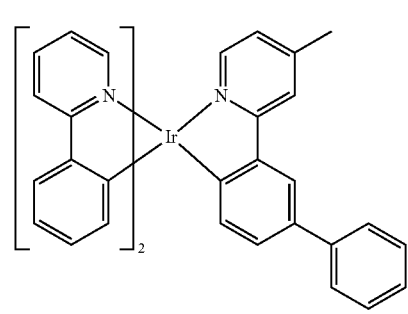 D-56
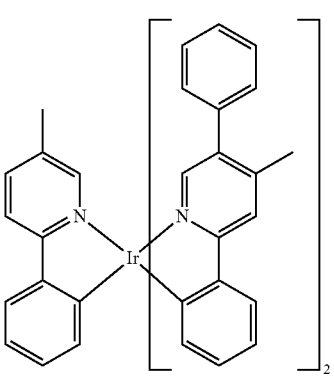 D-57
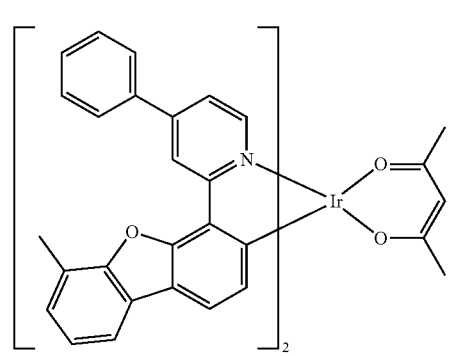 D-58
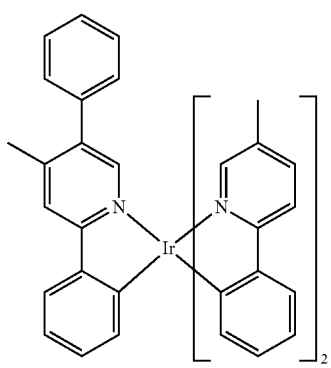 D-59
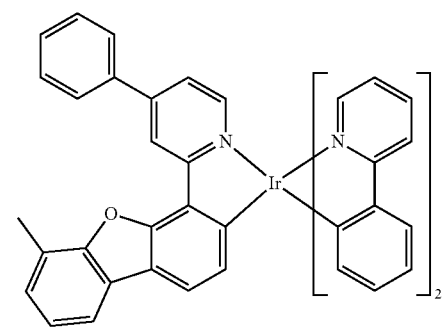 D-60

D-61
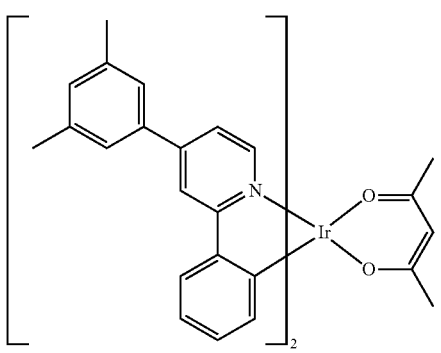
D-62
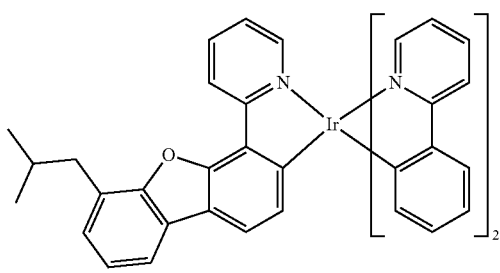
D-63
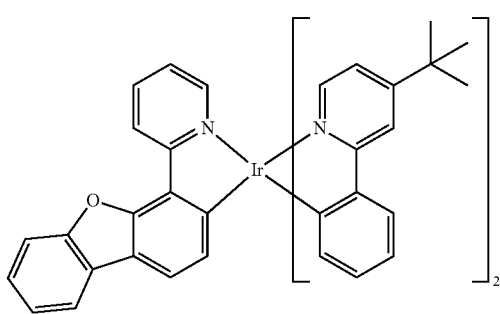
D-64
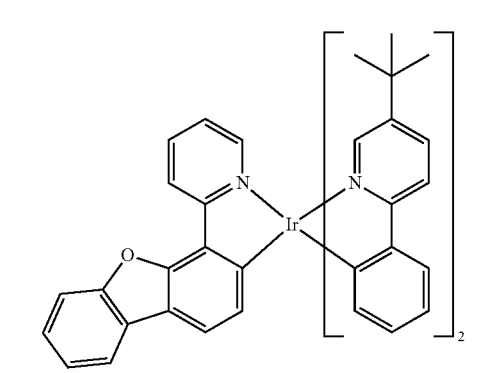
D-65
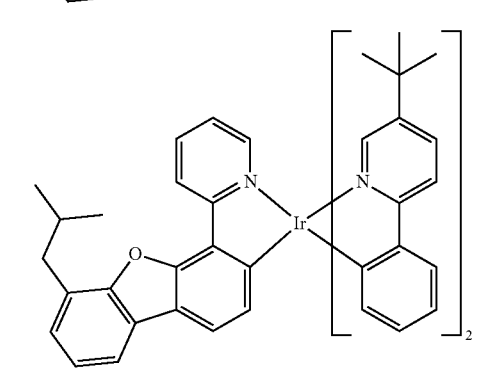
D-66
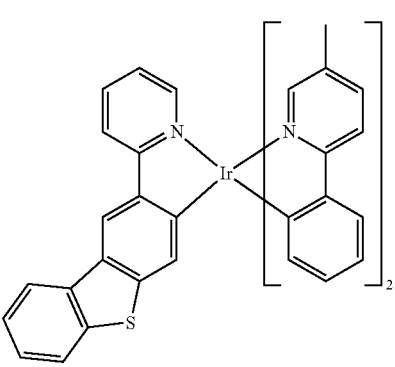
D-67
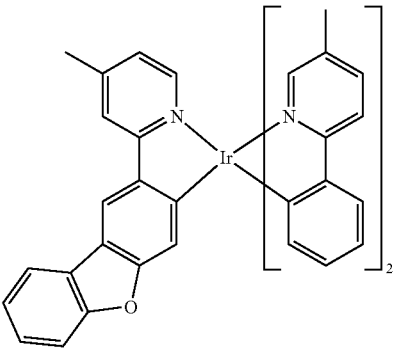
D-68
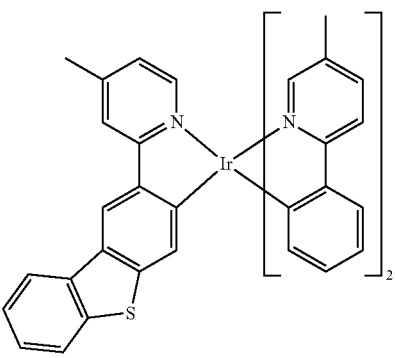
D-69
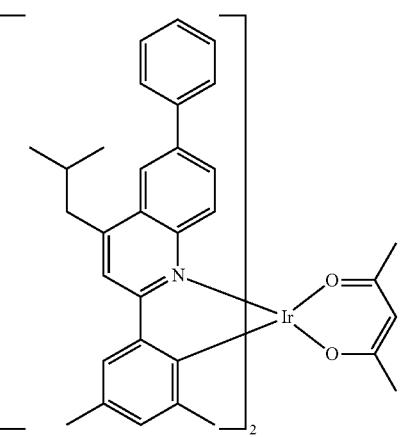

D-70
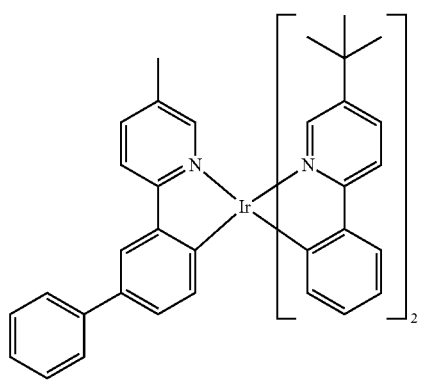
D-71
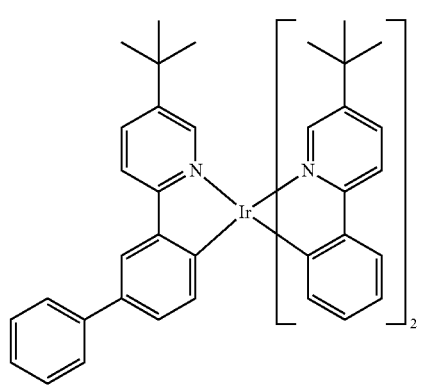
D-72
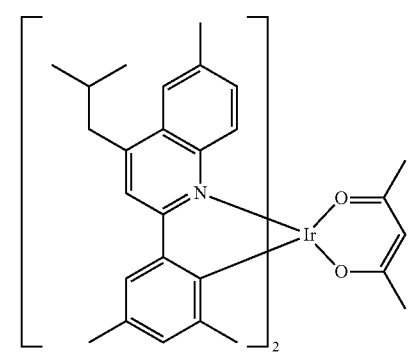
D-73
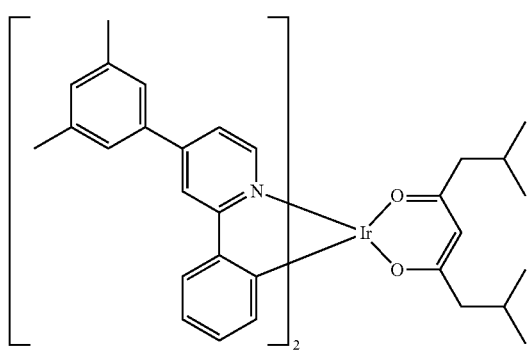
D-74
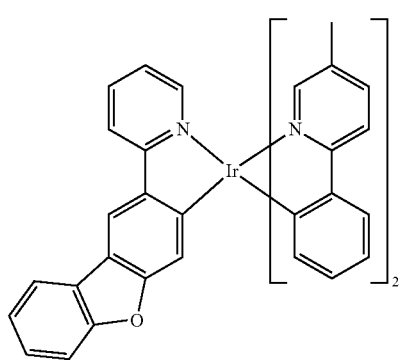
D-75
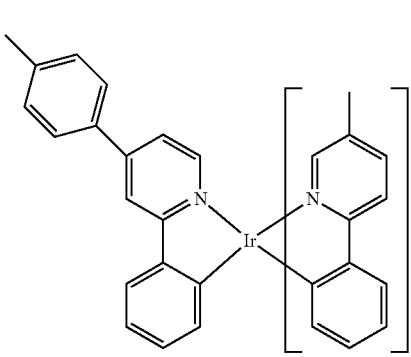
D-76
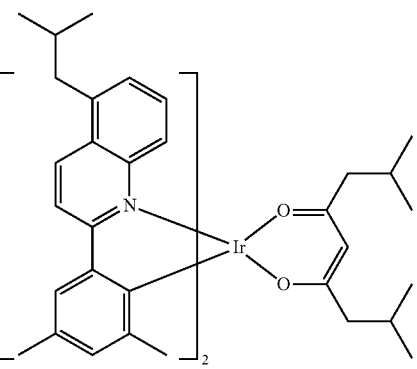
D-77
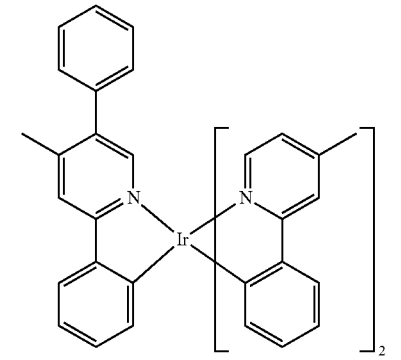

D-78
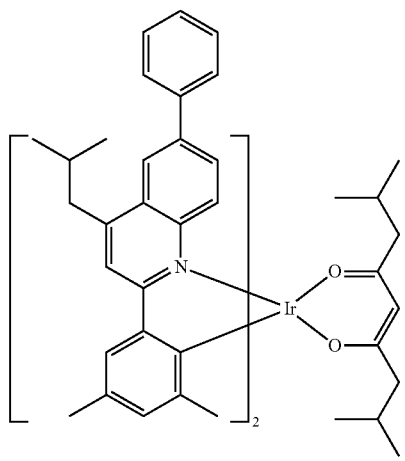
D-79
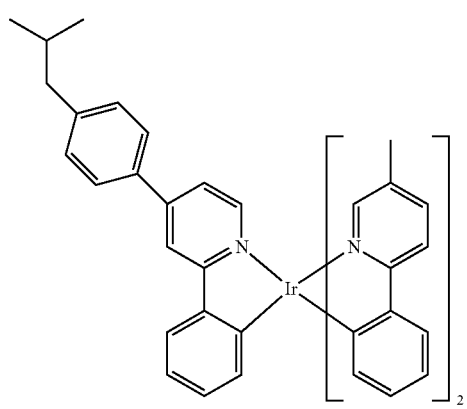
D-80
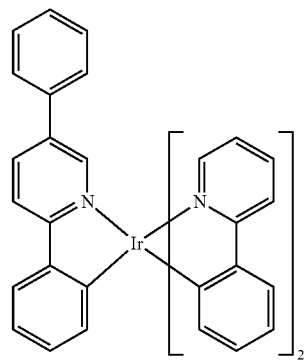
D-81
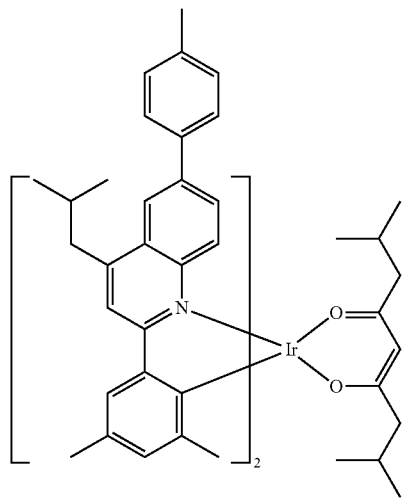
D-82
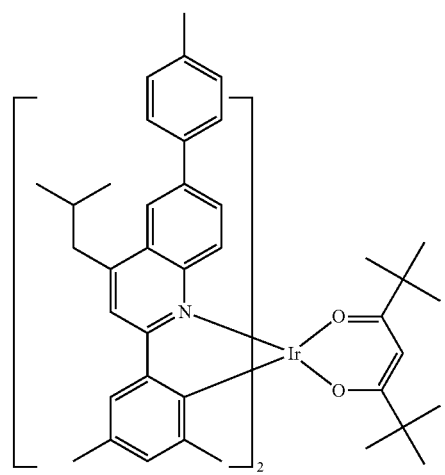
D-83

-continued
D-84
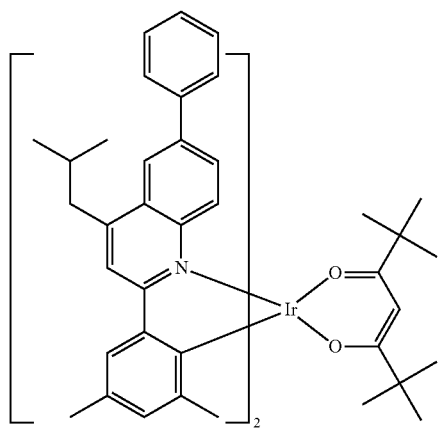
D-85
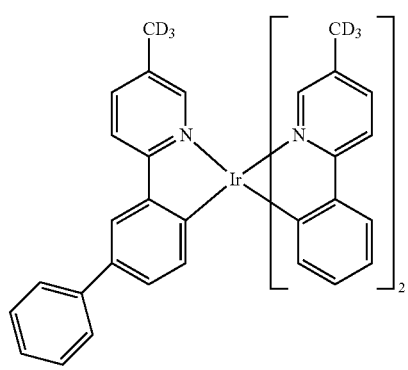
D-86
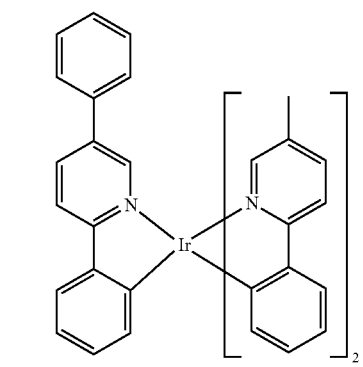
D-87
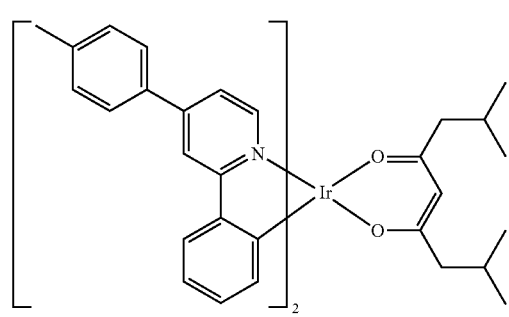
-continued
D-88
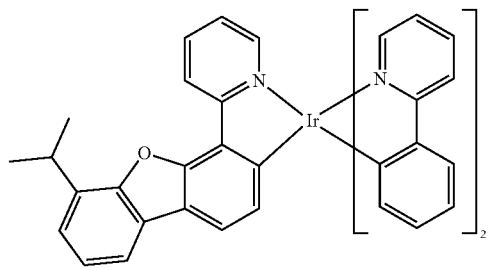
D-89
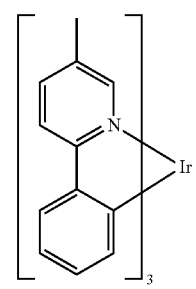
D-90
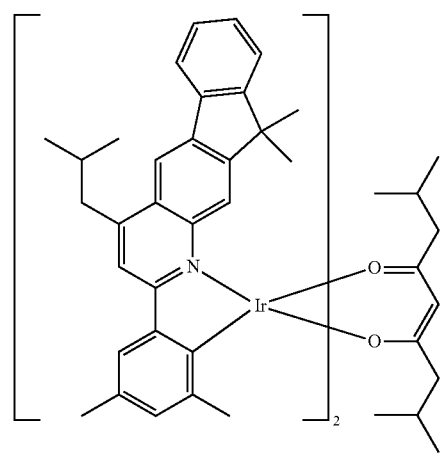
D-91
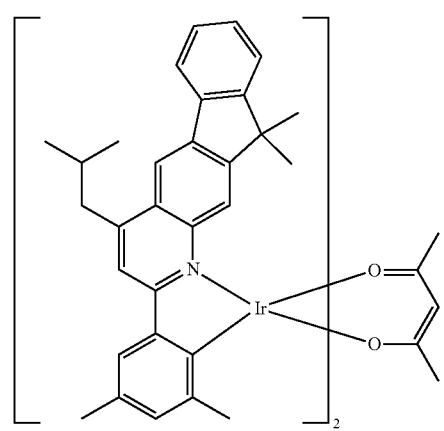

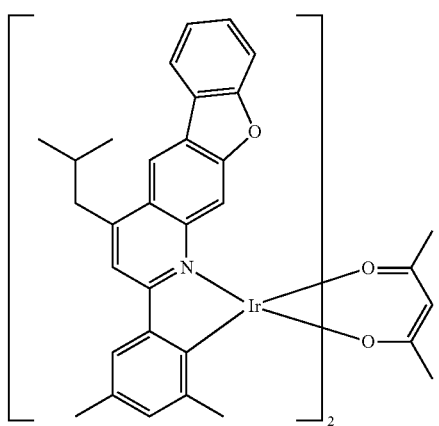
D-92
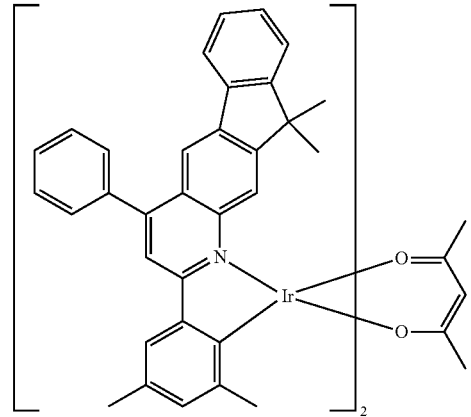
D-95
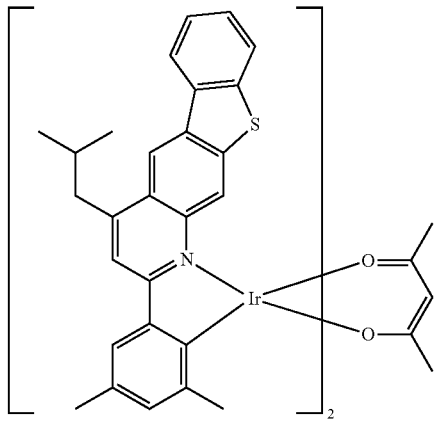
D-93
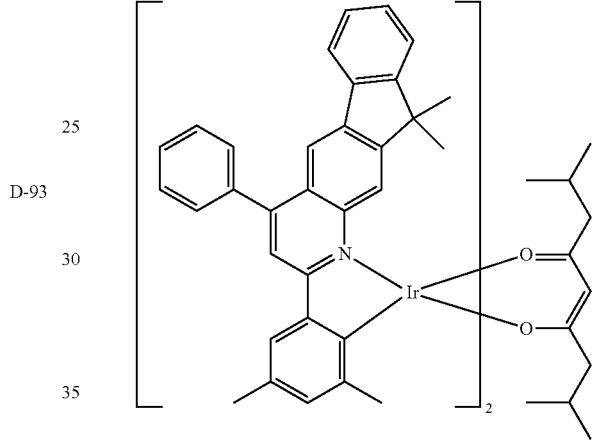
D-96
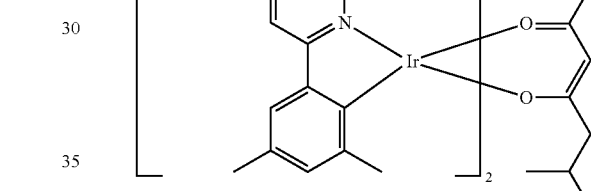
D-94
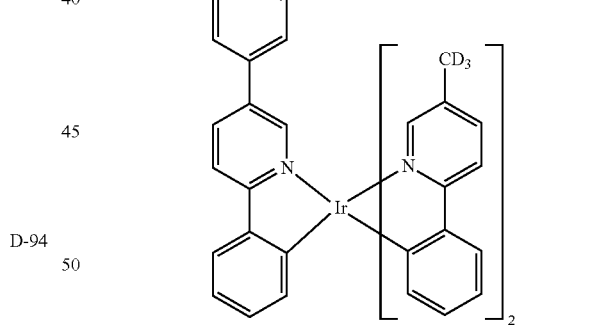
D-97
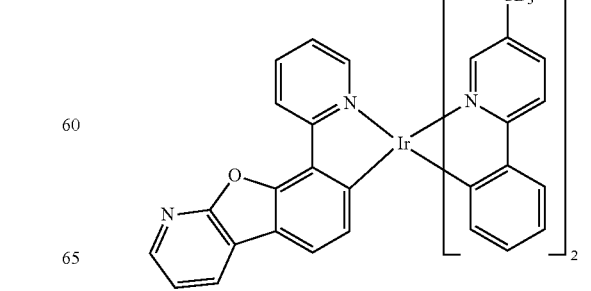
D-98

-continued
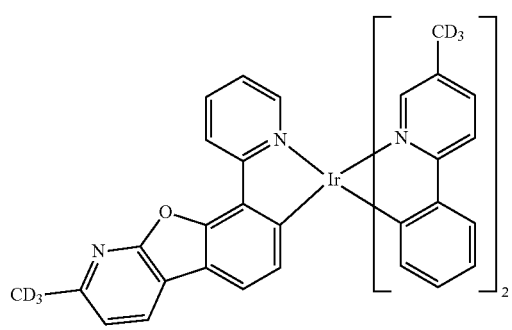
D-99
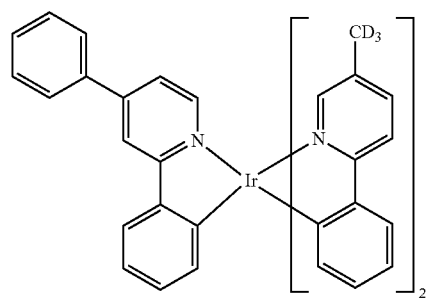
D-100
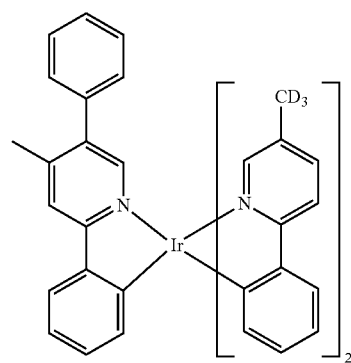
D-101
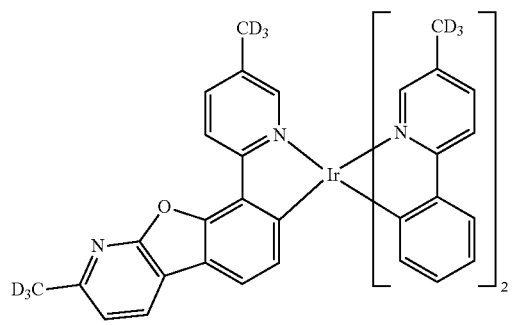
D-102
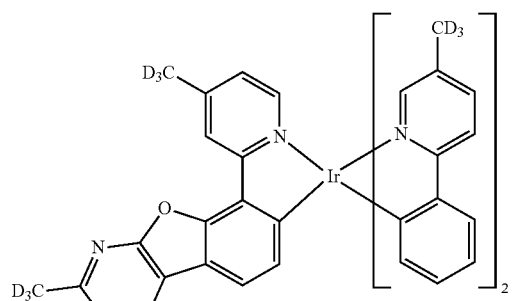
D-103
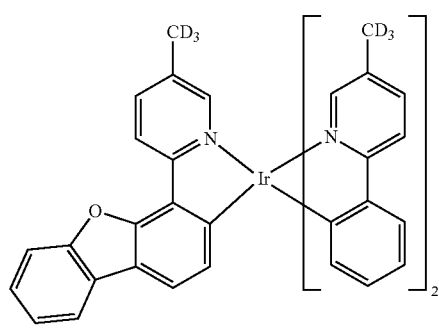
D-104
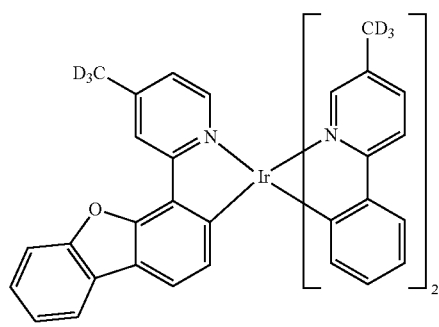
D-105
D-106

-continued
D-107
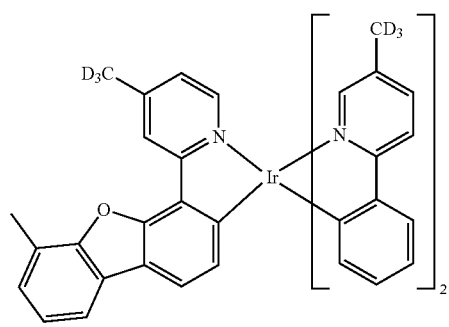
D-108
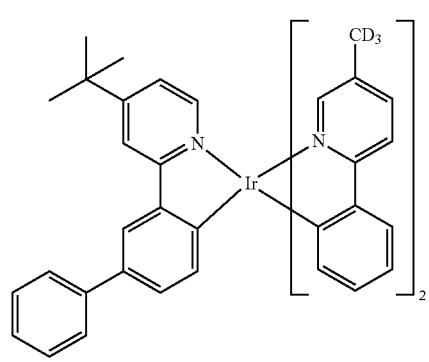
D-109
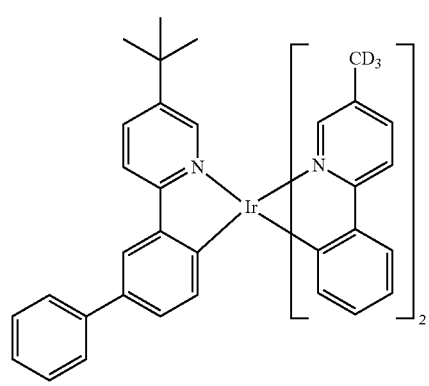
D-110
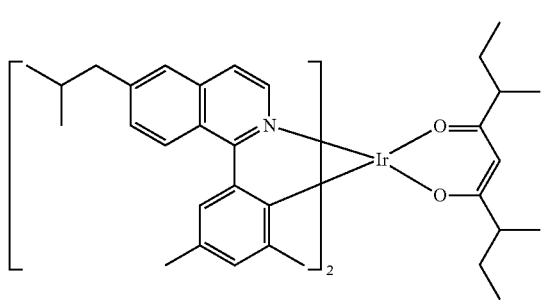
-continued
D-111
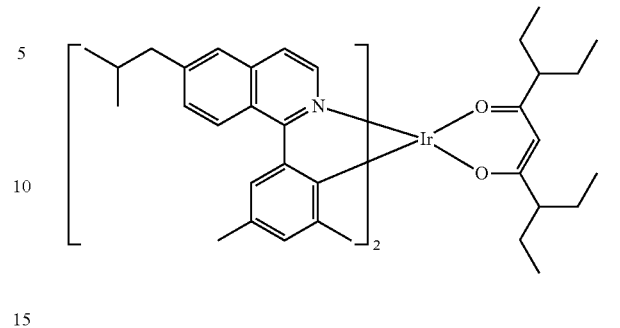
D-112
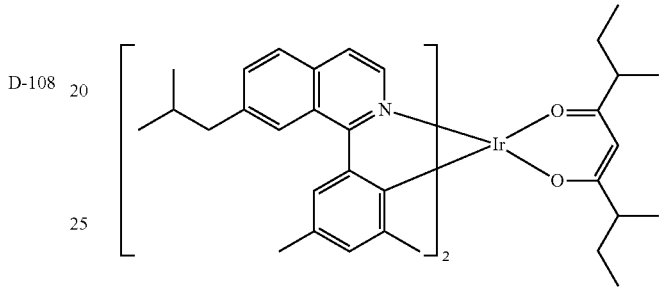
D-113
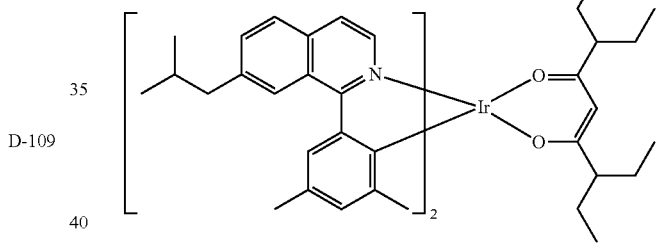
D-114
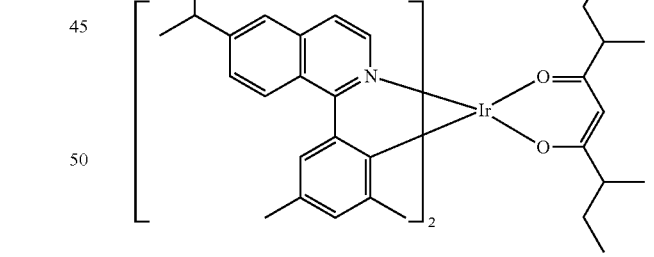
D-115
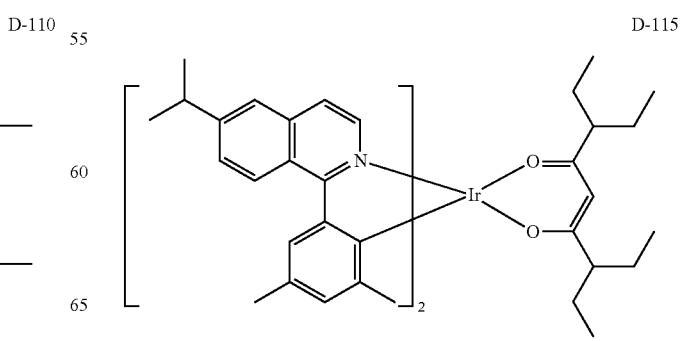

D-116
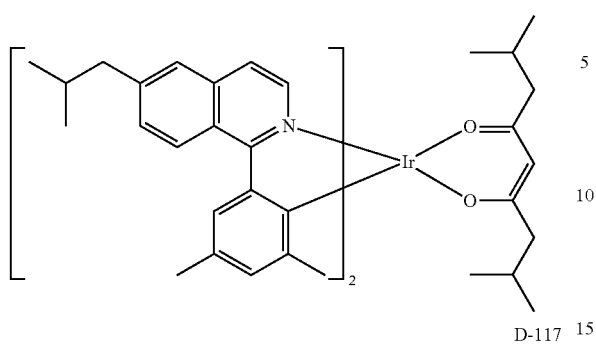
D-117
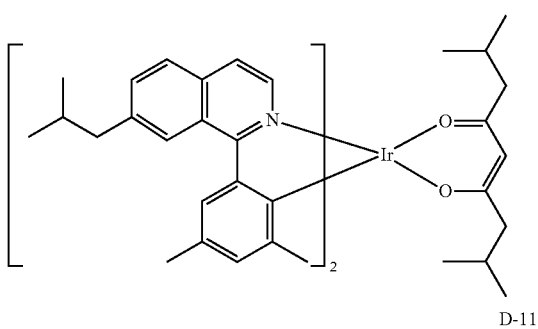
D-118
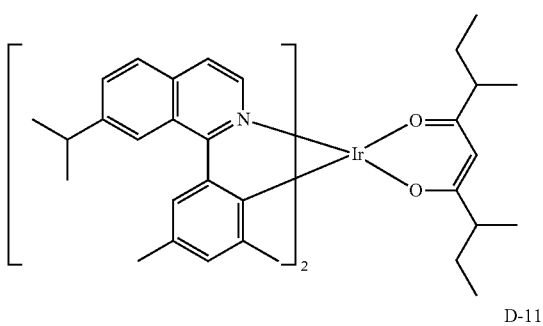
D-119
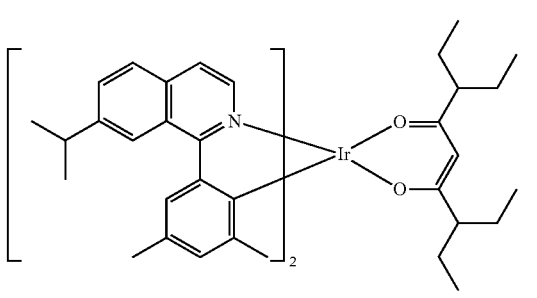
D-120
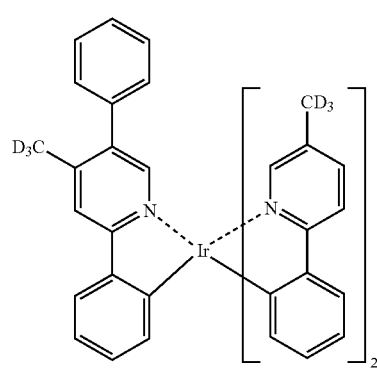
D-121
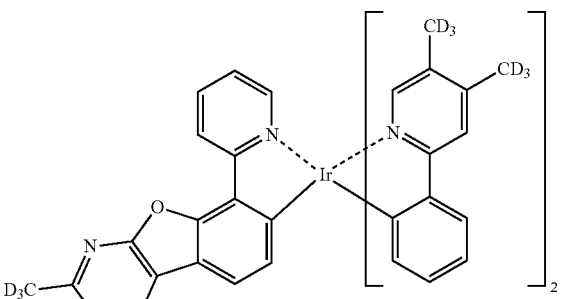
D-122
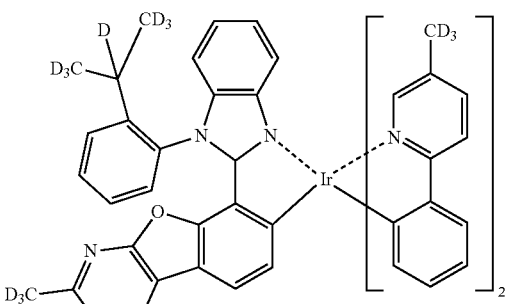
D-123
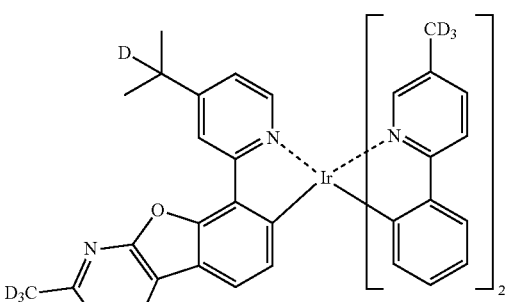
D-124
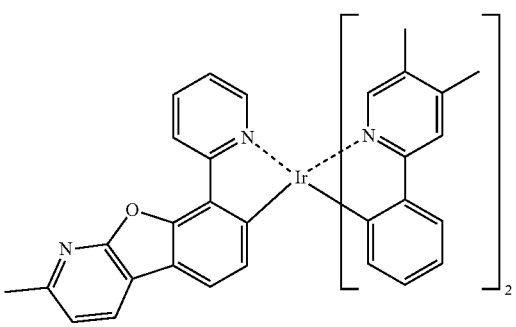

D-125
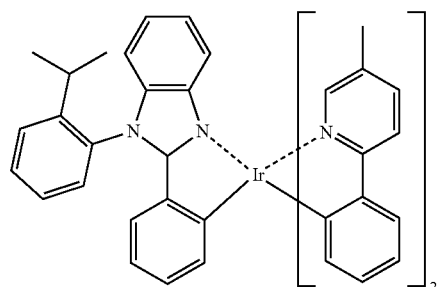
D-126
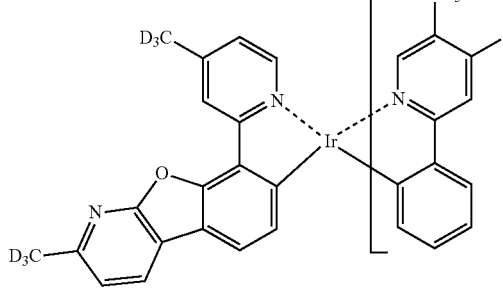
D-127
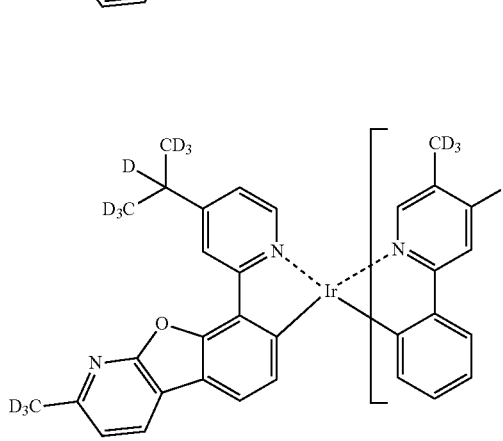
D-128
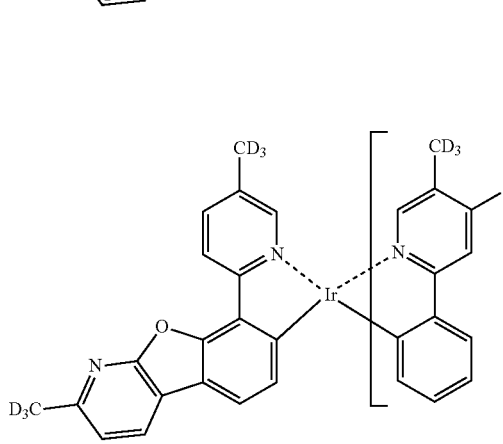
D-129
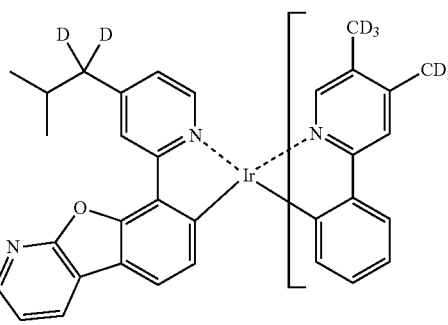
D-130
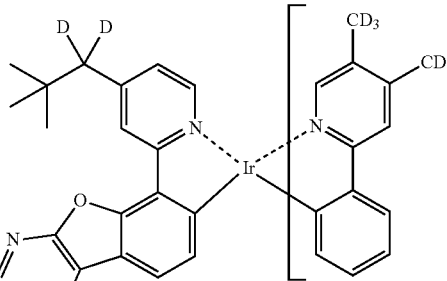
D-131
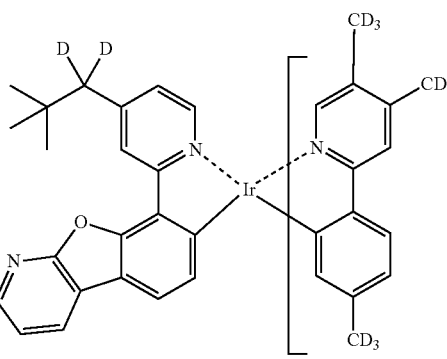
D-132
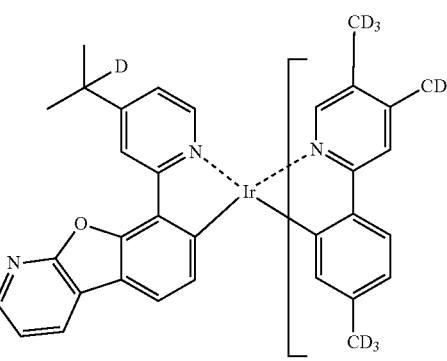

D-133
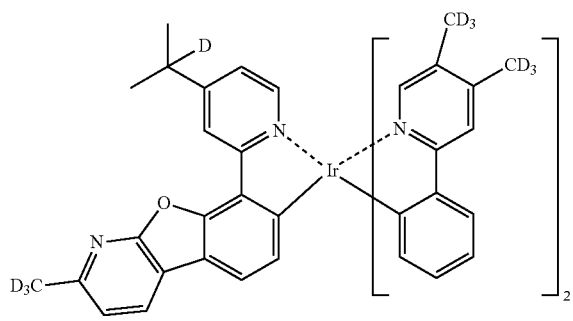
D-134
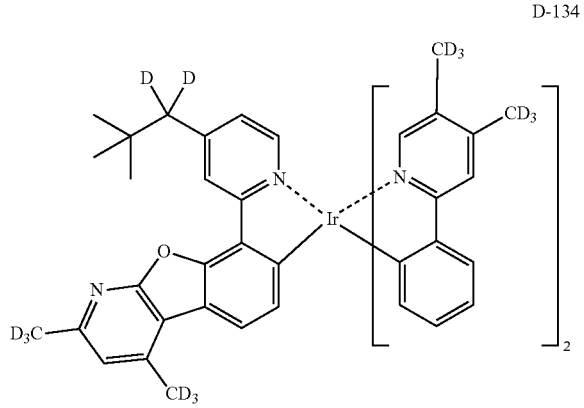
D-135
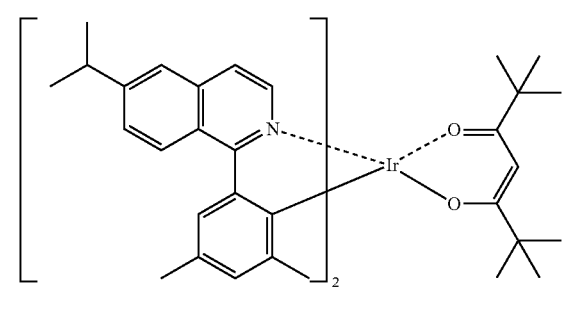
D-136
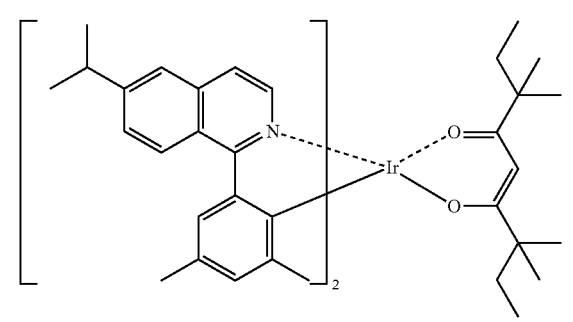
D-137
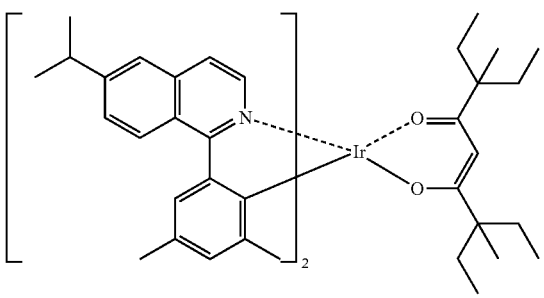
D-138
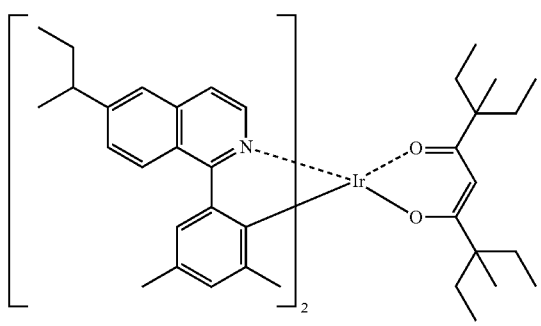
D-139
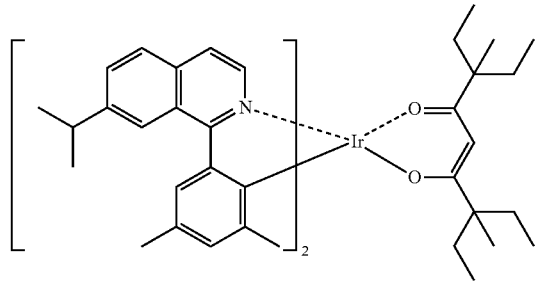
D-140
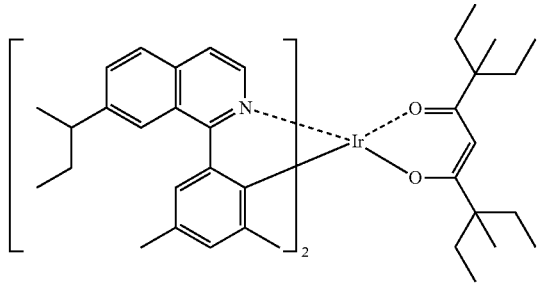
D-141
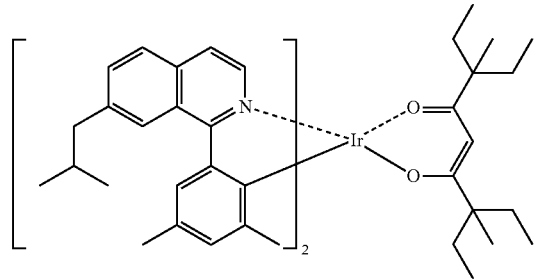

D-142
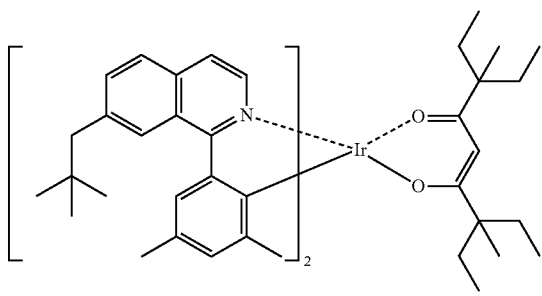
D-143
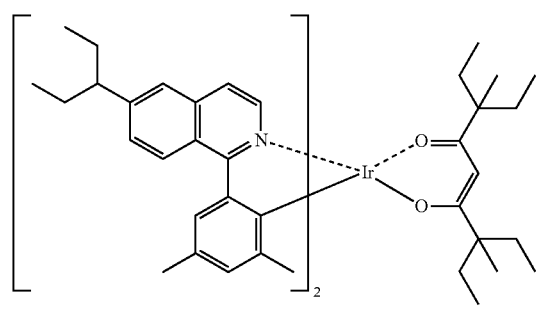
D-144
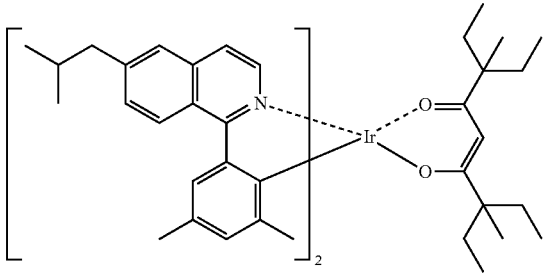
D-145
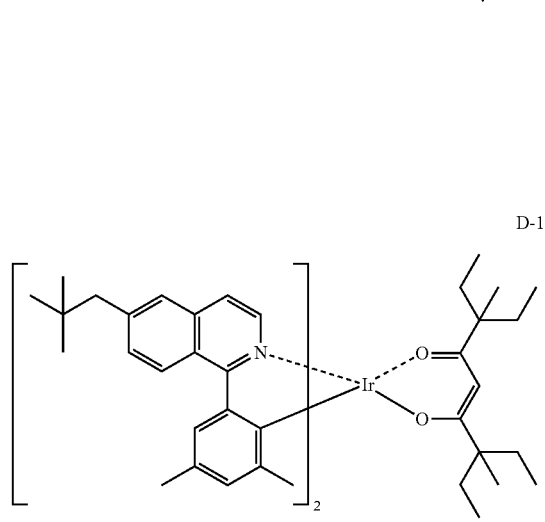
D-146
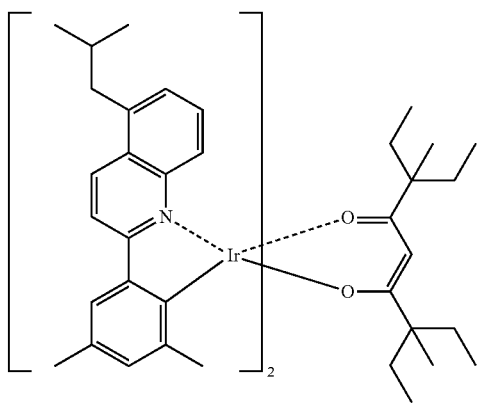
D-147
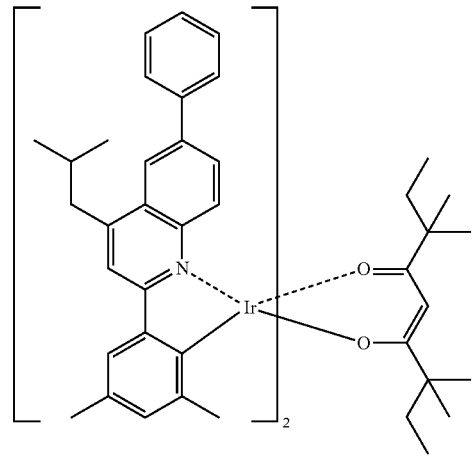
D-148

D-149

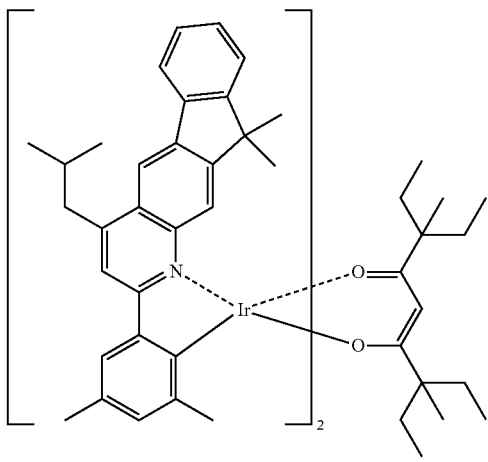

An organic electroluminescent device according to the present disclosure has a first electrode, a second electrode, and at least one organic layer between the first electrode and the second electrode.

One of the first and second electrodes may be an anode, and the other may be a cathode. The organic layer comprises a light-emitting layer and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer. Each of the layers may be further configured as a plurality of layers.

The first and second electrodes may be respectively formed with a transparent conductive material, or a transflective or reflective conductive material. The organic electroluminescent device may be a top emission type, a bottom emission type, or a both-sides emission type, depending on the materials forming the first and second electrodes. In addition, the hole injection layer may be further doped with a p-dopant, and the electron injection layer may be further doped with an n-dopant.

The organic layer may further comprise at least one compound selected from the group consisting of arylamine-based compounds and styrylarylamine-based compounds.

Further, in the organic electroluminescent device of the present disclosure, the organic layer may further comprise at least one metal selected from the group consisting of metals of Group 1, metals of Group 2, transition metals of the 4$^{th}$ period, transition metals of the 5$^{th}$ period, lanthanides, and organic metals of the d-transition elements of the Periodic Table, or at least one complex compound comprising the metal.

In addition, the organic electroluminescent device of the present disclosure may emit white light by further comprising at least one light-emitting layer, which comprises a blue, a red, or a green electroluminescent compound known in the field, besides the compound of the present disclosure. If necessary, it may further comprise a yellow or an orange light-emitting layer.

In the organic electroluminescent device of the present disclosure, preferably, at least one layer selected from a chalcogenide layer, a metal halide layer, and a metal oxide layer (hereinafter, "a surface layer") may be placed on an inner surface(s) of one or both electrode(s). Specifically, a chalcogenide (including oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, the chalcogenide includes $SiO_x$ ($1 \leq X \leq 2$), $AlO_x$ ($1.5 \leq X \leq 1.5$), SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

A hole injection layer, a hole transport layer, an electron blocking layer, or a combination thereof can be used between the anode and the light-emitting layer. The hole injection layer may be multi-layers in order to lower the hole injection barrier (or hole injection voltage) from the anode to the hole transport layer or the electron blocking layer, wherein each of the multi-layers may use two compounds simultaneously. The hole transport layer or the electron blocking layer may also be multi-layers.

An electron buffer layer, a hole blocking layer, an electron transport layer, an electron injection layer, or a combination thereof can be used between the light-emitting layer and the cathode. The electron buffer layer may be multi-layers in order to control the injection of the electron and improve the interfacial properties between the light-emitting layer and the electron injection layer, wherein each of the multi-layers may use two compounds simultaneously. The hole blocking layer or the electron transport layer may also be multi-layers, wherein each of the multi-layers may use a plurality of compounds.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or hole transport, or for preventing the overflow of electrons. When the light-emitting auxiliary layer is placed between the cathode and the light-emitting layer, it can be used for promoting the electron injection and/or electron transport, or for preventing the overflow of holes. Also, the hole auxiliary layer may be placed between the hole transport layer (or hole injection layer) and the light-emitting layer, and may be effective to promote or block the hole transport rate (or hole injection rate), thereby enabling the charge balance to be controlled. Further, the electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. When an organic electroluminescent device includes two or more hole transport layers, the hole transport layer, which is further included, may be used as a hole auxiliary layer or an electron blocking layer. The light-emitting auxiliary layer, the hole auxiliary layer or the electron blocking layer may have an effect of improving the efficiency and/or the lifetime of the organic electroluminescent device.

Preferably, in the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to the light-emitting medium. Furthermore, the hole transport compound is oxidized to a cation, and thus it becomes easier to inject and transport holes from the mixed region to the light-emitting medium. Preferably, the oxidative dopant includes various Lewis acids and acceptor compounds; and the reductive dopant includes alkali metals, alkali metal compounds, alkaline earth metals, rare-earth metals, and mixtures thereof. The reductive dopant layer may be employed as a charge-generating layer to prepare an organic electroluminescent device having two or more light-emitting layers and emitting white light.

The organic electroluminescent material according to the present disclosure may be used as a light-emitting material for a white organic light-emitting device. The white organic light-emitting device has been suggested to have various structures such as a side-by-side structure or a stacking structure depending on the arrangement of R (red), G (green) or YG (yellow green), and B (blue) light-emitting parts, or color conversion material (CCM) method, etc. The organic electroluminescent material according to the present disclosure may also be used in an organic electroluminescent device comprising a quantum dot (QD).

In order to form each layer of the organic electroluminescent device of the present disclosure, dry film-forming methods such as vacuum evaporation, sputtering, plasma, ion plating methods, etc., or wet film-forming methods such as ink jet printing, nozzle printing, slot coating, spin coating, dip coating, flow coating methods, etc., can be used. When the first and second host compounds of the present disclosure are used to form a film, a co-evaporation process or a mixture-evaporation process is carried out.

When using a wet film-forming method, a thin film can be formed by dissolving or diffusing materials forming each layer into any suitable solvent such as ethanol, chloroform, tetrahydrofuran, dioxane, etc. The solvent can be any one where the materials forming each layer can be dissolved or diffused, and where there are no problems in film-formation capability.

In addition, it is possible to produce a display system, for example, a display system for smart phones, tablets, notebooks, PCs, TVs, or cars; or a lighting system, for example an outdoor or indoor lighting system, by using the organic electroluminescent device of the present disclosure.

Hereinafter, the preparation method of the compounds according to the present disclosure and the properties thereof will be explained in detail with reference to the representative compounds of the present disclosure. However, the present disclosure is not limited by the following examples.

Example 1: Preparation of Compound C-43

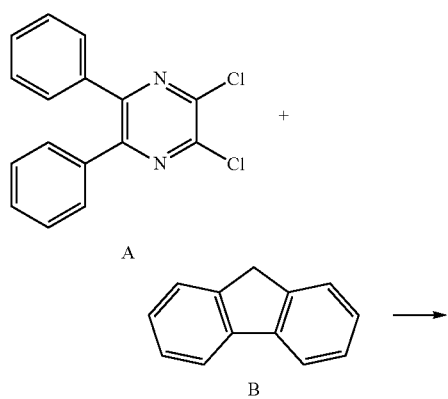

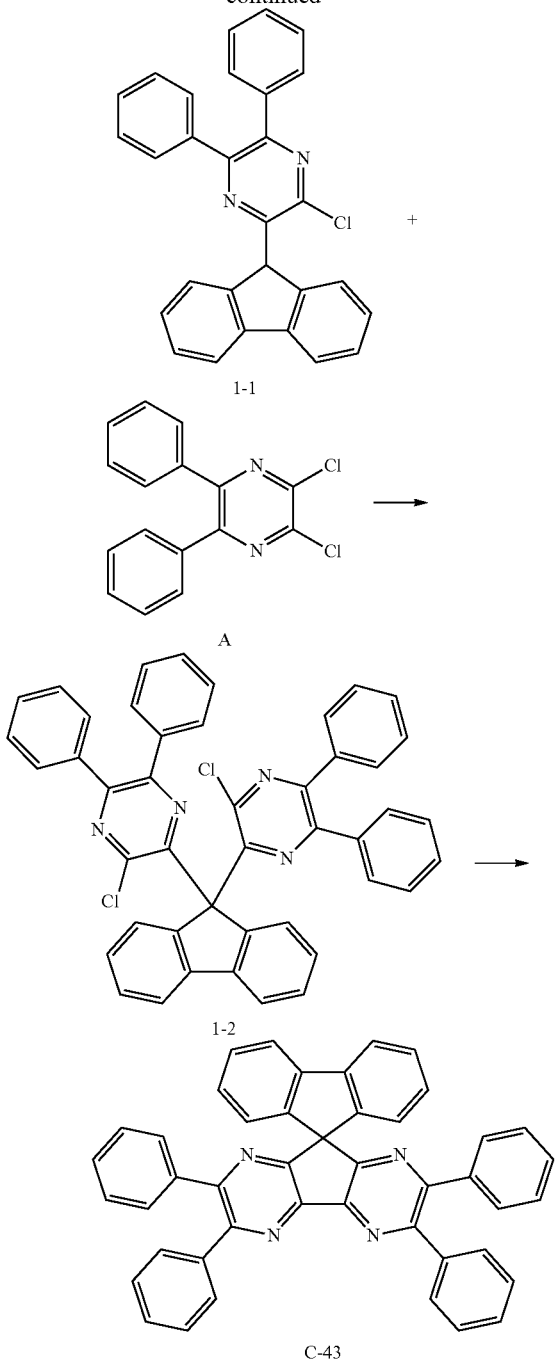

Synthesis of Compound 1-1

Compound A (2,3-dichloro-5,6-diphenylpyrazine) (9 g, 30 mmol) and compound B (9H-fluorene) (10 g, 60 mmol) were dissolved in 150 mL of THF, and $Cs_2CO_3$ (29.3 g, 90 mmol) was added thereto, and then the mixture was refluxed for 48 hours. Thereafter, the mixture was distilled under reduced pressure, and separated by column chromatography to obtain compound 1-1 (9 g, yield: 70%).

Synthesis of Compound 1-2

Compound 1-1 (10.5 g, 24.4 mmol), compound A (2,3-dichloro-5,6-diphenylpyrazine) (14.6 g, 48.7 mmol), $Pd_2(dba)_3$ (3.3 g, 3.6 mmol), ligand (triphenylphosphine) (1.9 g, 7.3 mmol), and 250 mL of toluene were stirred at room temperature under nitrogen atmosphere. 30 mL of KOtBu (1M in THF) was added to the mixture, and stirred under reflux for 18 hours. The mixture was cooled to room temperature, and distilled water was added thereto. An organic layer was extracted with ethyl acetate, and separated by column chromatography to obtain compound 1-2 (7 g, yield: 42%).

Synthesis of Compound C-43

Nickel chloride (1.5 g, 11.8 mmol), triphenylphosphine (12.4 g, 47.2 mmol), and 50 mL of DMF were stirred at 60° C. under nitrogen atmosphere. Zinc powder (0.77 g, 11.8 mmol) and 10 mL of DMF were added to the mixture, and the mixture was stirred for 90 minutes. Compound 1-2 (4.1 g, 5.9 mmol) and 40 mL of DMF were added to the mixture, and the mixture was stirred for 2 hours. The mixture was cooled to room temperature, and distilled water was added thereto. The mixture was filtered under reduced pressure, and the obtained solid was separated by column chromatography to obtain compound C-43 (3.4 g, yield: 92%).

|      | MW     | M.P.     |
|------|--------|----------|
| C-43 | 624.75 | 325.7° C.|

Hereinafter, a method of producing an organic electroluminescent device (OLED) according to the present disclosure and the luminous efficiency and lifetime properties thereof will be explained in detail. However, the present disclosure is not limited by the following examples.

Device Example 1: Producing an OLED Comprising the Organic Electroluminescent Compound According to the Present Disclosure An OLED according to the present disclosure was produced. A transparent electrode indium tin oxide (ITO) thin film (10 Ω/sq) on a glass substrate for an OLED (GEO-MATEC CO., LTD., Japan) was subjected to an ultrasonic washing with acetone and isopropyl alcohol, sequentially, and then was stored in isopropanol. The ITO substrate was then mounted on a substrate holder of a vacuum vapor deposition apparatus. Compound HI-1 was introduced into a cell of the vacuum vapor deposition apparatus, and compound HT-1 was introduced into another cell of the vacuum vapor deposition apparatus. The two materials were evaporated at different rates, and compound HI-1 was deposited in a doping amount of 3 wt % based on the total amount of compound HI-1 and compound HT-1 to form a hole injection layer having a thickness of 10 nm on the ITO substrate. Next, compound HT-1 was deposited on the hole injection layer to form a first hole transport layer having a thickness of 80 nm. Compound HT-2 was then introduced into another cell of the vacuum vapor deposition apparatus and was evaporated by applying an electric current to the cell, thereby forming a second hole transport layer having a thickness of 60 nm on the first hole transport layer. After forming the hole injection layer and the hole transport layers, a light-emitting layer was formed thereon as follows: Compound C-43 was introduced into a cell of the vacuum vapor deposition apparatus as a host, and compound D-39 was introduced into another cell as a dopant. The two materials were evaporated at different rates and the dopant was deposited in a doping amount of 3 wt % based on the total amount of the host and the dopant to form a light-emitting layer having a thickness of 40 nm on the second hole transport layer. Compound ETL-1 and compound EIL-1 were evaporated in a weight ratio of 50:50 to form an electron transport layer having a thickness of 35 nm on the light-emitting layer. After depositing compound EIL-1 as an electron injection layer having a thickness of 2 nm on the electron transport layer, an Al cathode having a thickness of 80 nm was deposited on the electron injection layer by another vacuum vapor deposition apparatus. Thus, an OLED was produced. All the materials used for producing the OLED were purified by vacuum sublimation at $10^{-6}$ torr.

The produced OLED had a driving voltage of 4.2 V, a luminous efficiency of 26.0 cd/A, and a light-emitting color of red at a luminance of 1,000 nit.

From Device Example 1, it can be confirmed that the organic electroluminescent compound according to the present disclosure can produce an OLED having excellent luminous properties, in particular, driving voltage/luminous efficiency, compared to conventional organic electroluminescent compounds. It is understood that the compound according to the present disclosure is advantageous for transporting electrons as a host, since it has lower energy level of molecular orbital than conventional compounds. For example, the HOMO (highest occupied molecular orbital) energy and the LUMO (lowest unoccupied molecular orbital) energy of compound C-43, which is an organic electroluminescent compound of the present disclosure, and compound A, which is a conventional organic electroluminescent compound, are compared as shown in Table 1.

TABLE 1

| Compound | | HOMO | LUMO |
|---|---|---|---|
| C-43 | 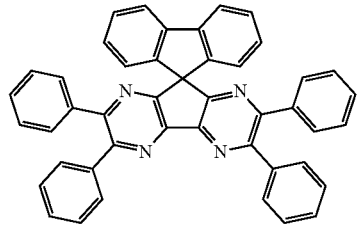 | −5.630 | −2.088 |
| A | 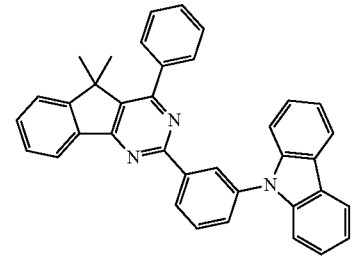 | −5.204 | −1.567 |

Device Example 2: Producing an OLED Co-Deposited with the First and Second Host Compounds An OLED was produced in the same manner as in Device Example 1, except that the first and second host compounds shown in Table 2 below were respectively introduced into two cells of the vacuum vapor deposition apparatus as hosts of the light-emitting layer and deposited.

Comparative Example 1: Producing an OLED Comprising a Comparative Compound as a Host An OLED was produced in the same manner as in Device Example 1, except that instead of compound C-43, compound H1-9 was used as a host of the light-emitting layer.

The driving voltage, luminous efficiency, and light-emitting color at a luminance of 1,000 nit of the OLEDs produced in the Device Example and the Comparative Example are provided in Table 2.

TABLE 2

| | First Host | Second Host | Driving Voltage [V] | Luminous Efficiency [cd/A] | Light-Emitting Color |
|---|---|---|---|---|---|
| Device Example 2 | C-43 | H1-9 | 3.3 | 31.1 | Red |
| Comparative Example 1 | — | H1-9 | 4.2 | 6.9 | Red |

From Table 2 above, it can be confirmed that the OLED using a plurality of host materials comprising the compound represented by formula 1 of the present disclosure and the compound represented by formula 11 of the present disclosure exhibits lower driving voltage and higher luminous efficiency than the OLED using the compound represented by formula 11 as a single host material.

The compounds used in the Device Examples and the Comparative Example are shown in Table 3.

TABLE 3

Hole Injection Layer/ Hole Transport Layer

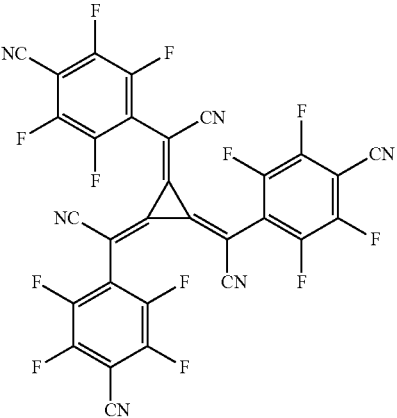

HI-1

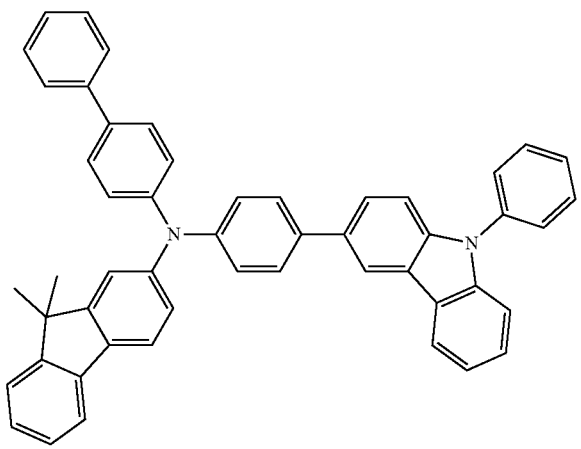

HT-1

TABLE 3-continued
| | | HT-2 |
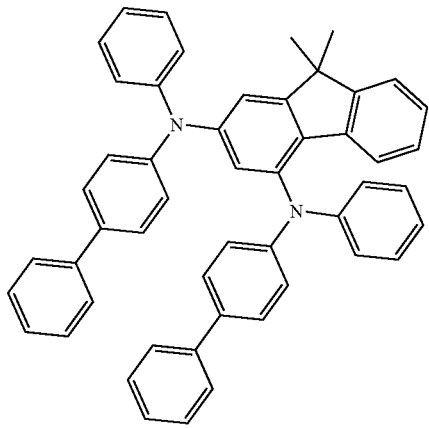
| Light-Emitting Layer | | C-43 |
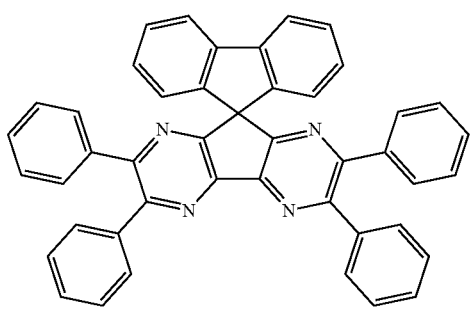 [SMILES: c1ccc(-c2nc3c(nc2-c2ccccc2)C2(c4ccccc4-c4ccccc42)c2nc(-c4ccccc4)c(-c4ccccc4)nc2-3)cc1]
| | | H1-9 |
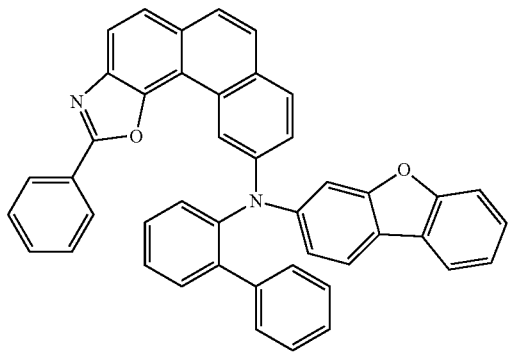
| | | D-39 |
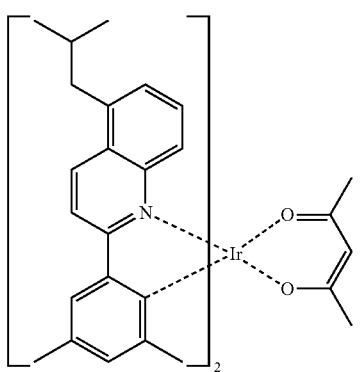

TABLE 3-continued
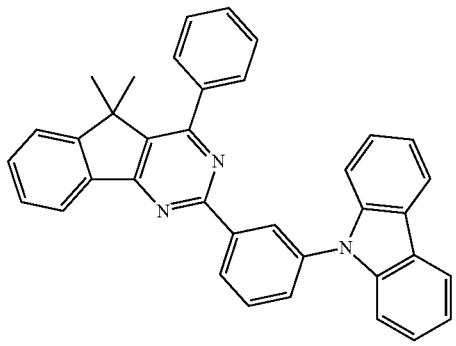 [SMILES: CC1(C)c2ccccc2-c2nc(-c3cccc(-n4c5ccccc5c5ccccc54)c3)nc(-c3ccccc3)c21]
A
Electron Transport Layer/ Electron Injection Layer
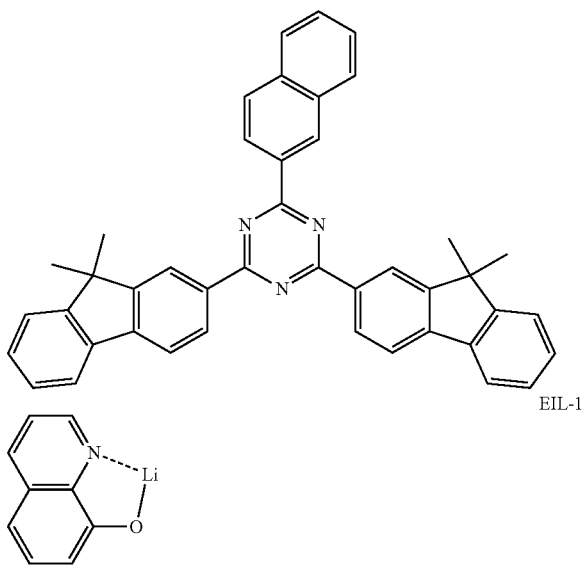
ETL-1
EIL-1
The invention claimed is:
1. An organic electroluminescent compound represented by the following formula 1:
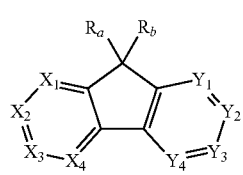
(1)
wherein the formula 1 is represented by at least one of the following formulas 2-1 to 2-4:
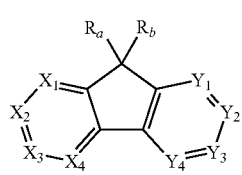
(2-1)
-continued
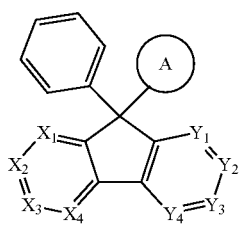
(2-2)
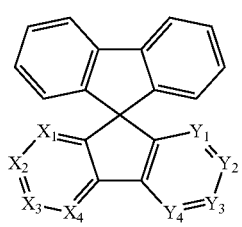
(2-3)

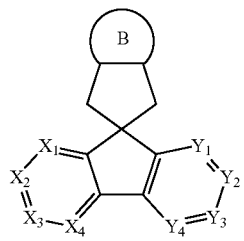
(2-4)

in formulas 2-1 to 2-4, $X_1$ to $X_4$, each independently, represent N or $CR_c$, and at least two of $X_1$ to $X_4$ represent N;

$Y_1$ to $Y_4$, each independently, represent N or $CR_d$, and at least one of $Y_1$ to $Y_4$ represents N;

$R_c$ and $R_d$, each independently, are represented by -L-Ar;

L represents a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene;

Ar represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, or a substituted or unsubstituted (C1-C30)alkoxy; or is represented by the following formula 3 or 4:

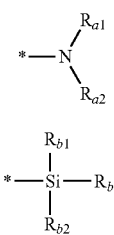
(3)

(4)

in formulas 3 and 4, $R_{a1}$, $R_{a2}$, $R_{b1}$, $R_{b2}$, and $R_{b3}$, each independently, represent a substituted or unsubstituted (C6-C30)aryl, a substituted or unsubstituted (3- to 30-membered)heteroaryl, or a substituted or unsubstituted (C3-C30)cycloalkyl, and

* represents a site linked to L; or at least two adjacent Ar's may be linked to each other to form a ring(s);

$R_a$ represents a methyl, an ethyl, an n-propyl, an isopropyl, an n-butyl, an isobutyl, or a tert-butyl;

$R_b$ represents a methyl, an ethyl, an n-propyl, an isopropyl, an n-butyl, an isobutyl, a tert-butyl, or a phenyl;

ring A represents a benzene or a naphthalene; and ring B is absent, or represents a benzene.

2. The organic electroluminescent compound according to claim 1, wherein the formula 1 is represented by at least one of the following formulas 1-1 to 1-3:

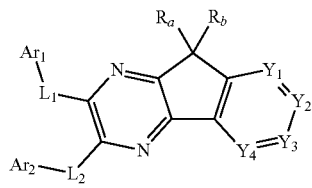
(1-1)

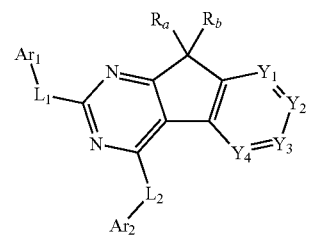
(1-2)

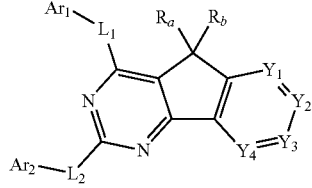
(1-3)

in formulas 1-1 to 1-3, $R_a$, $R_b$, and $Y_1$ to $Y_4$ are as defined in claim 1;

$L_1$ and $L_2$, each independently, are the same as the definition of L in claim 1; and $Ar_1$ and $Ar_2$, each independently, are the same as the definition of Ar in claim 1.

3. The organic electroluminescent compound according to claim 1, wherein the formula 1 is represented by at least one of the following formulas 1~4 and 1-9:

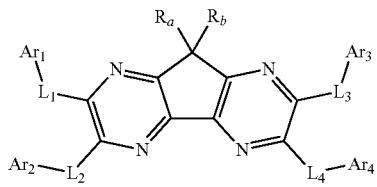
(1-4)

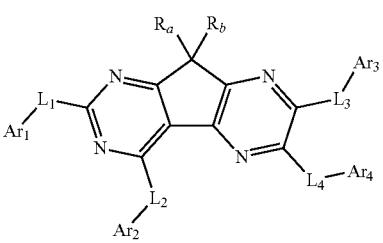
(1-9)

in formulas 1-4 and 1-9, $R_a$ and $R_b$ are as defined in claim 1;

$L_1$ to $L_4$, each independently, are the same as the definition of L in claim 1; and $Ar_1$ to $Ar_4$, each independently, are the same as the definition of Ar in claim 1.

4. The organic electroluminescent compound according to claim 1, wherein at least one of Ar's represents a substituted or unsubstituted (C6-C30)aryl, a substituted or unsubstituted (3- to 30-membered)heteroaryl, a substituted or unsubstituted (C3-C30)cycloalkyl, or a substituted or unsubstituted (C1-C30)alkoxy; or is represented by formula 3 or 4.

5. The organic electroluminescent compound according to claim 1, wherein the substituent(s) of the substituted alkyl (ene), the substituted aryl (ene), the substituted heteroaryl (ene), the substituted cycloalkyl (ene), and the substituted alkoxy, each independently, are at least one selected from the group consisting of deuterium; a halogen; a cyano; a carboxyl; a nitro; a hydroxyl; a phosphineoxide; a (C1-C30) alkyl; a halo (C1-C30)alkyl; a (C2-C30)alkenyl; a (C2-C30) alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (5- to 30-membered)heteroaryl unsubstituted or substituted with a (C6-C30)aryl(s); a (C6-C30)aryl unsubstituted or substituted with a (5- to 30-membered) heteroaryl(s); a tri(C1-C30)alkylsilyl; a tri(C6-C30)arylsilyl; a di(C1-C30)alkyl (C6-C30)arylsilyl; a (C1-C30)alkyldi (C6-C30)arylsilyl; a fused ring group of a (C3-C30) aliphatic ring(s) and a (C6-C30) aromatic ring(s); an amino; a mono- or di-(C1-C30)alkylamino; a mono- or di-(C2-C30) alkenylamino; a mono- or di-(C6-C30)arylamino unsubstituted or substituted with a (C1-C30)alkyl(s); a mono- or di-(3- to 30-membered)heteroarylamino; a (C1-C30)alkyl (C2-C30)alkenylamino; a (C1-C30)alkyl (C6-C30)arylamino; a (C1-C30)alkyl (3- to 30-membered)heteroarylamino; a (C2-C30)alkenyl (C6-C30)arylamino; a (C2-C30) alkenyl (3- to 30-membered)heteroarylamino; a (C6-C30) aryl (3- to 30-membered)heteroarylamino; a (C1-C30) alkylcarbonyl; a (C1-C30)alkoxycarbonyl; a (C6-C30) arylcarbonyl; a (C6-C30)arylphosphine; a di(C6-C30) arylboronyl; a di(C1-C30)alkylboronyl; a (C1-C30)alkyl (C6-C30)arylboronyl; a (C6-C30)aryl (C1-C30)alkyl; and a (C1-C30)alkyl (C6-C30)aryl.

6. The organic electroluminescent compound according to claim 1, wherein the compound represented by formula 1 is at least one selected from the following compounds:

C-1
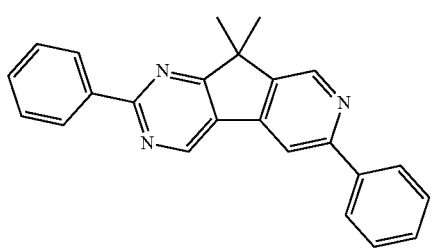

C-2
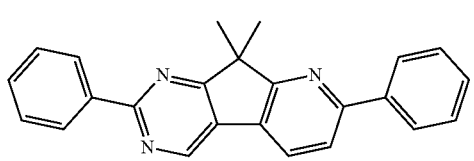

C-3
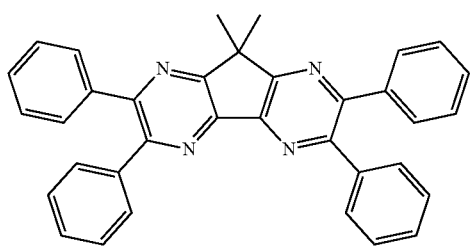

C-4
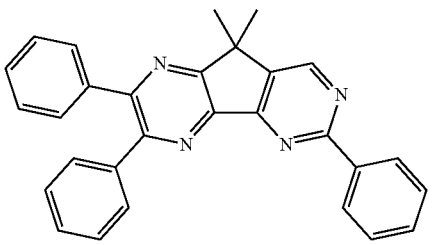

C-5
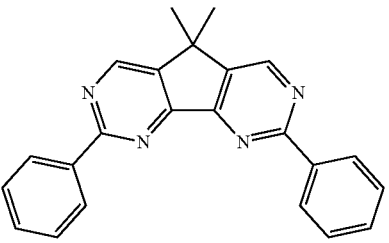

C-6
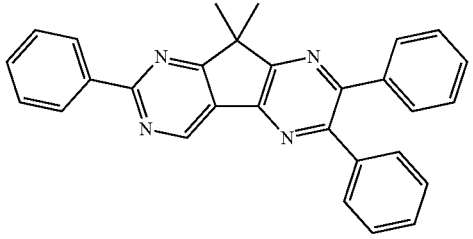

C-7
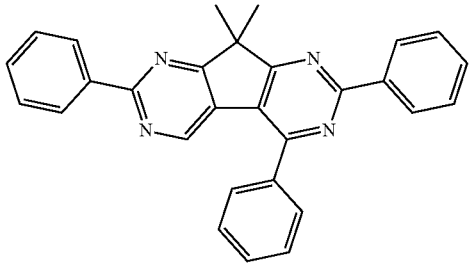

C-8
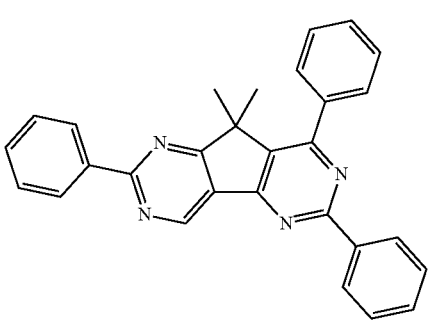

C-9
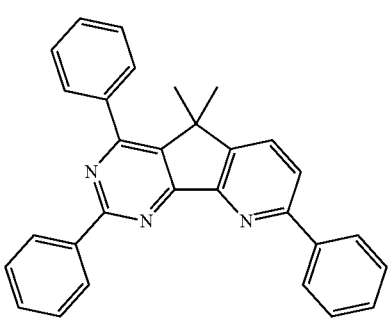

-continued
C-10
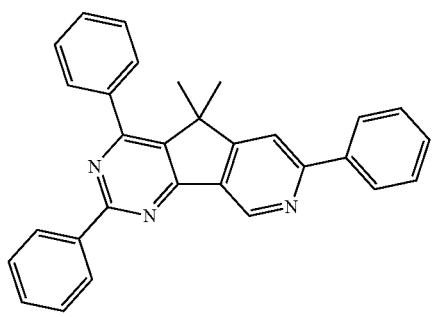
C-11
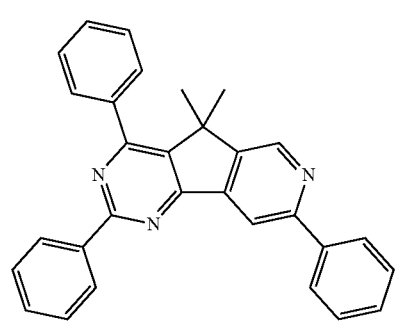
C-12
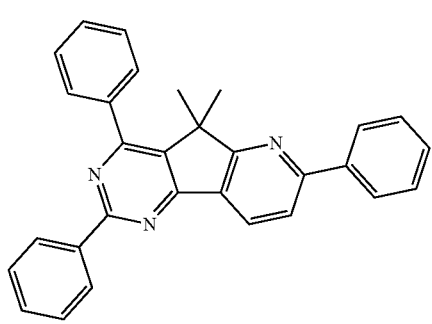
C-13
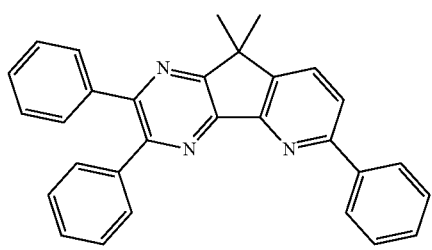
C-14
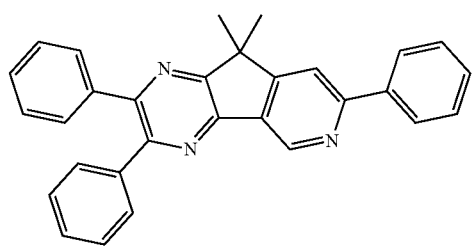
-continued
C-15
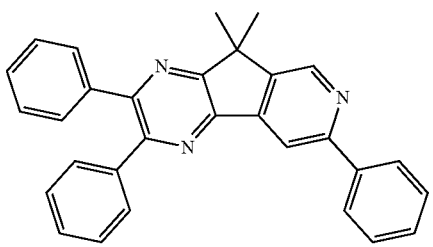
C-16
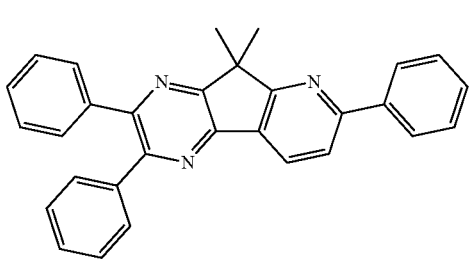
C-17
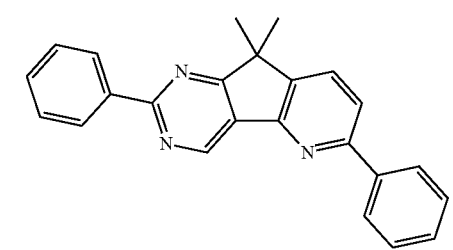
C-18
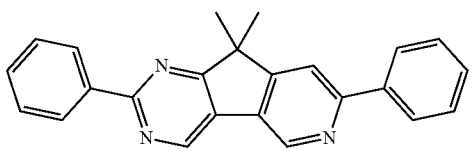
C-19
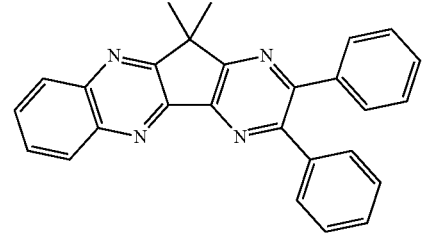
C-20
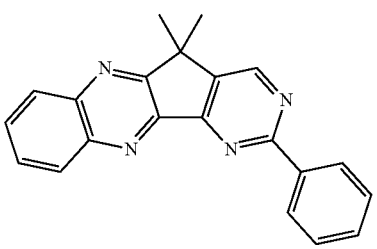

-continued
C-21
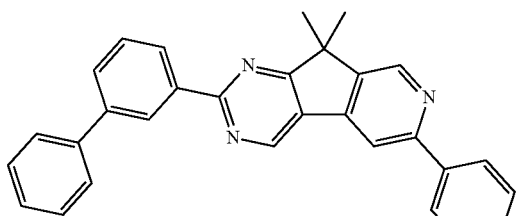
C-22
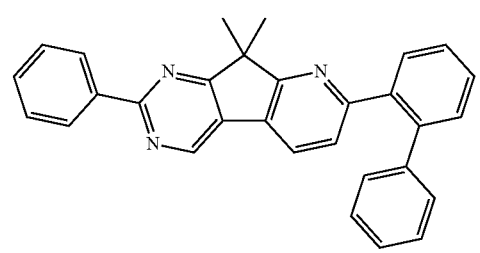
C-23
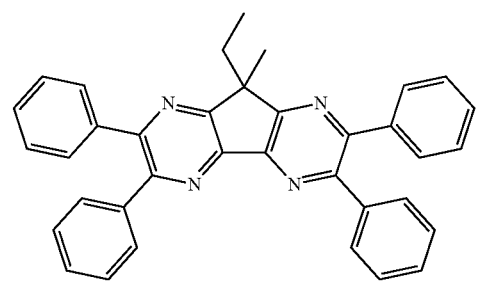
C-24
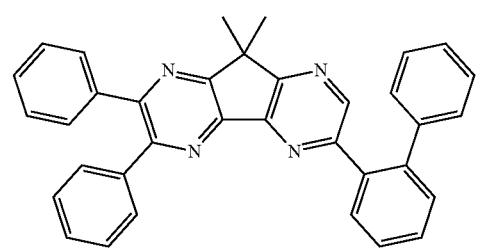
C-25
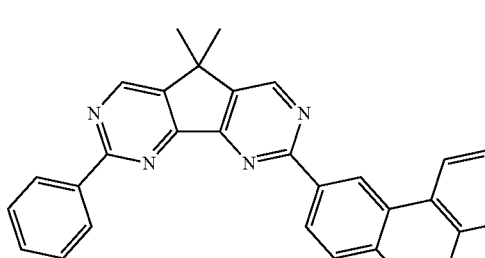
C-26
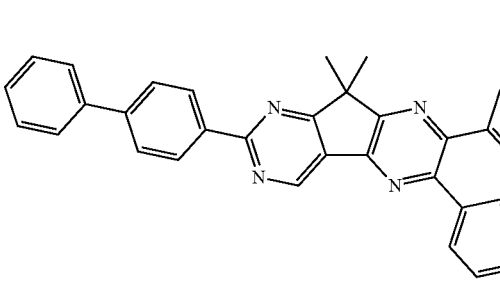
-continued
C-27
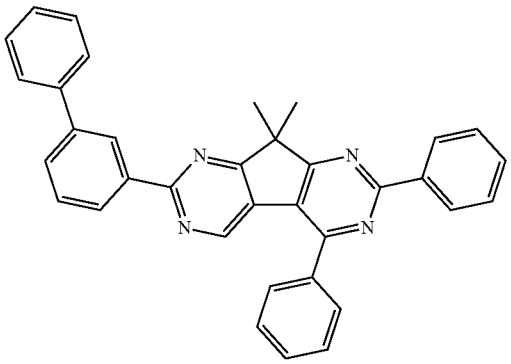
C-28
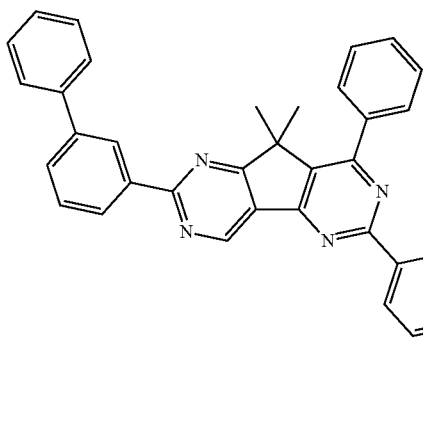
C-29
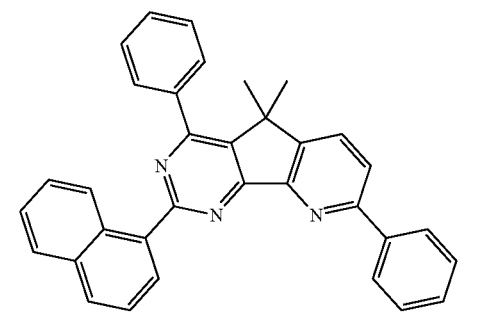
C-30
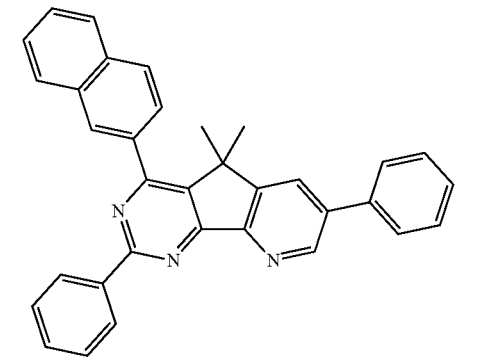

-continued
C-31
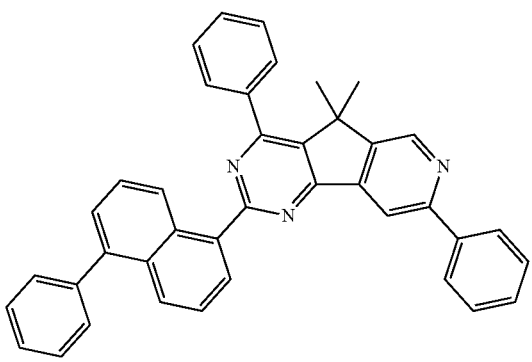
C-32
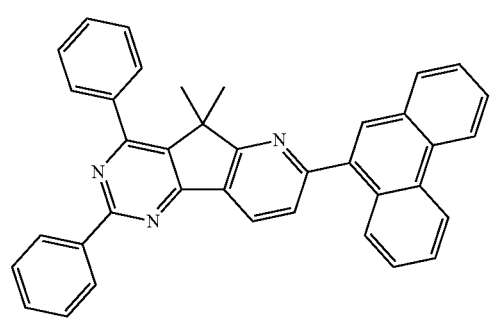
C-33
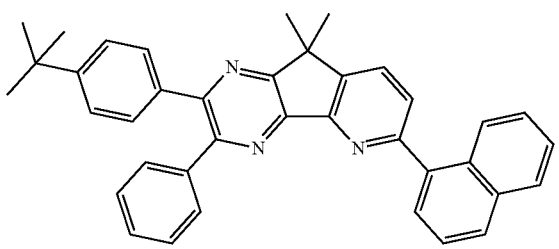
C-34
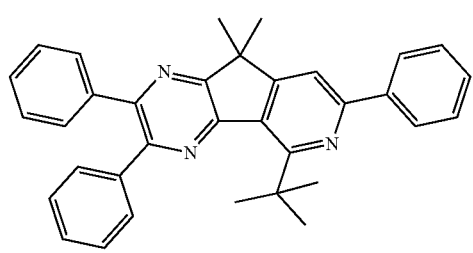
C-35
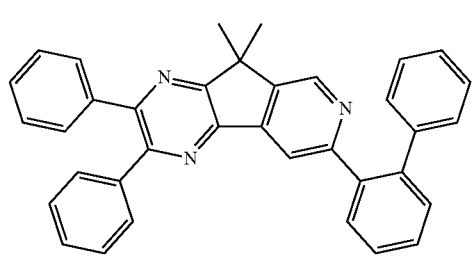
-continued
C-36
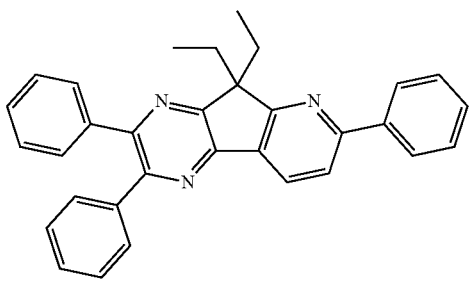
C-37
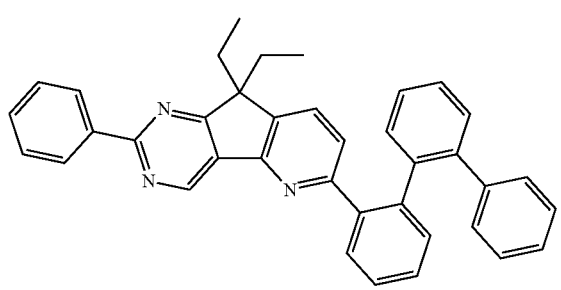
C-38
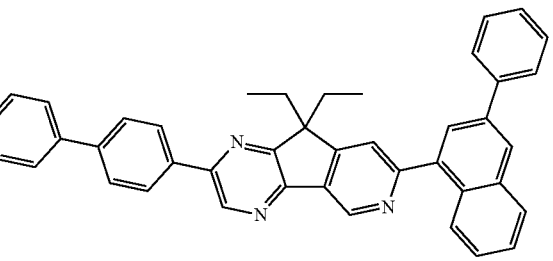
C-39
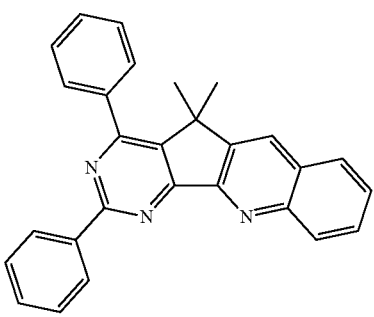
C-40
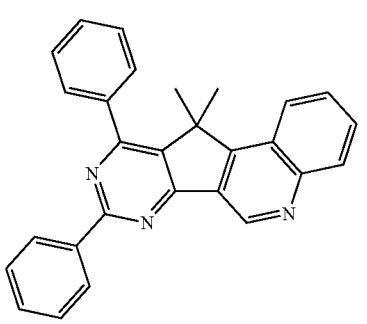

C-41
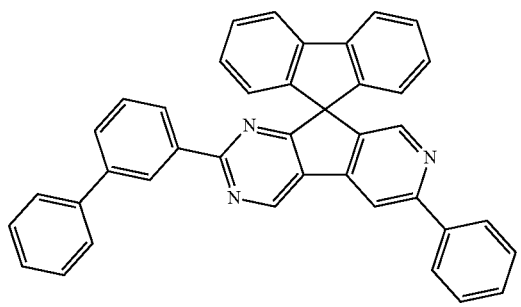
C-42
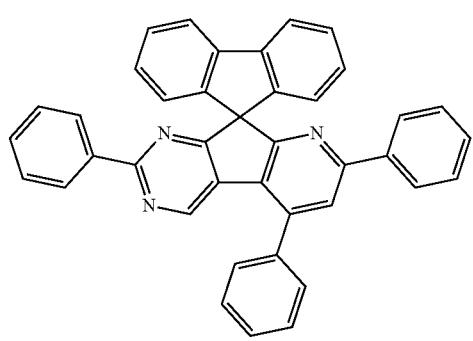
C-43
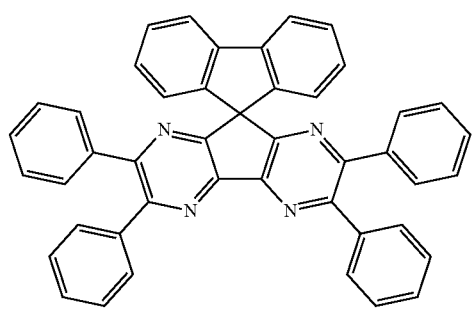
C-44
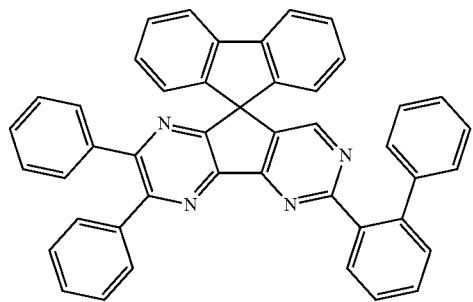
C-45
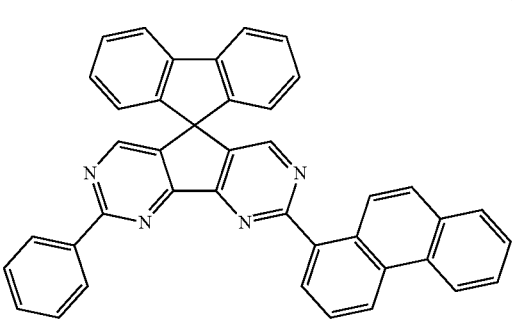
C-46
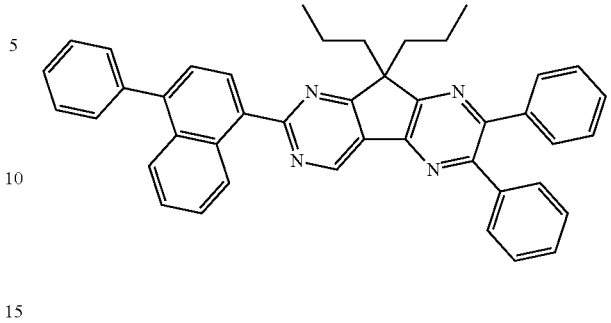
C-47
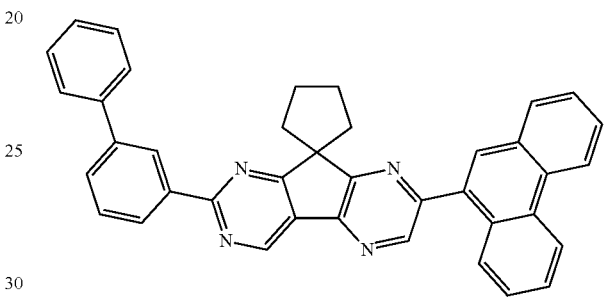
C-48
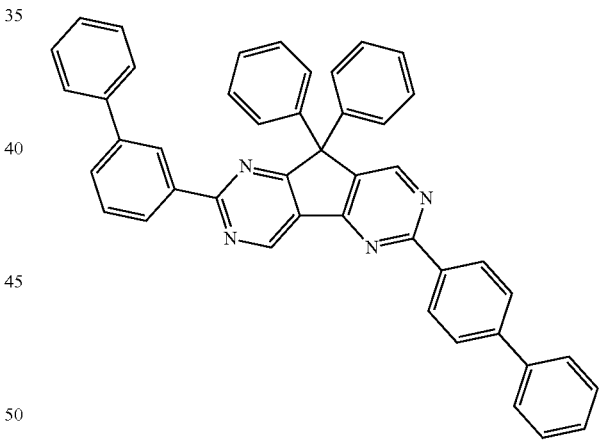
C-49
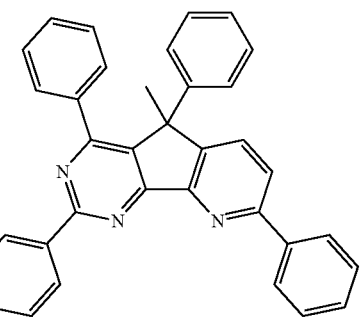

-continued
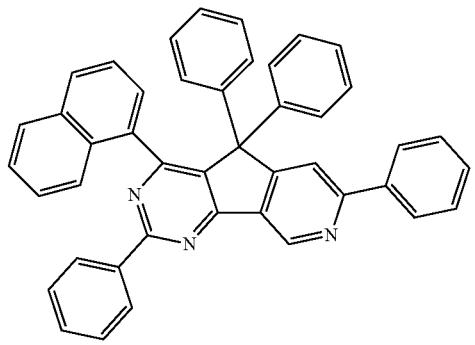
C-50
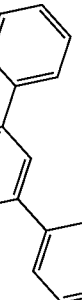
C-51
C-52
C-53
-continued
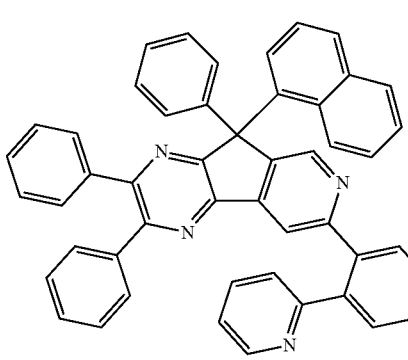
C-54
C-55
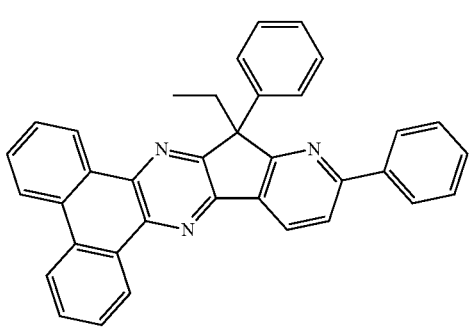
C-56
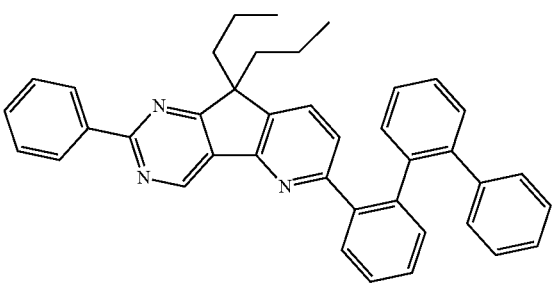
C-57
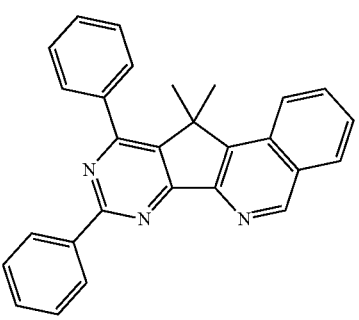
C-58

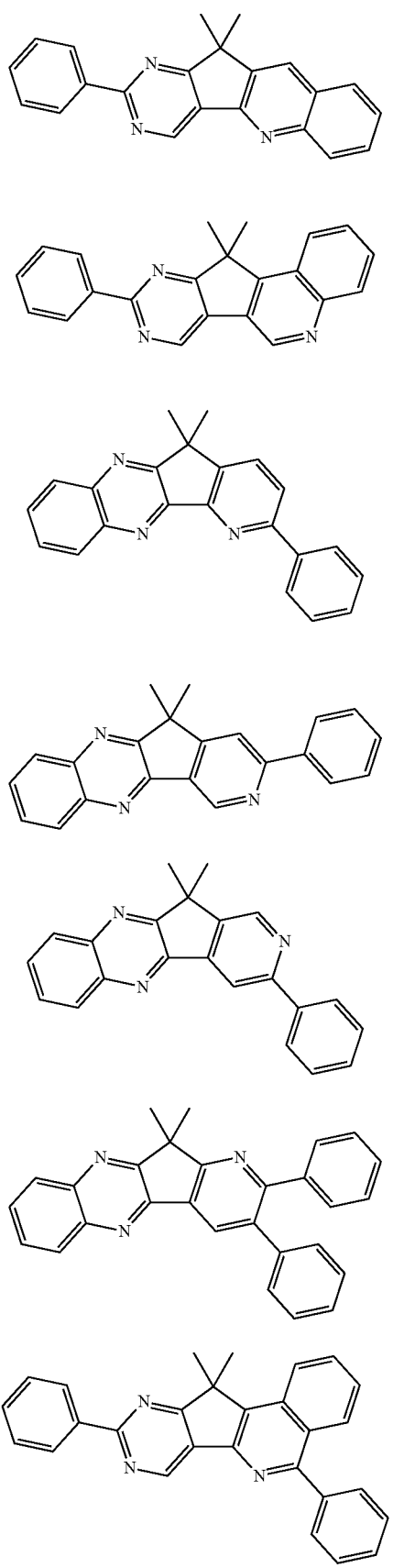
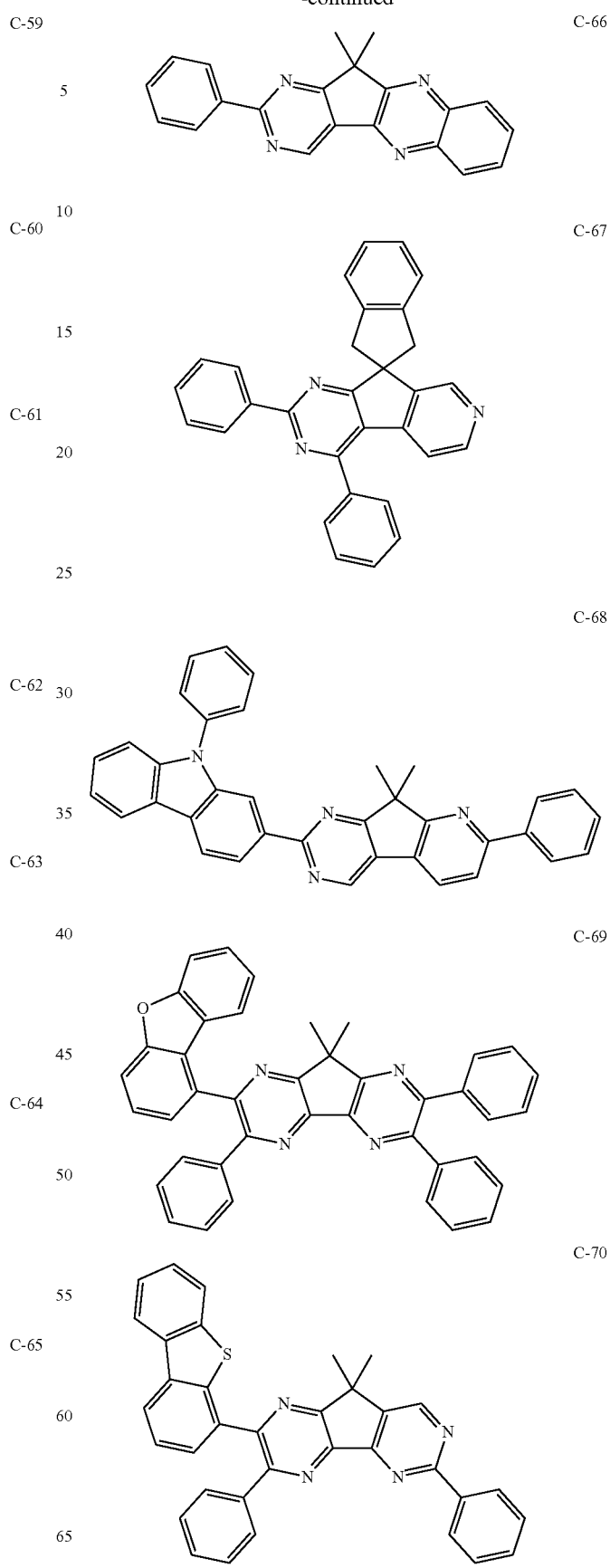

C-71
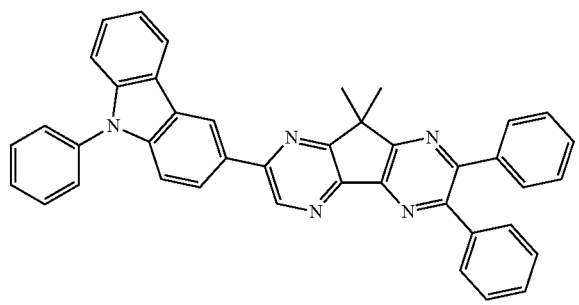
C-72
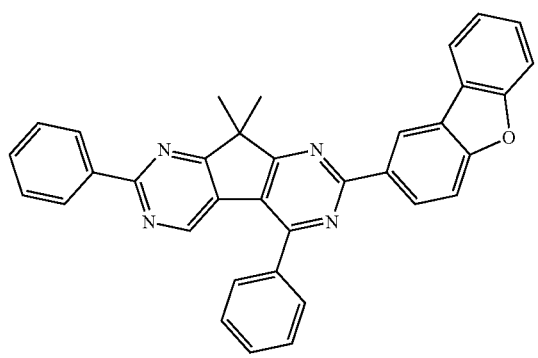
C-73
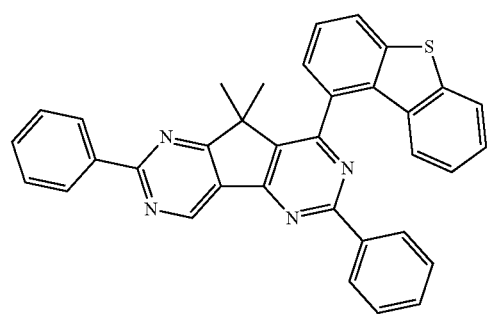
C-74
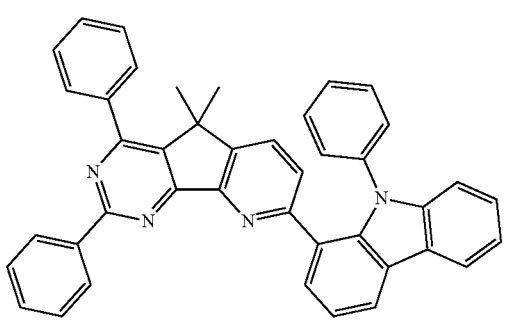
C-75
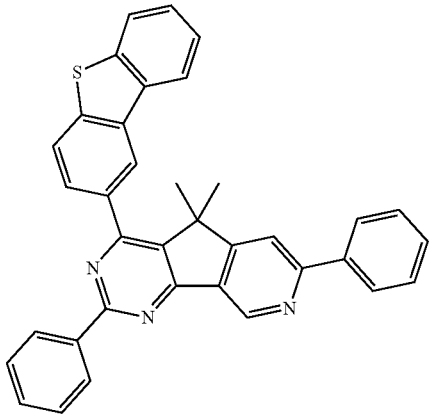
C-76
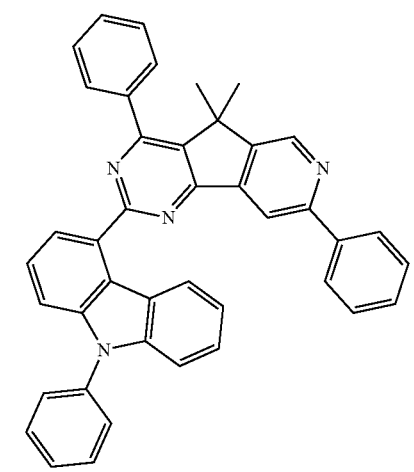
C-77
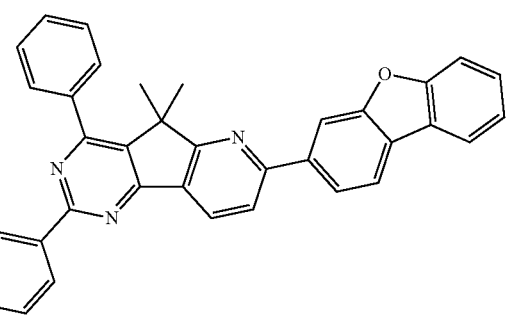
C-78
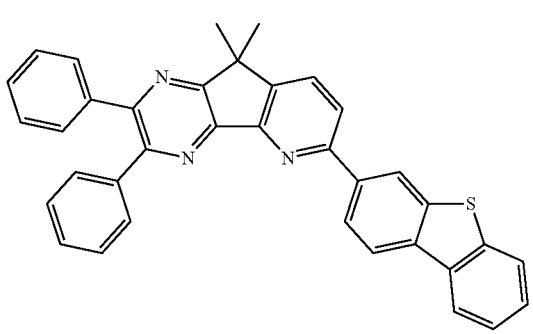

C-79
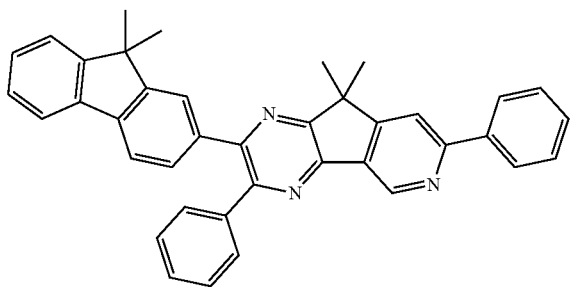
C-80
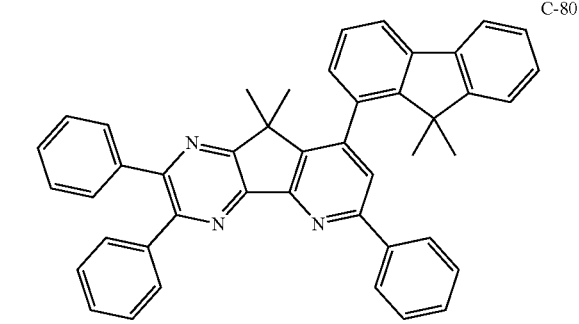
C-81
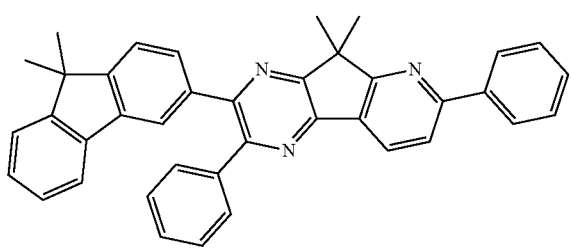
C-82
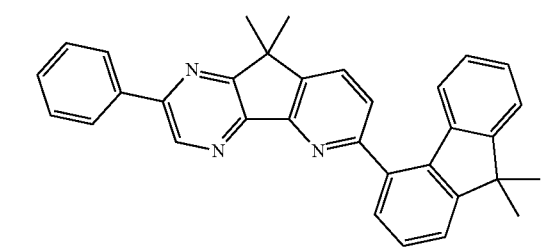
C-83
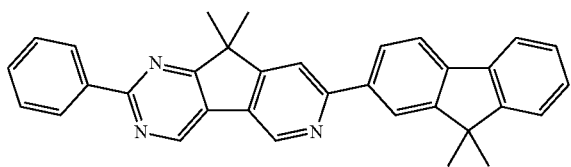
C-84
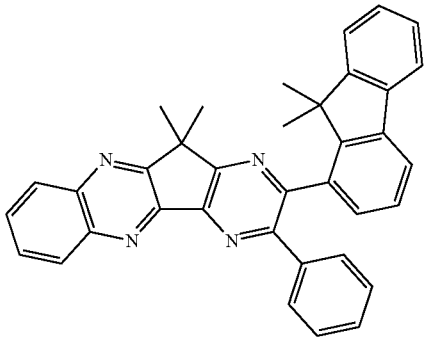
C-85
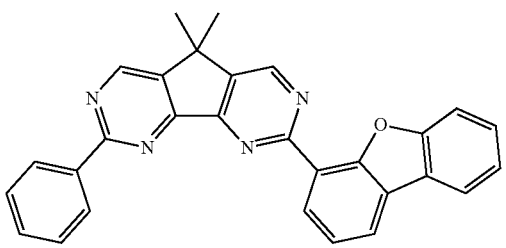
C-86
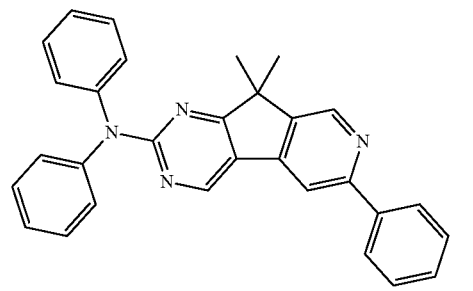
C-87
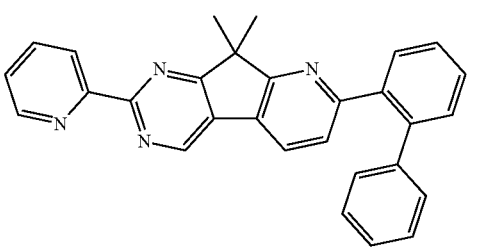
C-88
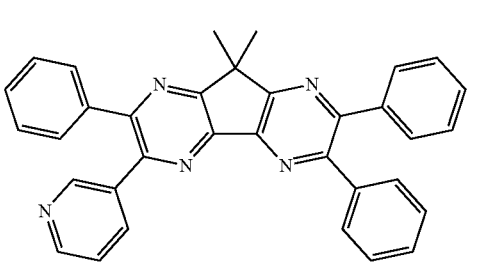
C-89
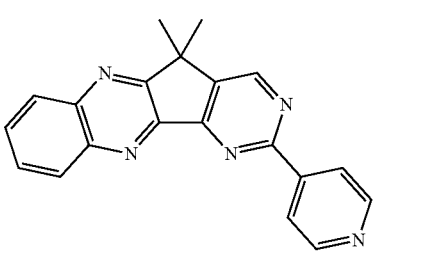

C-90
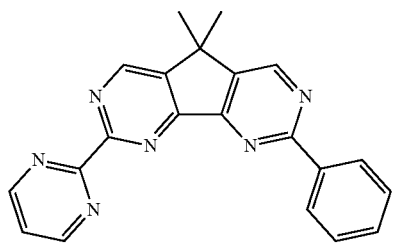
C-94
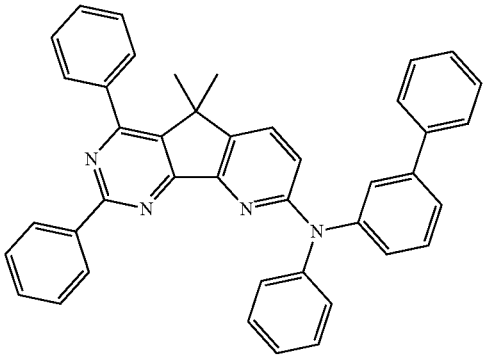
C-91
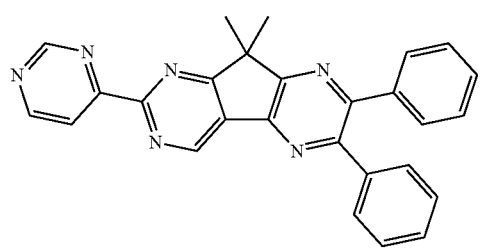
C-92
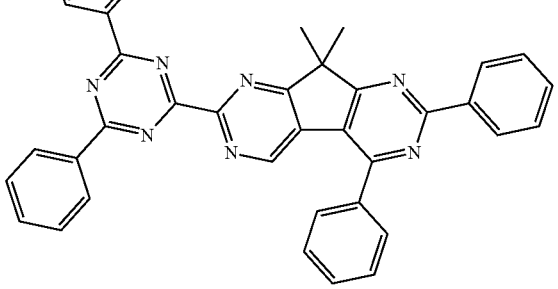
C-95
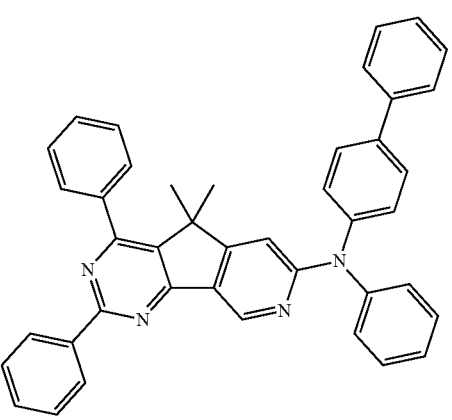
C-96
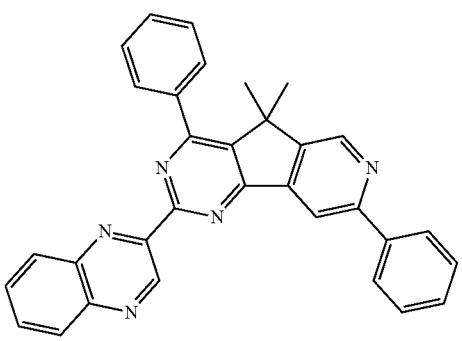
C-93
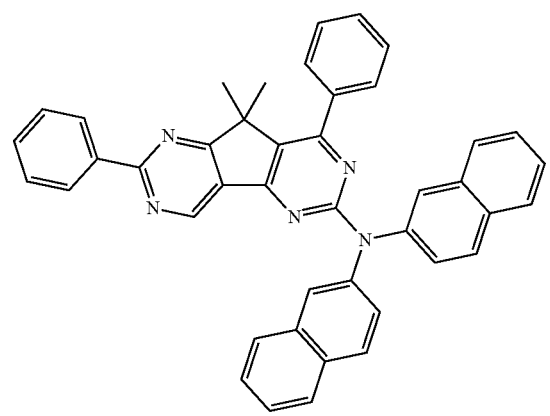
C-97
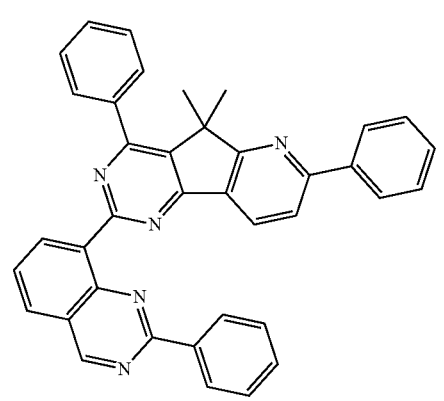

C-98
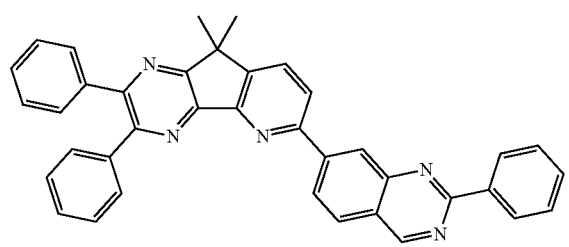
C-99
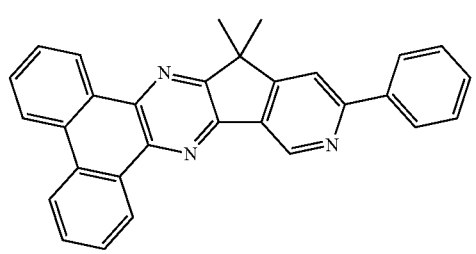
C-100
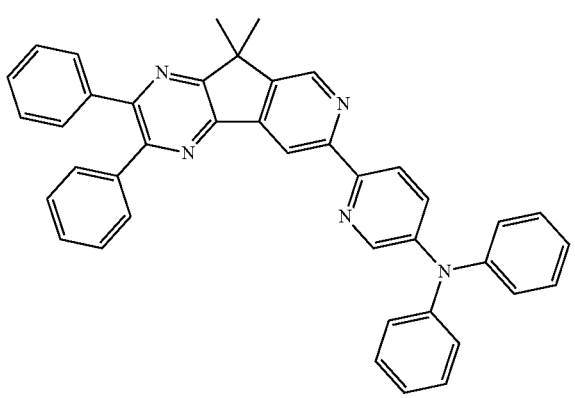
C-101
and
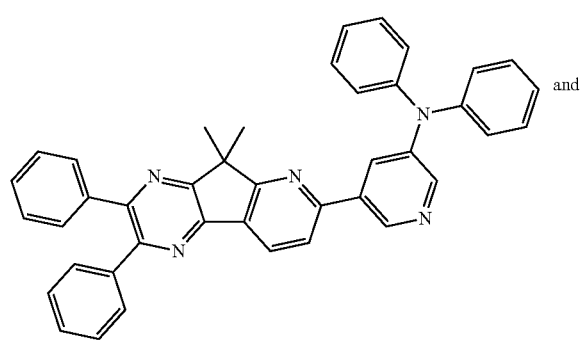
C-102
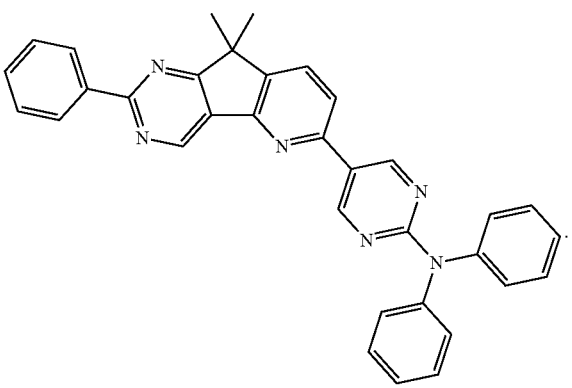
C-61
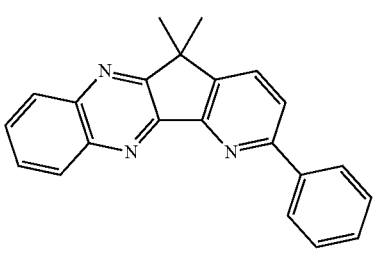
C-62
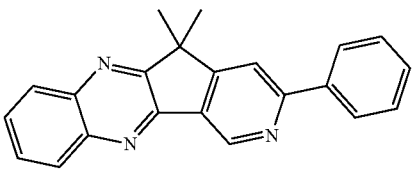
C-63
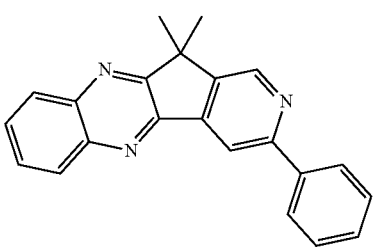
C-64
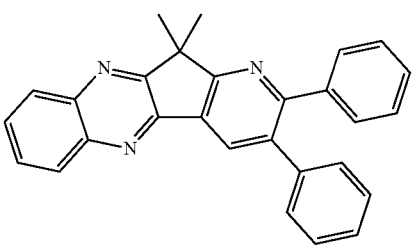

-continued
C-65
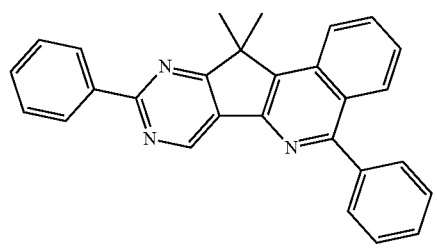
C-66
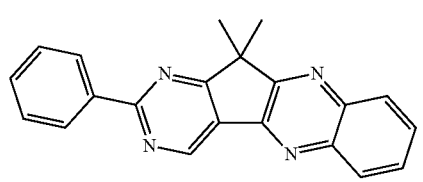
C-67
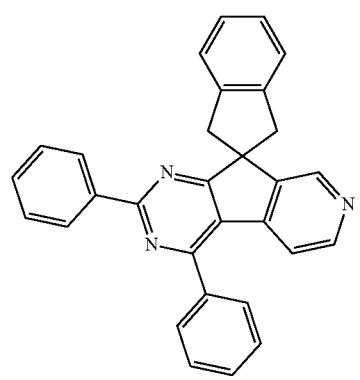
C-68
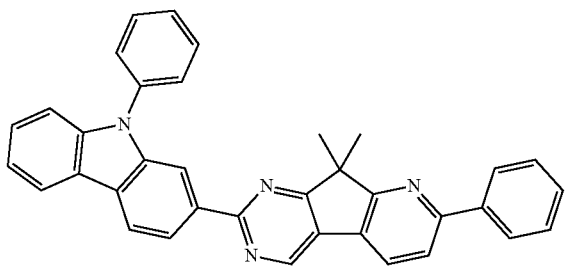
C-69
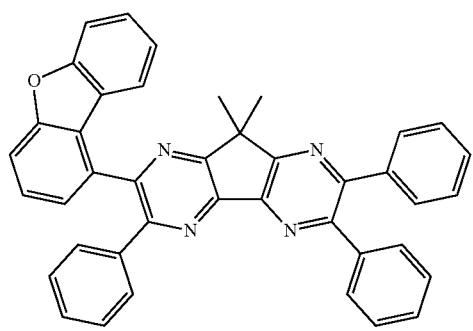
-continued
C-70
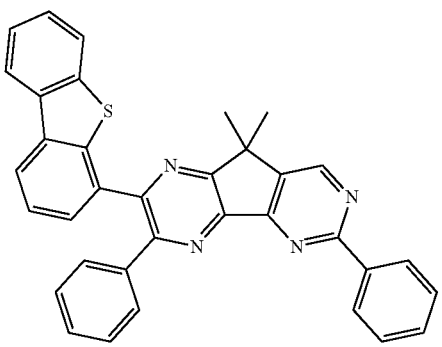
C-71
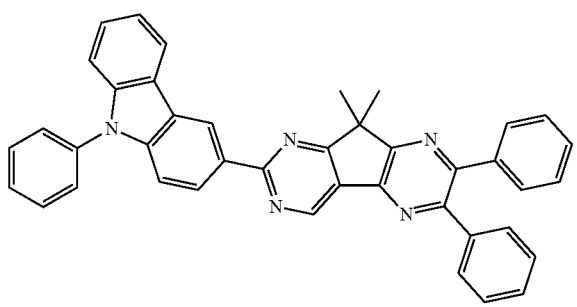
C-72
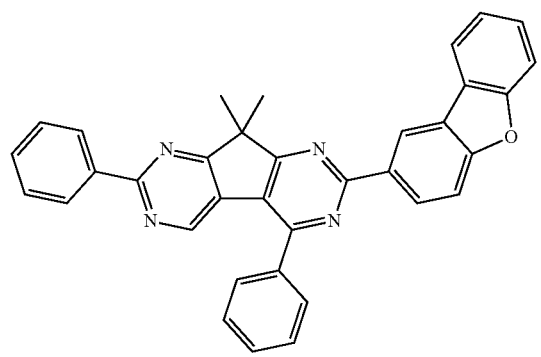
C-73
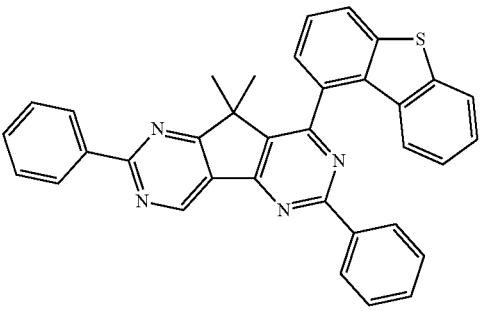

C-74
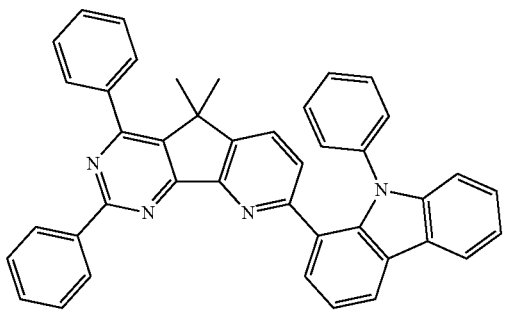
C-78
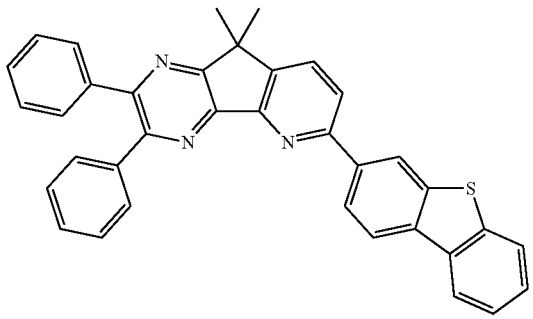
C-75
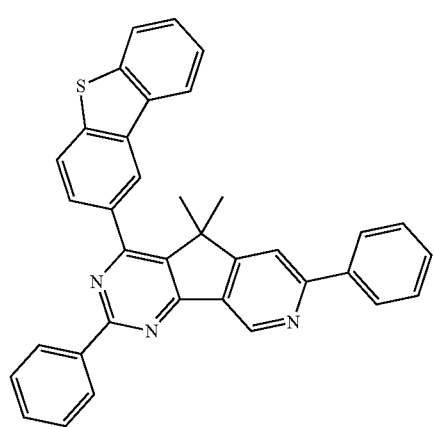
C-79
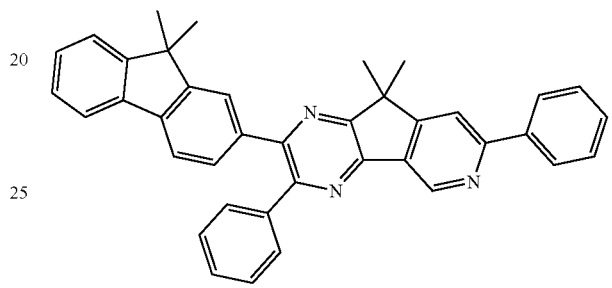
C-76
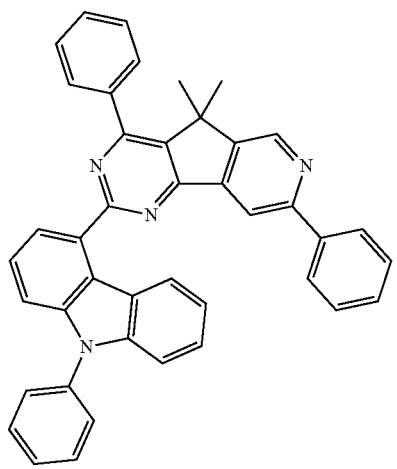
C-80
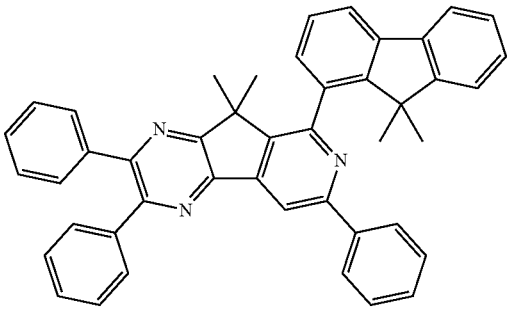
C-81
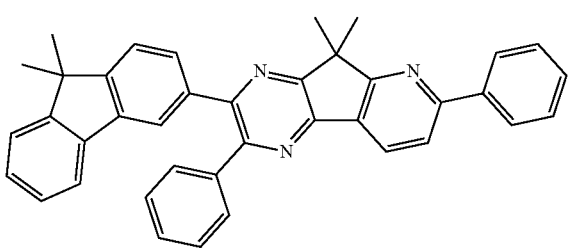
C-77
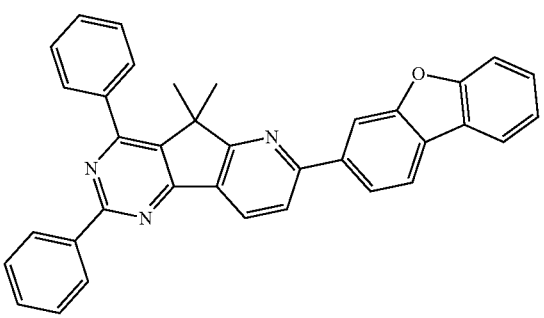
C-82
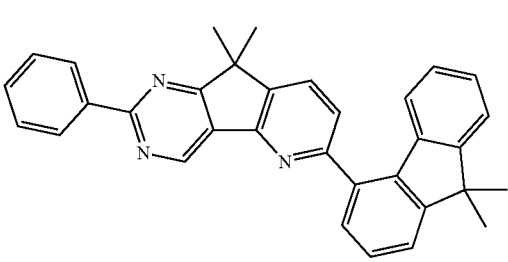

-continued
C-83
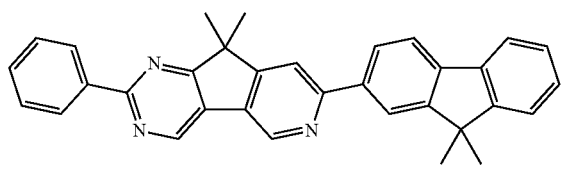
C-84
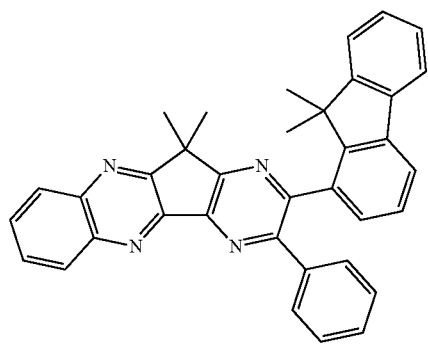
C-85
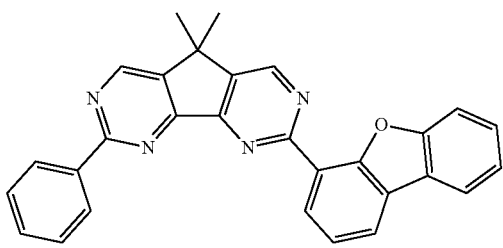
C-86
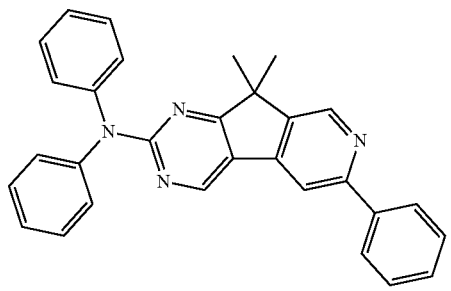
C-87
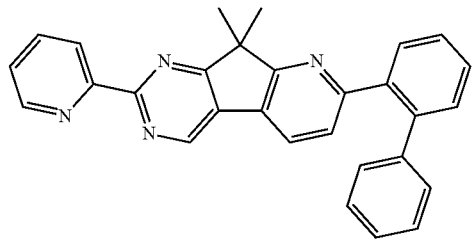
C-88
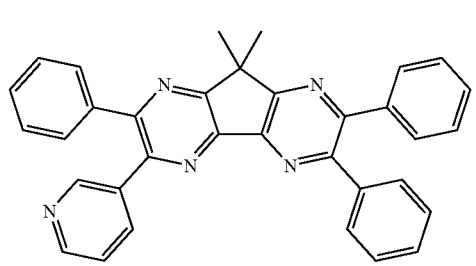
-continued
C-89
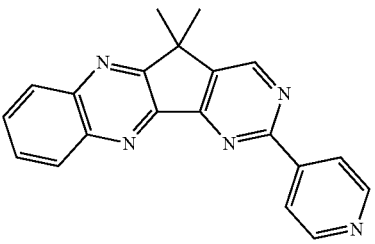
C-90
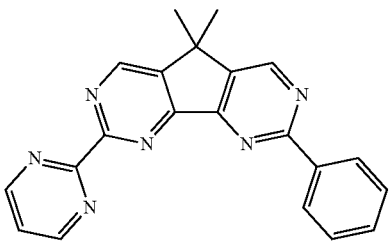
C-91
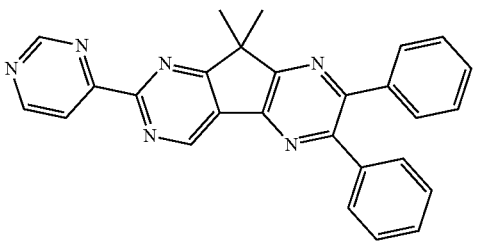
C-92
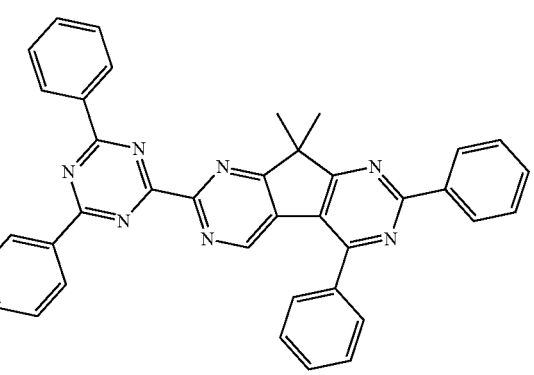
C-93
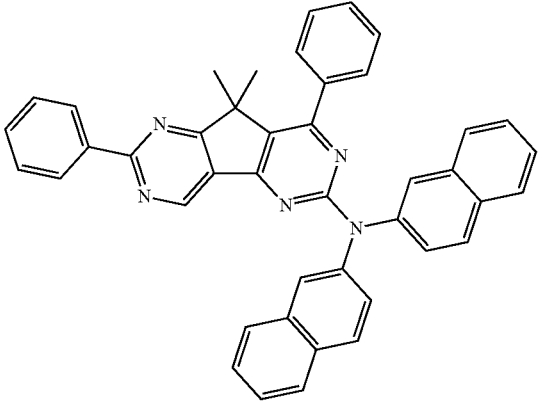

C-94
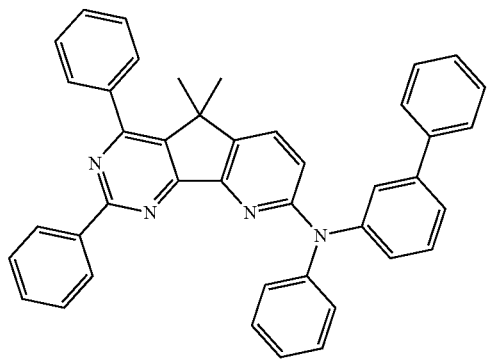
C-95
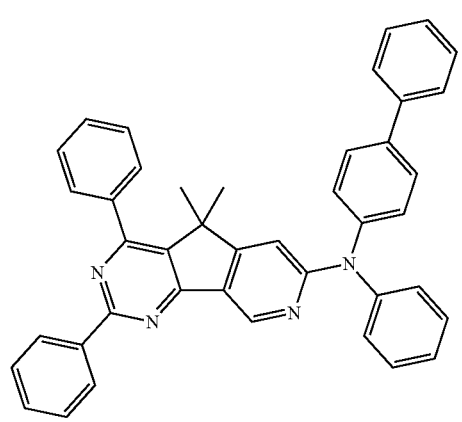
C-96
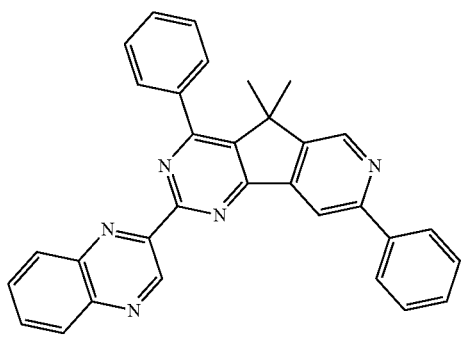
C-97
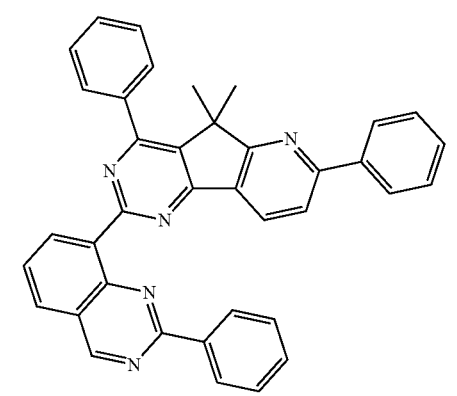
C-98
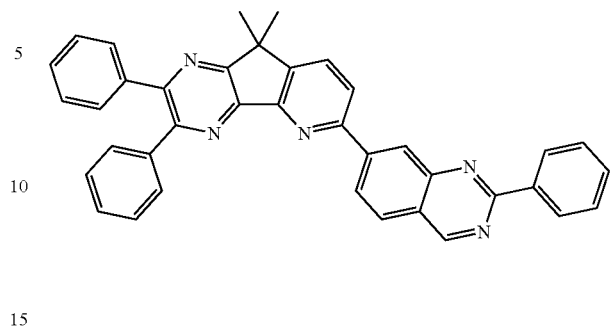
C-99
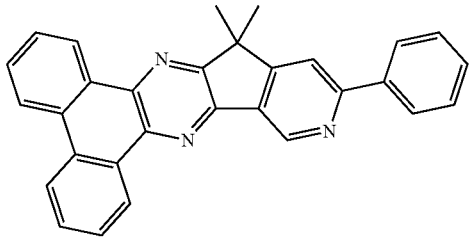
C-100
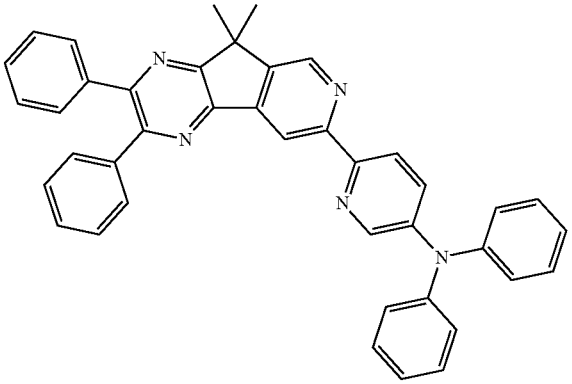
C-101
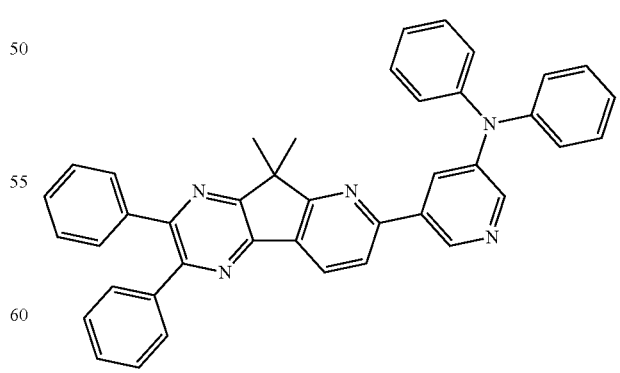
and -continued

C-102

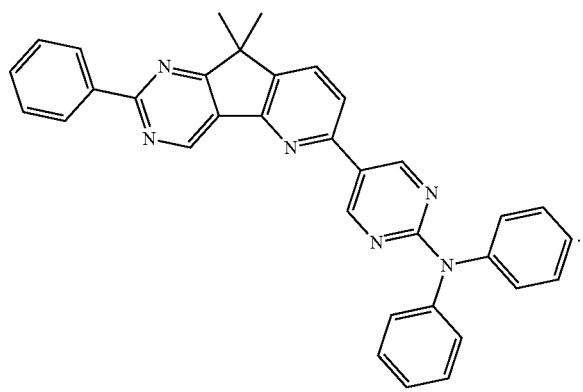

7. A plurality of host materials comprising a first host material and a second host material, wherein the first host material comprises the compound represented by formula 1 according to claim 1, and the second host material comprises a compound represented by the following formula 11:

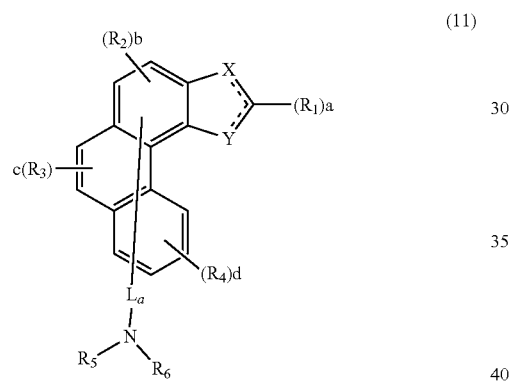
(11)

in formula 11,

X and Y, each independently, represent —N═, —NR7-, —O—, or —S—, with the proviso that any one of X and Y represents —N═, and the other one of X and Y represents —NR7-, —O—, or —S—;

$R_1$ represents a substituted or unsubstituted (C6-C30)aryl, or a substituted or unsubstituted (3- to 30-membered) heteroaryl;

$R_2$ to $R_7$, each independently, represent hydrogen, deuterium, a halogen, a cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl (C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring group of a (C3-C30) aliphatic ring(s) and a (C6-C30) aromatic ring(s), a substituted or unsubstituted mono- or di-(C1-C30)alkylamino, a substituted or unsubstituted mono- or di-(C2-C30)alkenylamino, a substituted or unsubstituted (C1-C30) alkyl (C2-C30)alkenylamino, a substituted or unsubstituted mono- or di-(C6-C30)arylamino, a substituted or unsubstituted (C1-C30)alkyl (C6-C30)arylamino, a substituted or unsubstituted mono- or di-(3- to 30-membered)heteroarylamino, a substituted or unsubstituted (C1-C30)alkyl (3- to 30-membered)heteroarylamino, a substituted or unsubstituted (C2-C30)alkenyl (C6-C30)arylamino, a substituted or unsubstituted (C2-C30)alkenyl (3- to 30-membered)heteroarylamino, or a substituted or unsubstituted (C6-C30)aryl (3- to 30-membered)heteroarylamino; or may be linked to an adjacent substituent to form a ring(s);

$L_a$ represents a single bond, a substituted or unsubstituted (C6-C30)arylene, or a substituted or unsubstituted (3- to 30-membered)heteroarylene; and a represents 1, b and c, each independently, represent an integer of 1 or 2, and d represents an integer of 1 to 4, in which if b to d are an integer of 2 or more, each of $R_2$ to each of $R_4$ may be the same or different.

8. The plurality of host materials according to claim 7, wherein the compound represented by formula 11 is at least one selected from the following compounds:

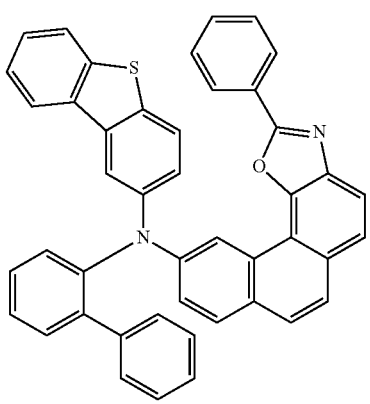
H1-1

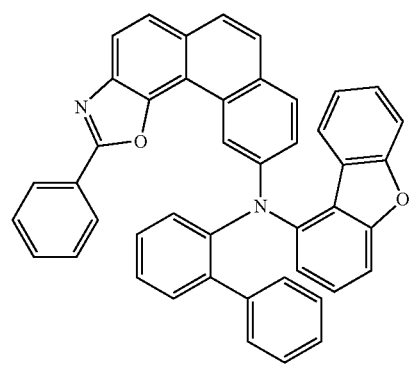
H1-2

H1-3
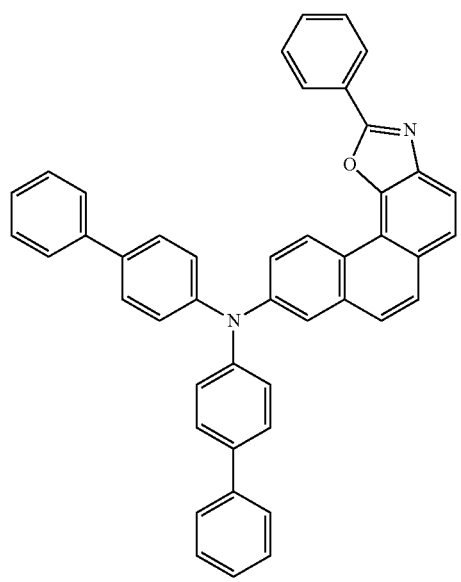
H1-4
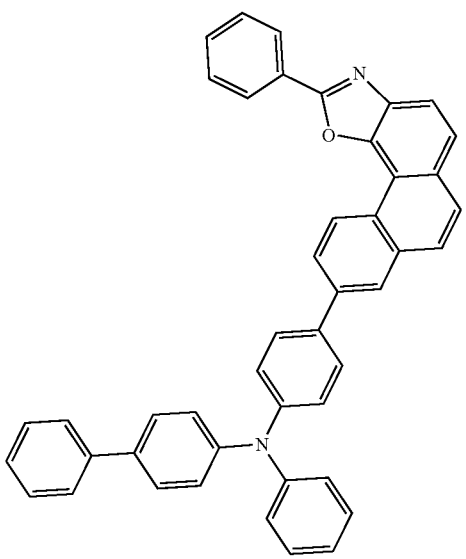
H1-5
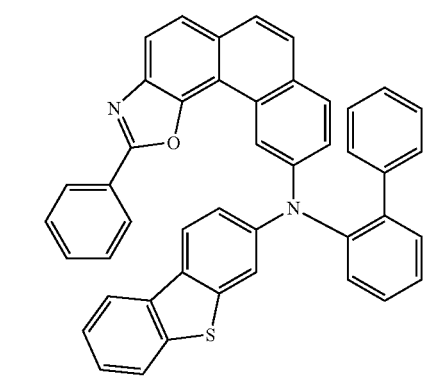
H1-6
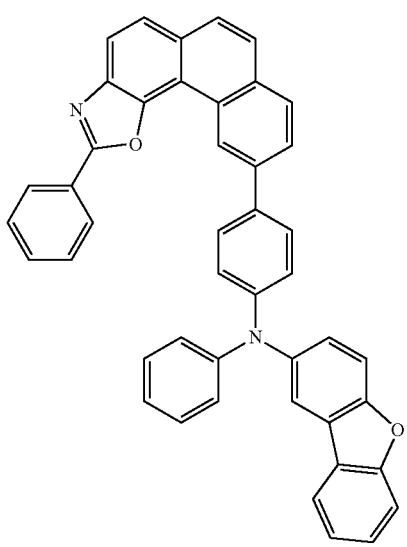
H1-7
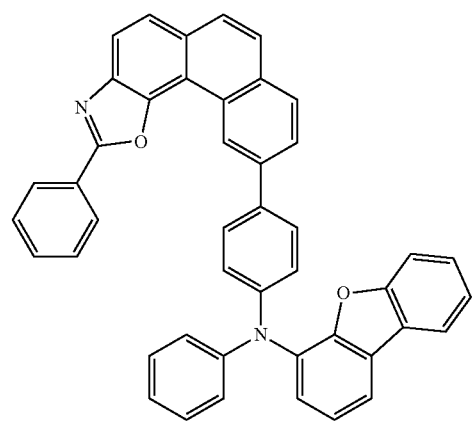
H1-8
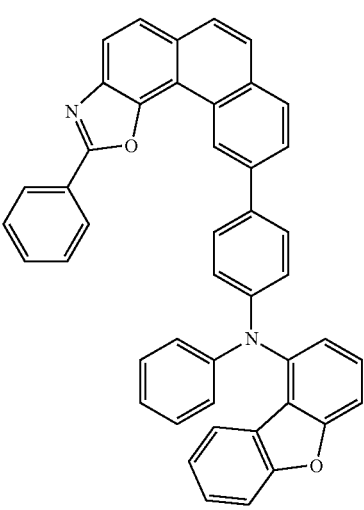

H1-9
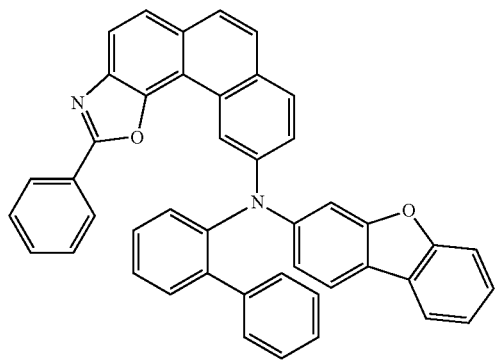
H1-10
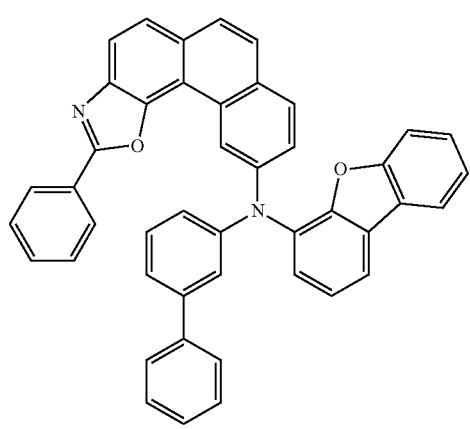
H1-11
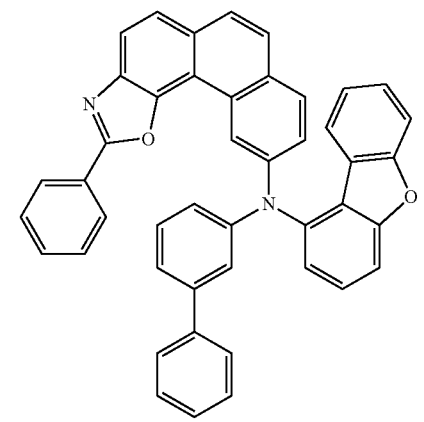
H1-12
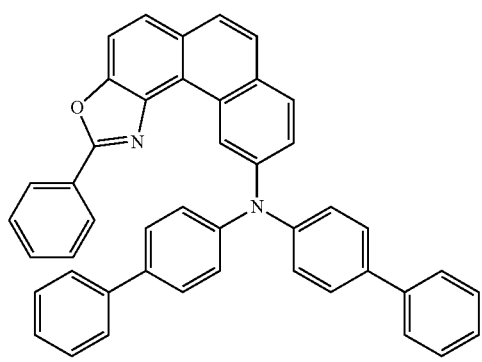
H1-13
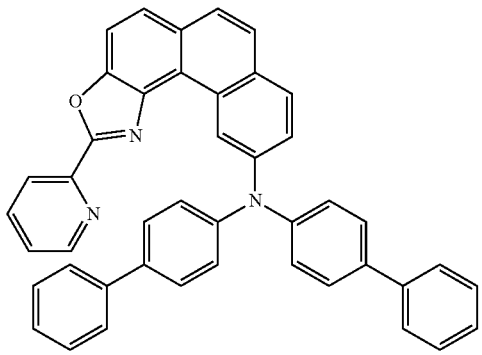
H1-14
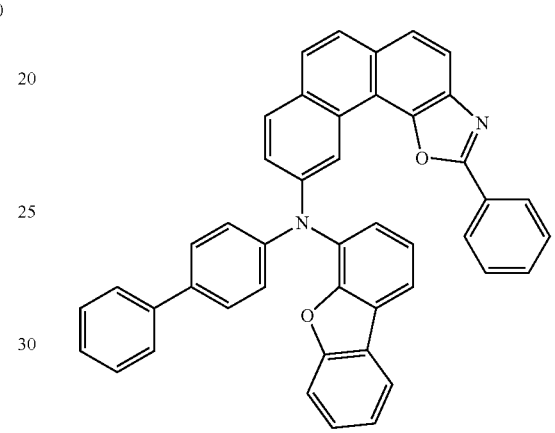
H1-15
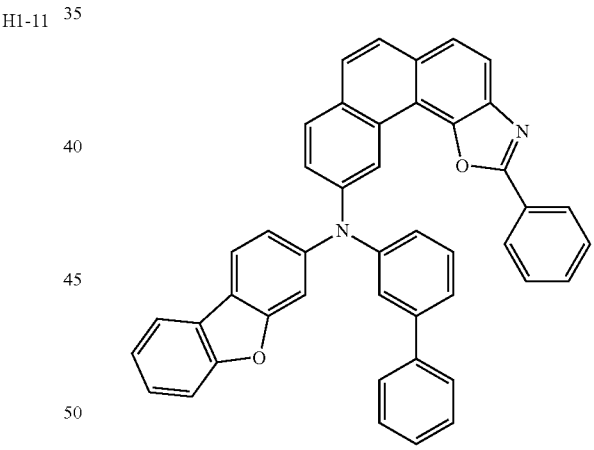
H1-16
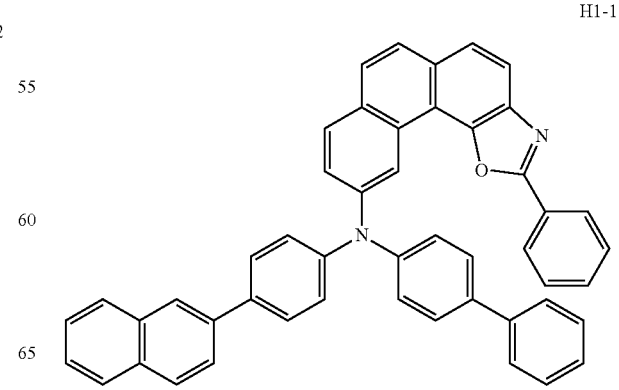

H1-17
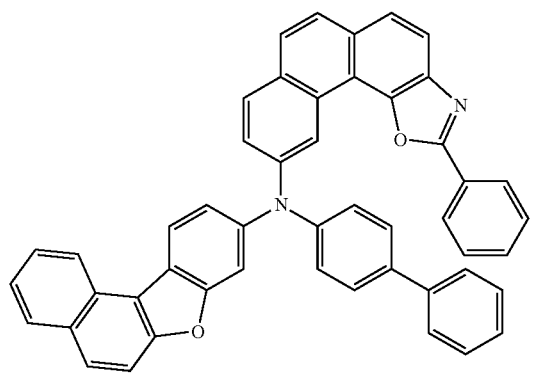
H1-18
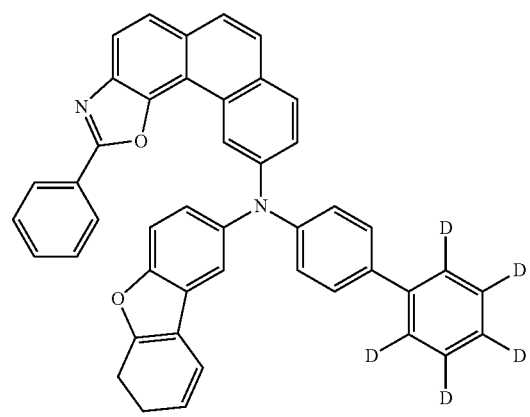
H1-19
H1-20
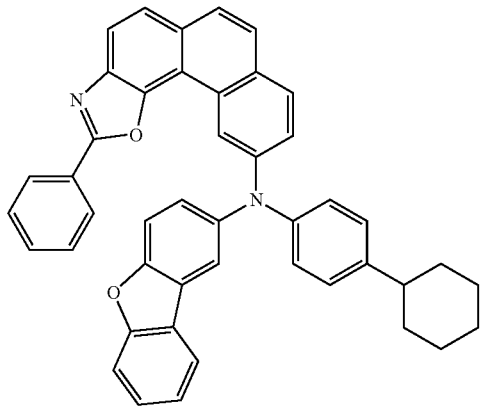
H1-21
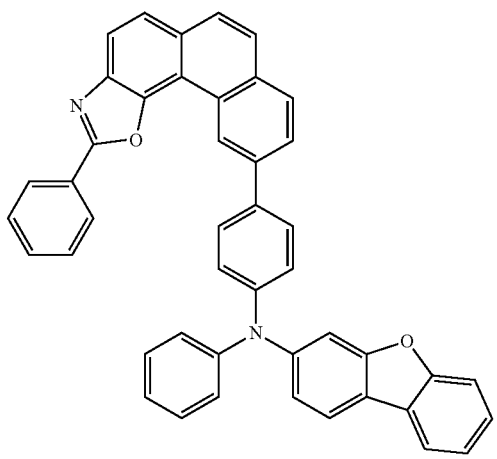
H1-22
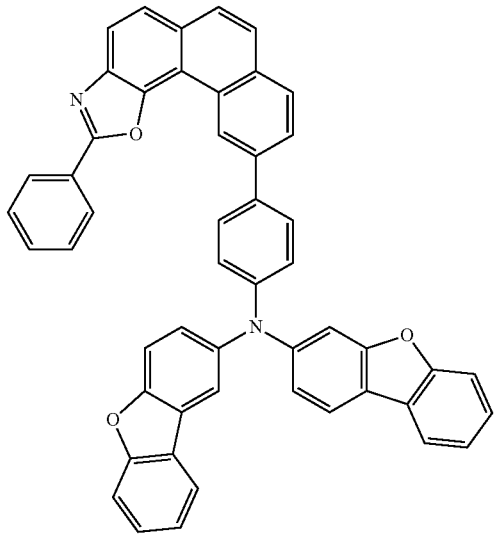

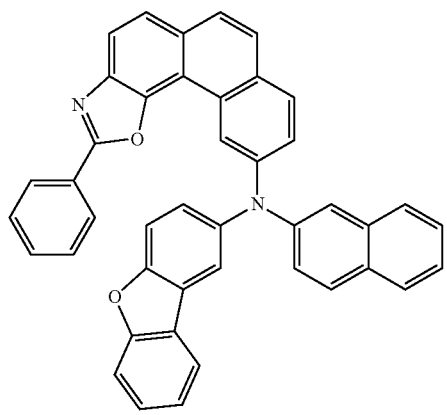
H1-23
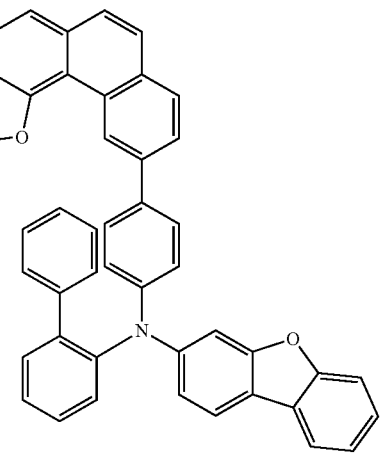
H1-26
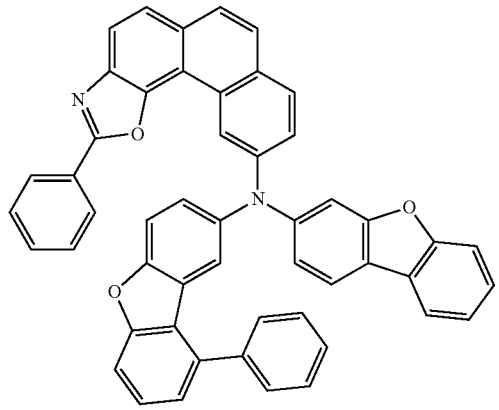
H1-24
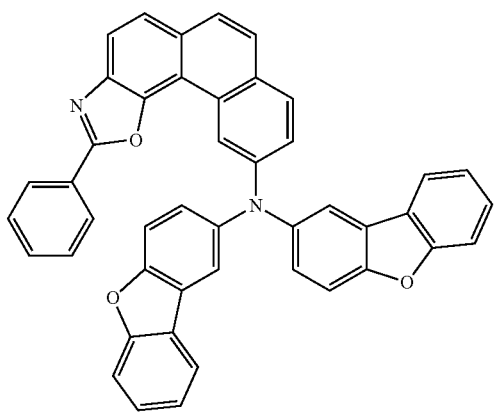
H1-27
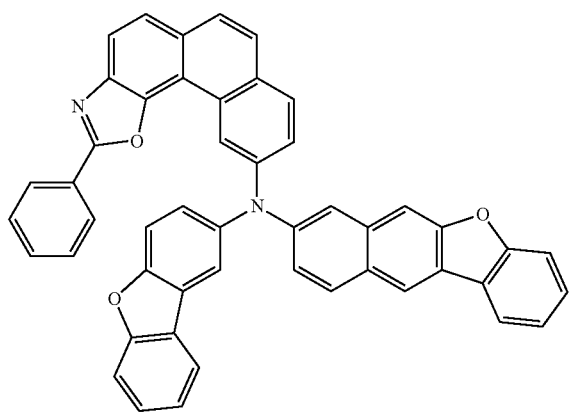
H1-25
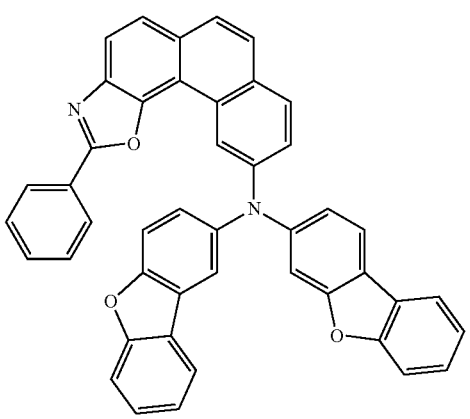
H1-28

-continued
H1-29
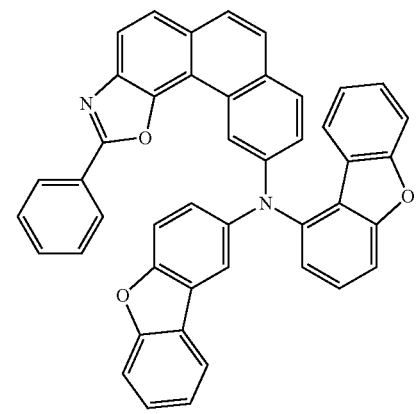
H1-30
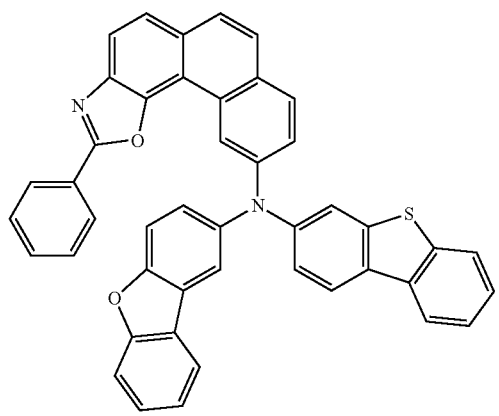
H1-31
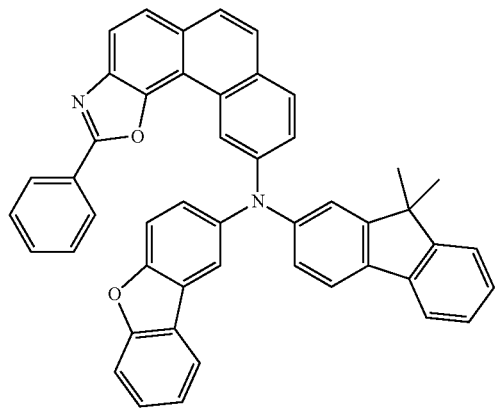
H1-32
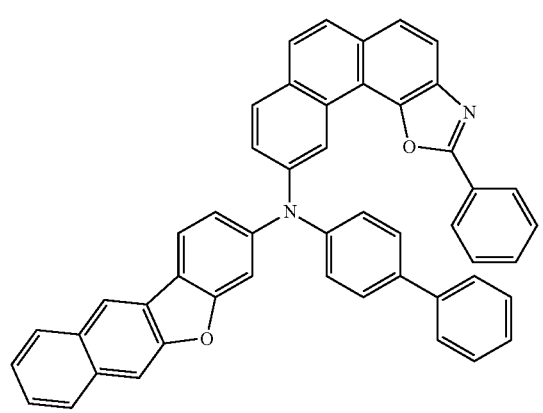
H1-33
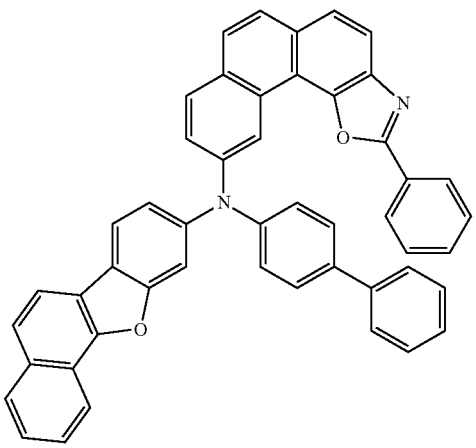
H1-34
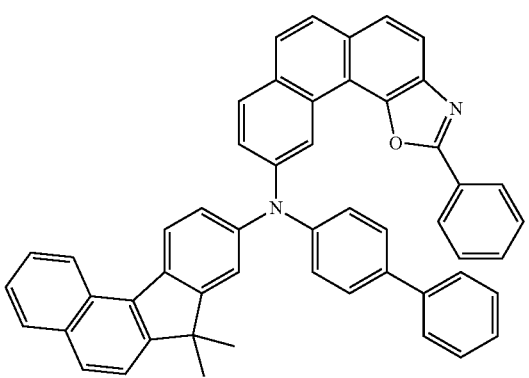
H1-35
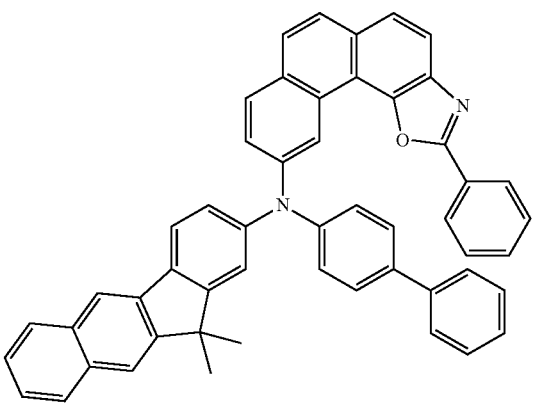
H1-36
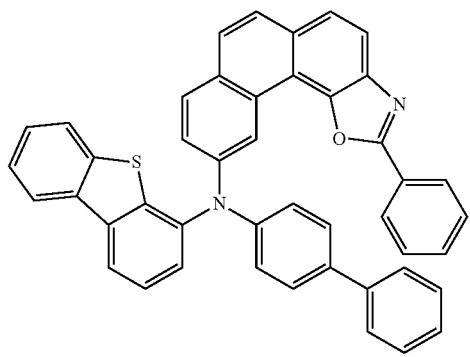

H1-37
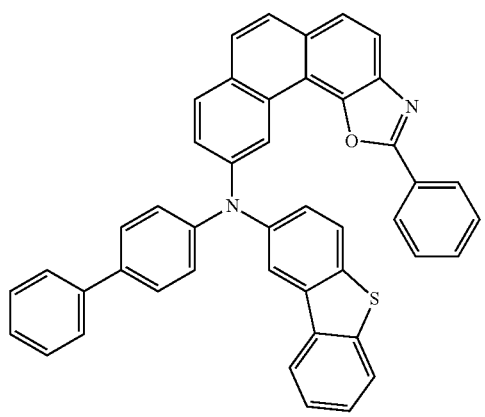
H1-38
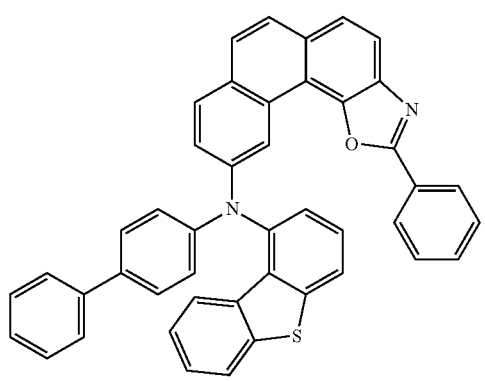
H1-39
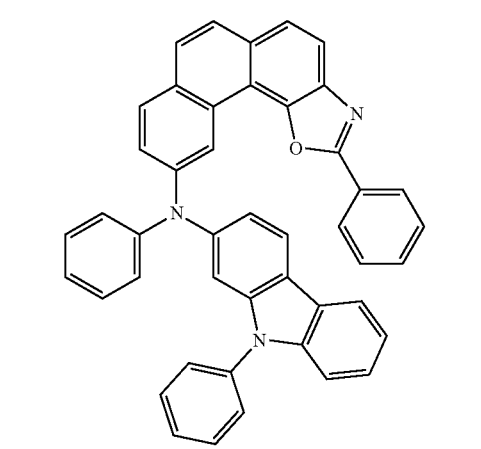
H1-40
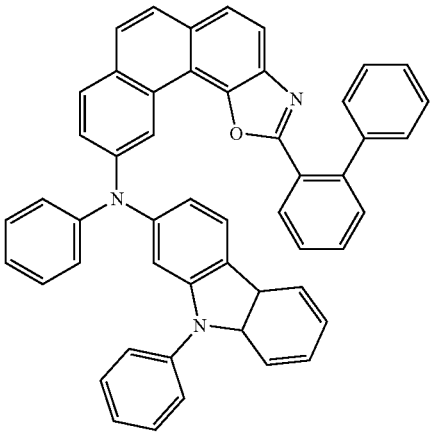
H1-41
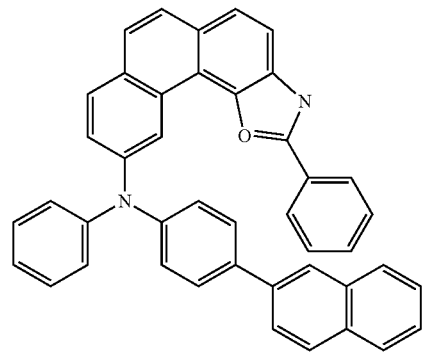
H1-42
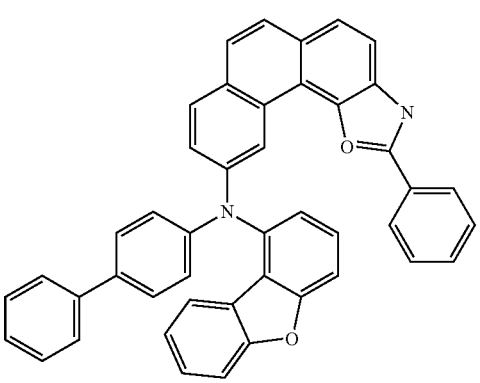
H1-43
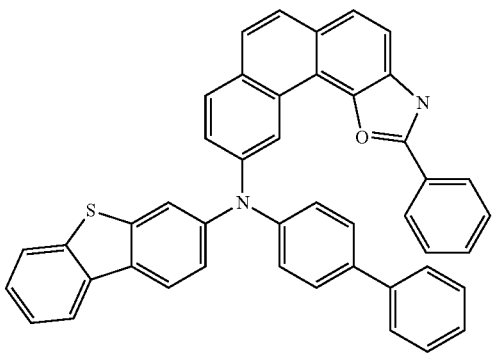

H1-44
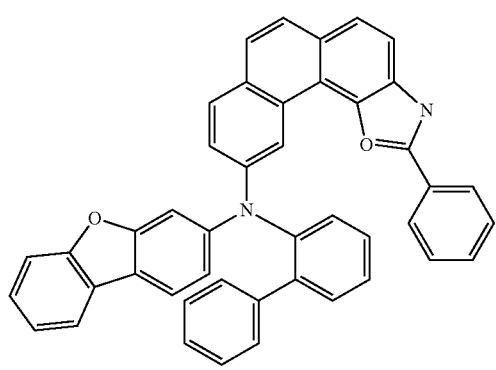
H1-45
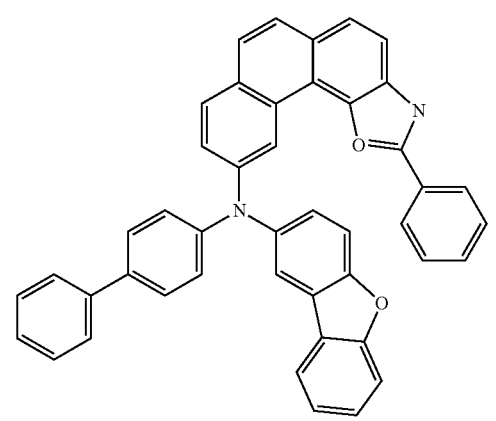
H1-46
H1-47
H1-48
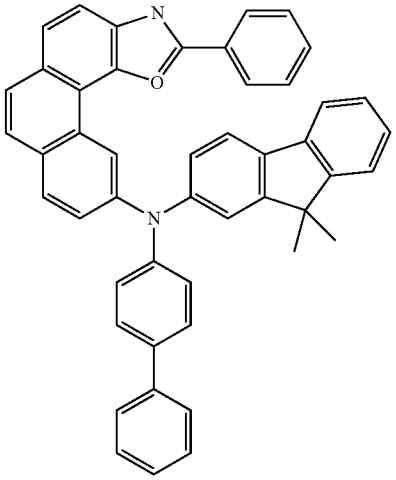
H1-49
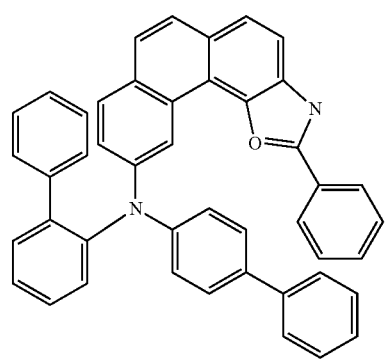
H1-50
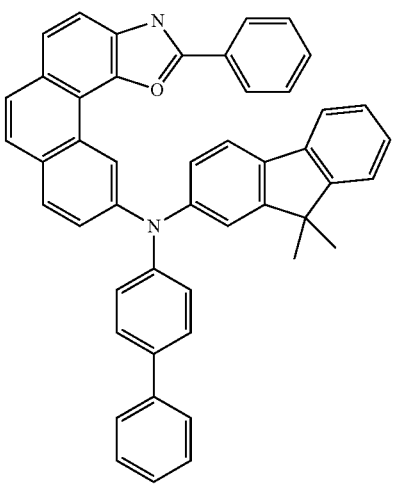

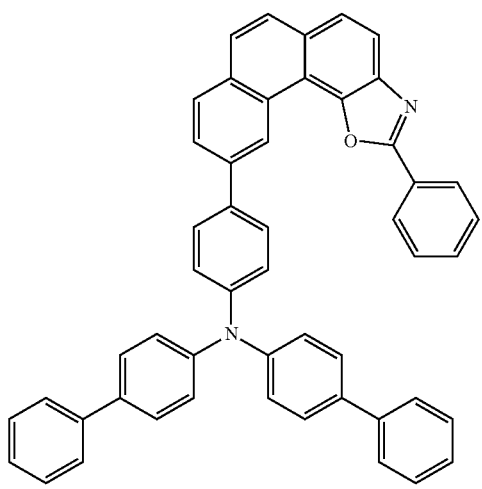
H1-51
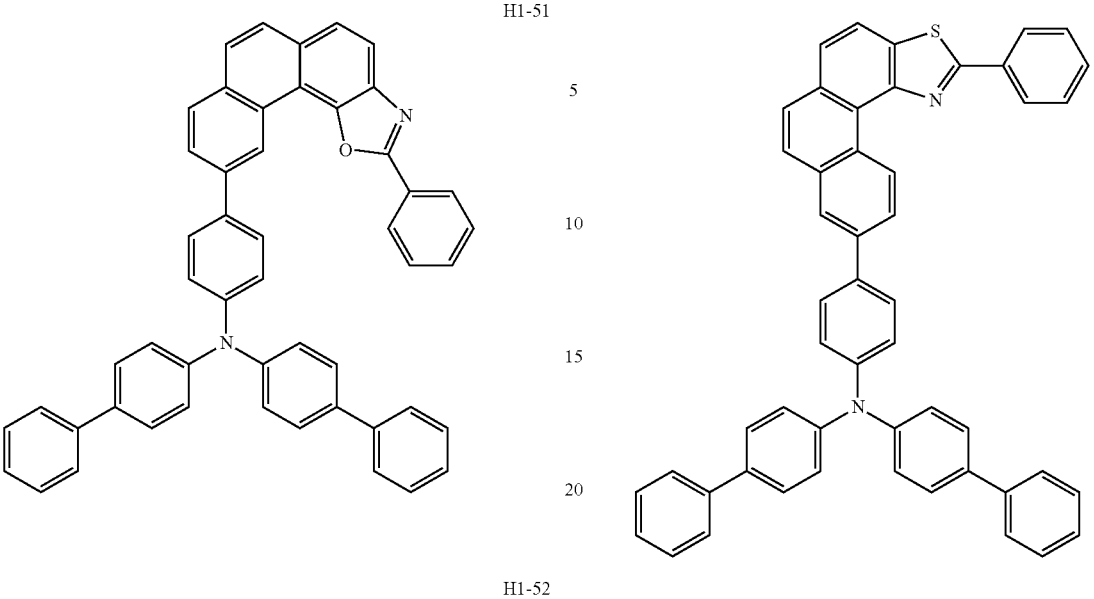
H1-54
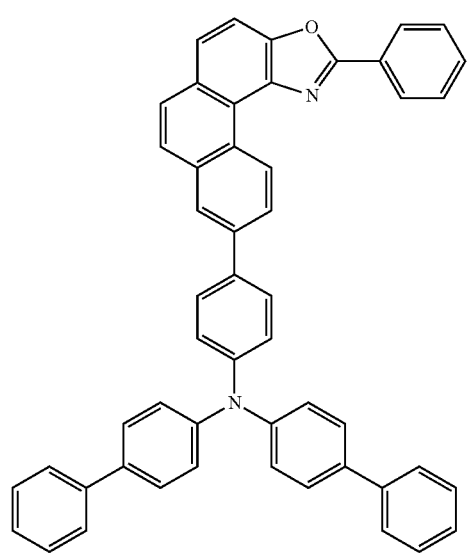
H1-52
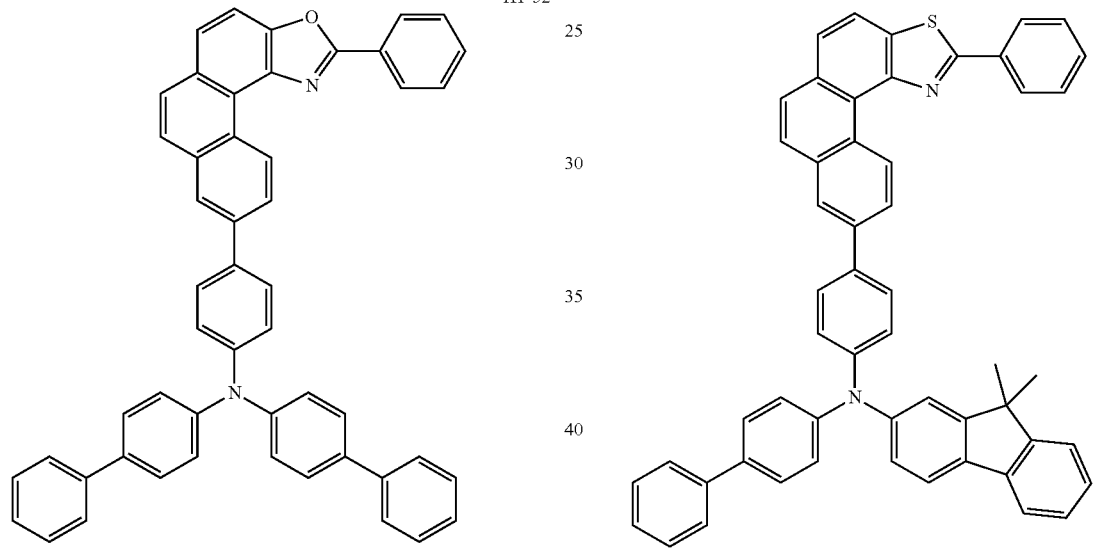
H1-55
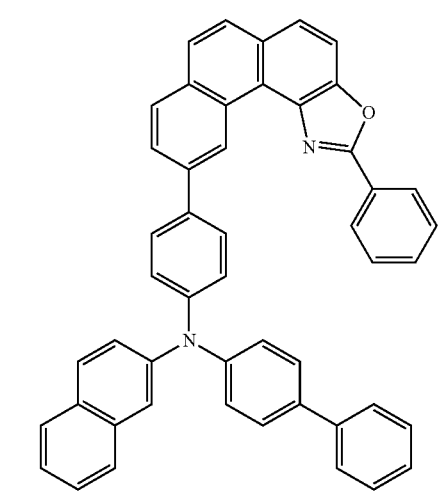
H1-53
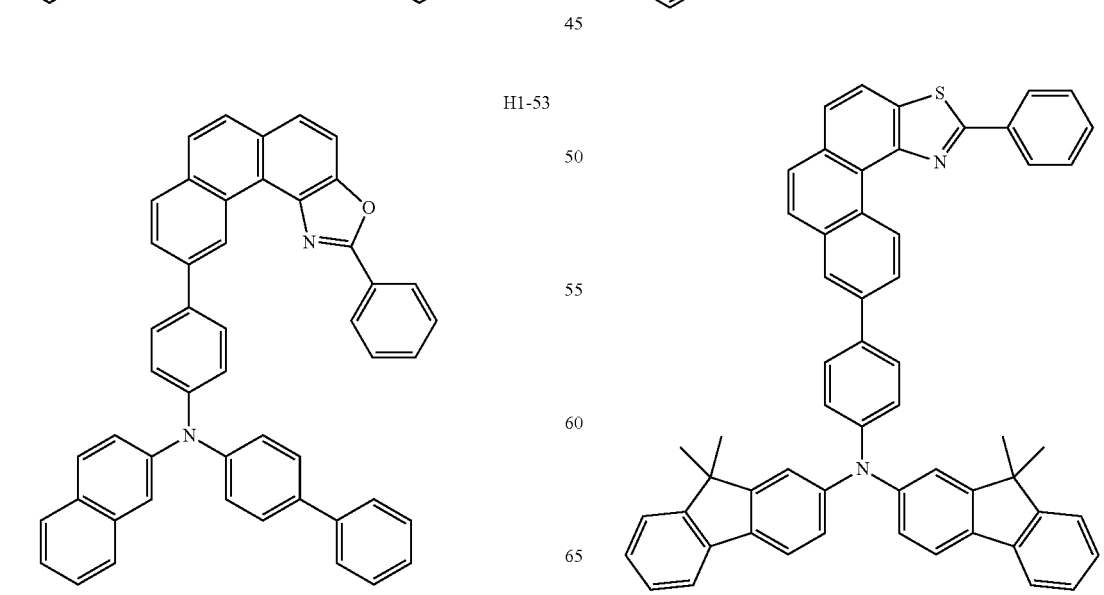
H1-56

H1-57
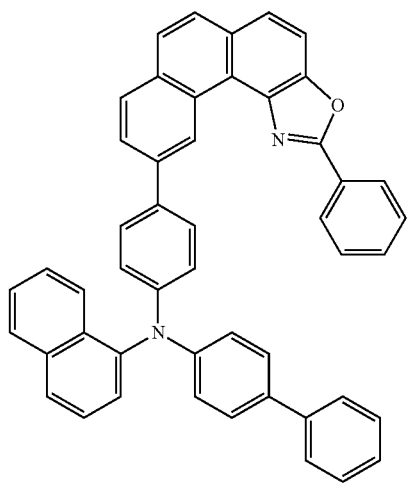
H1-58
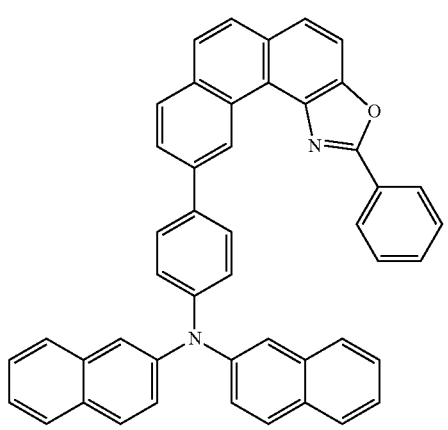
H1-59
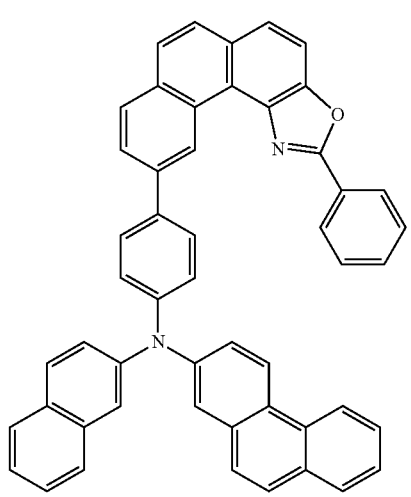
H1-60
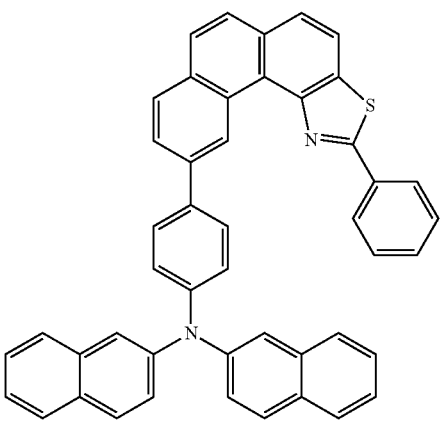
H1-61
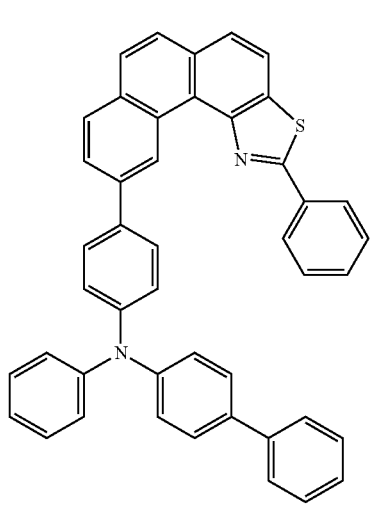
H1-62
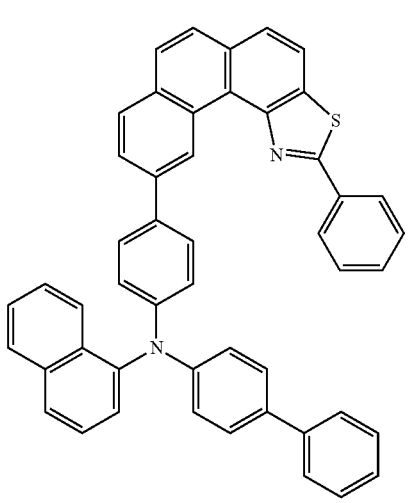

H1-63
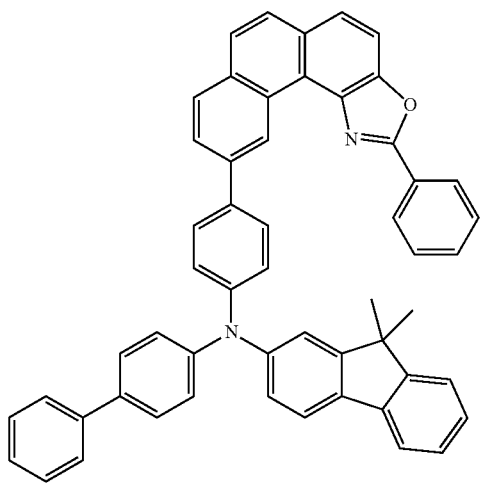
H1-64
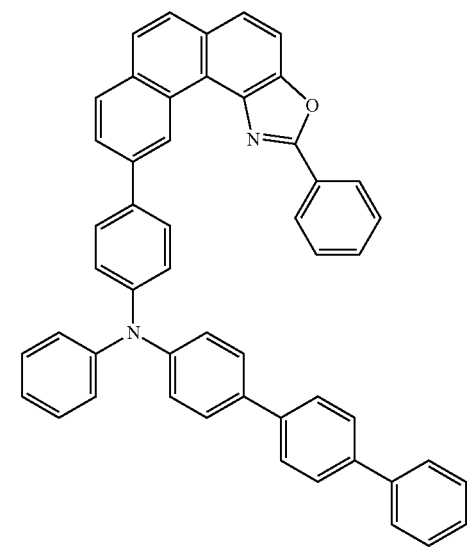
H1-66
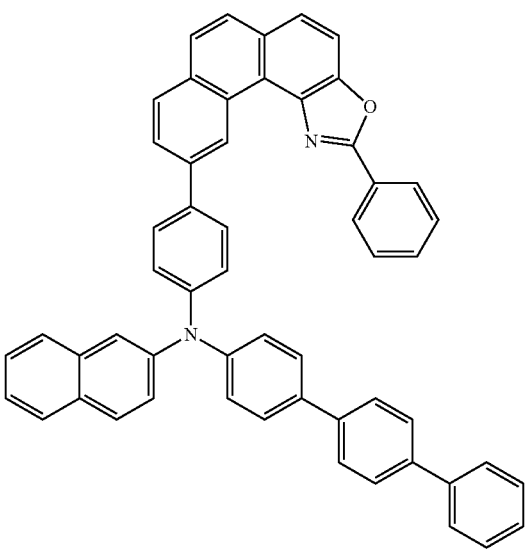
H1-67
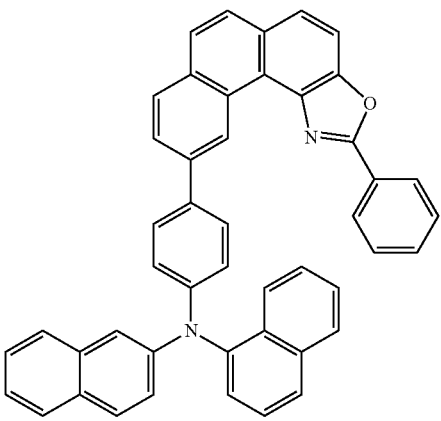
H1-68
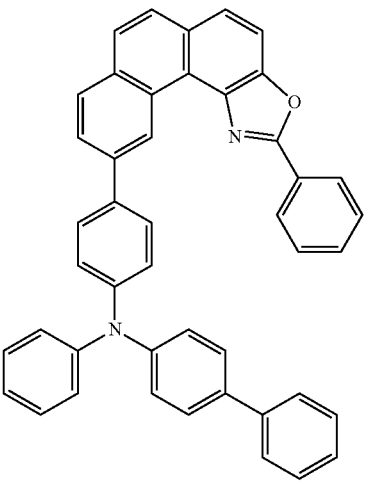

H1-69
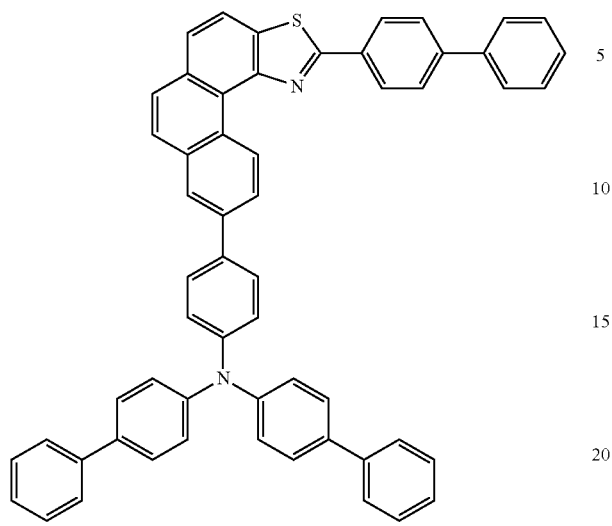
H1-70
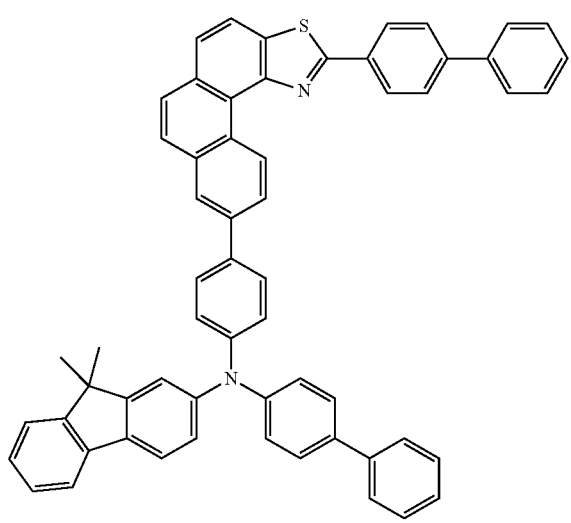
H1-71
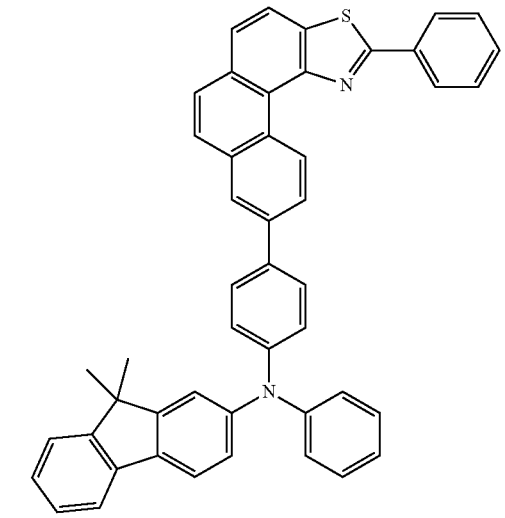
H1-72
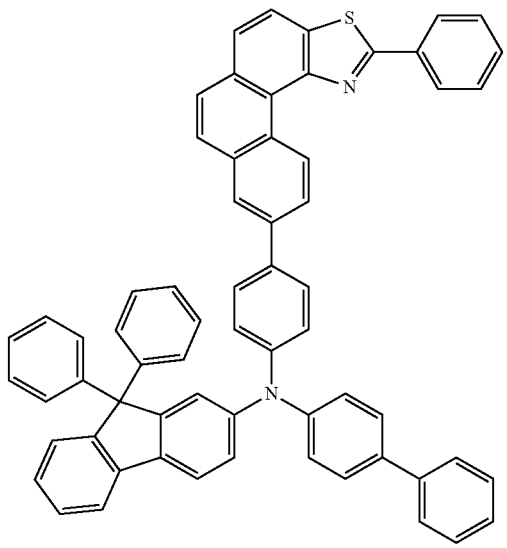
H1-73
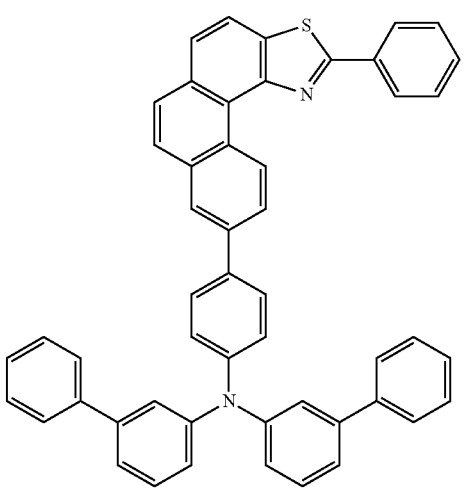
H1-74
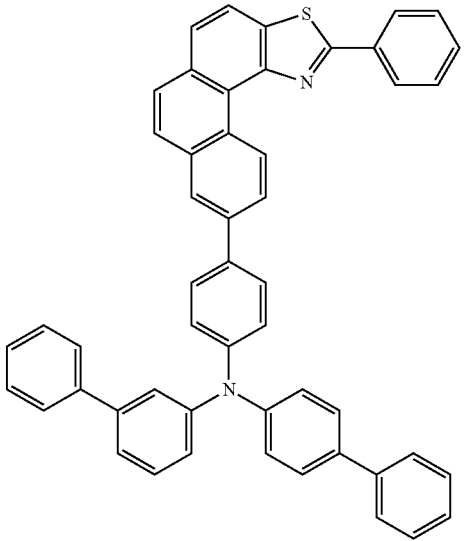

-continued
H1-75
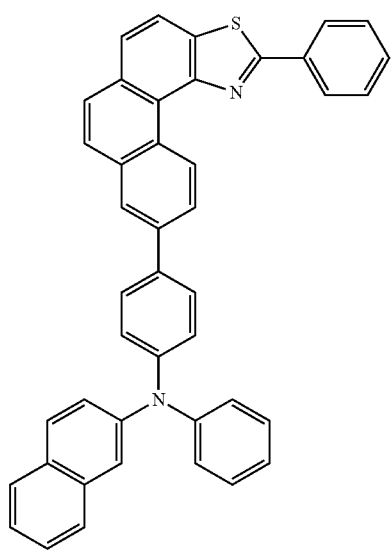
H1-76
H1-77
-continued
H1-78
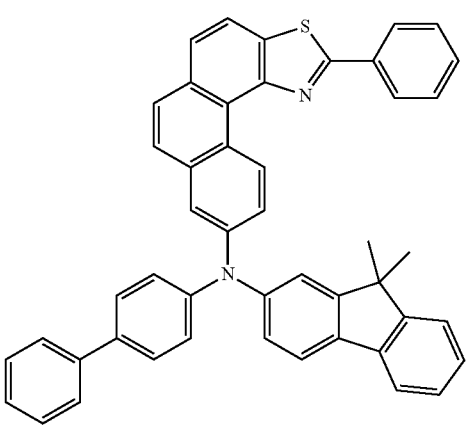
H1-79
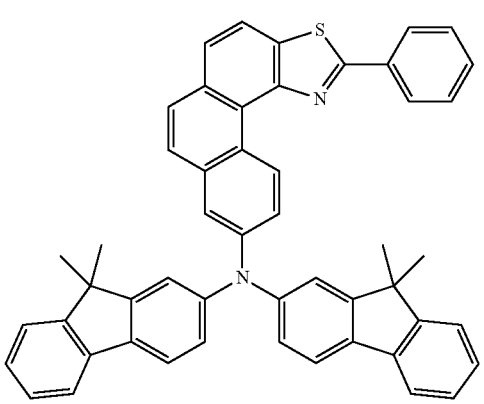
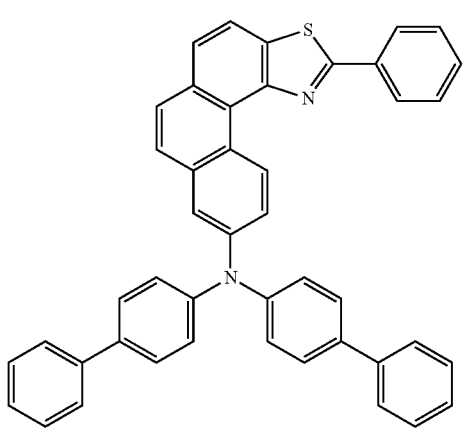
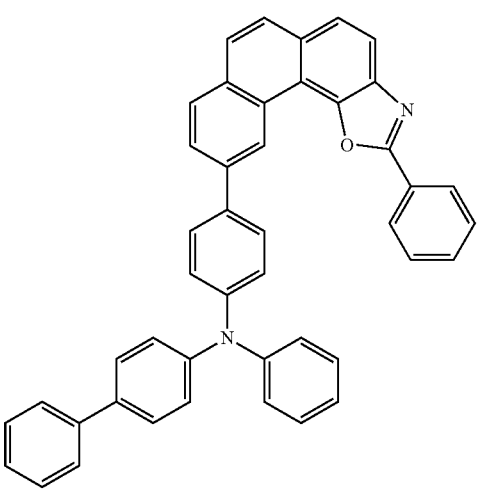
H1-80

-continued
H1-81
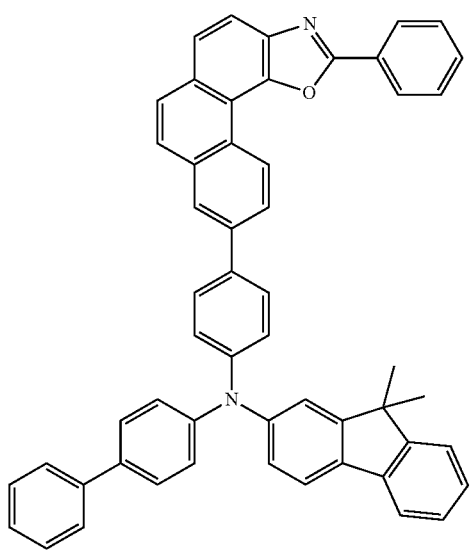
H1-82
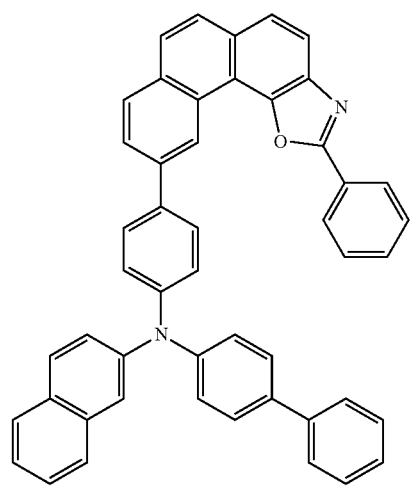
H1-83
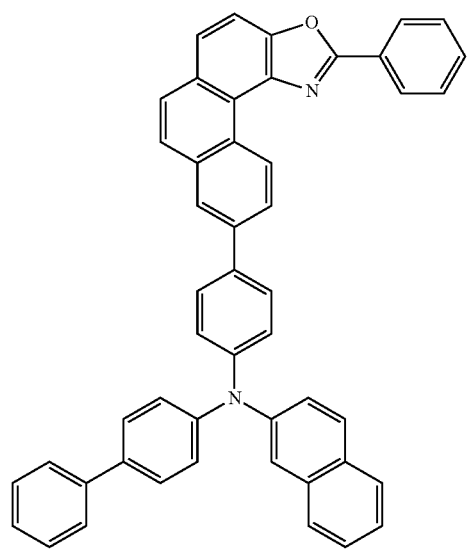
-continued
H1-84
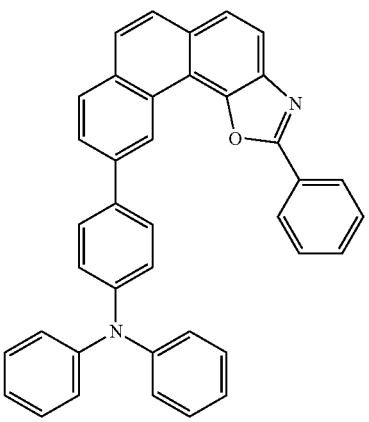
H1-85
H1-86
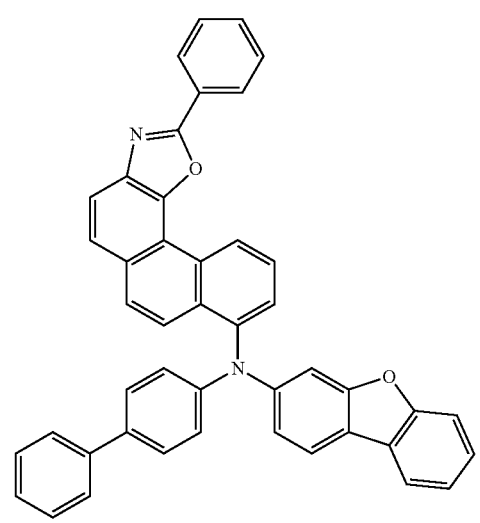

H1-87
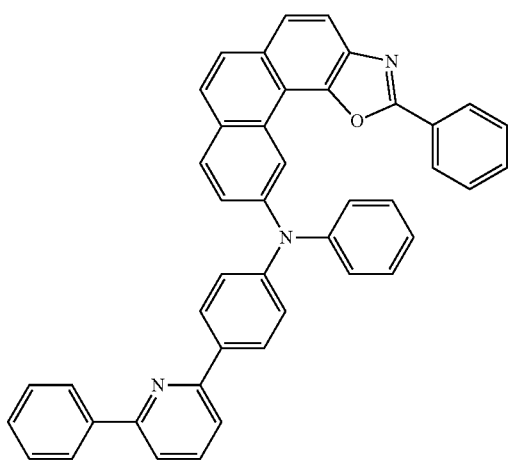
H1-90
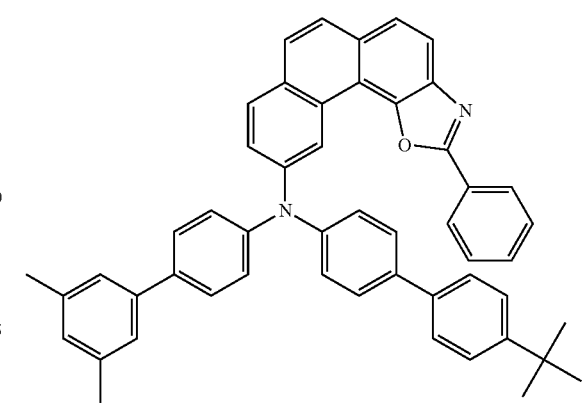
H1-88
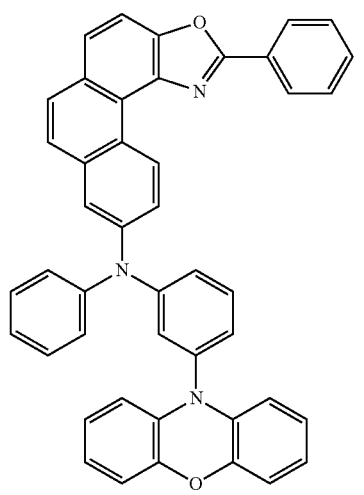
H1-91
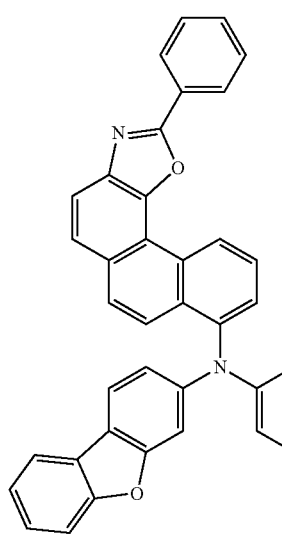
H1-89
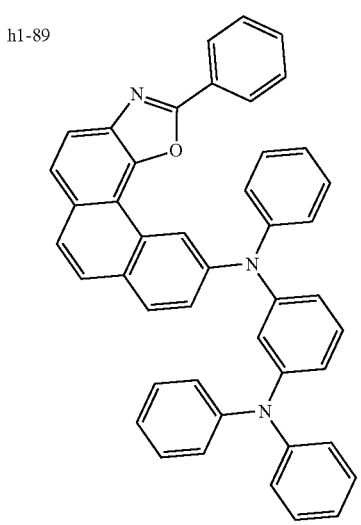
H1-92
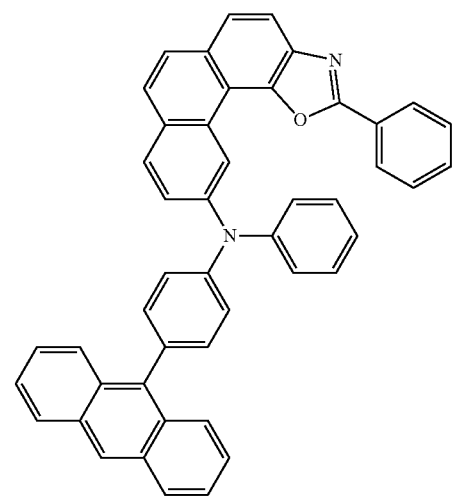

H1-93
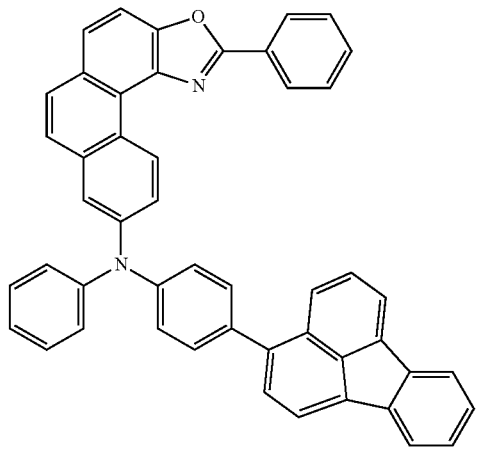
H1-96
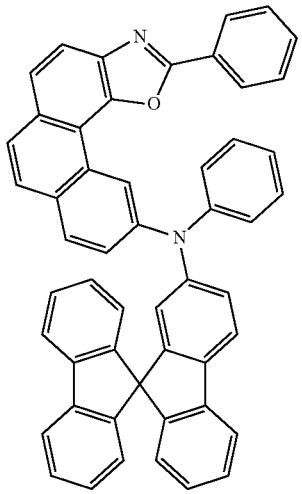
H1-94
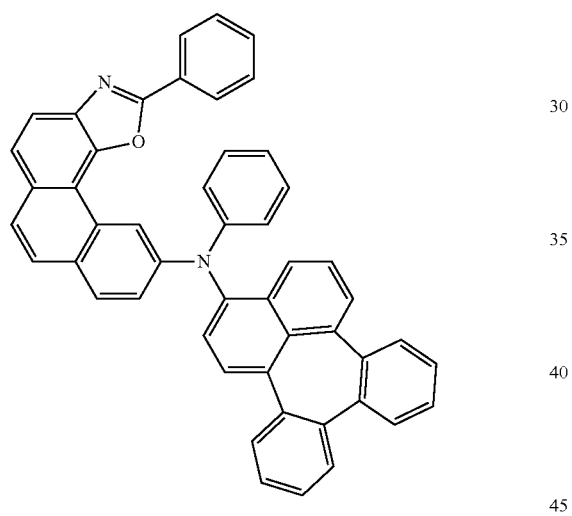
H1-95
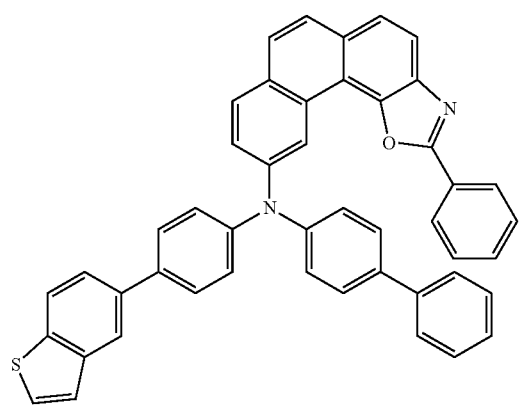
H1-97
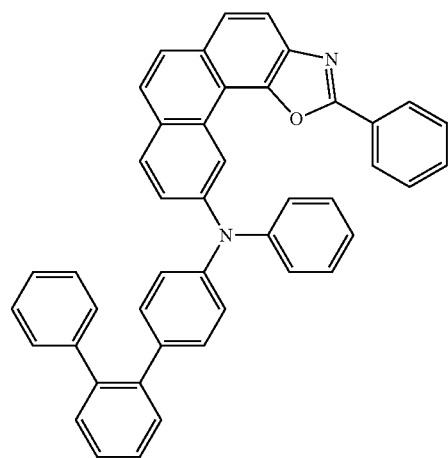

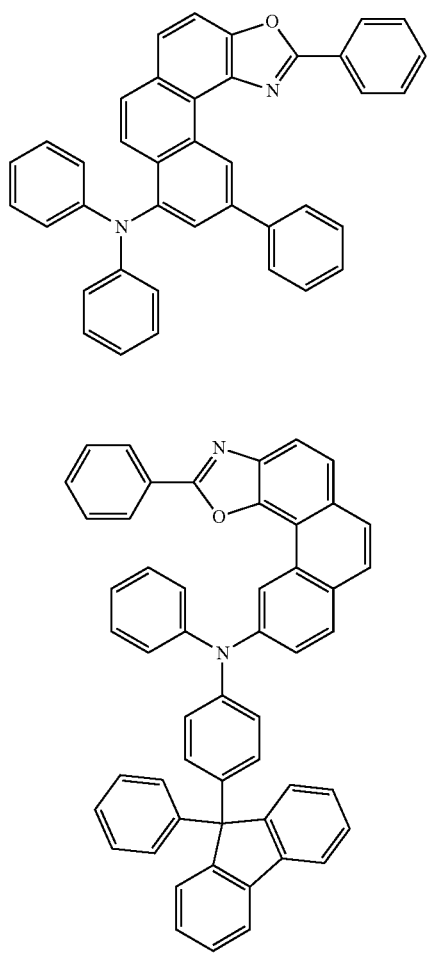
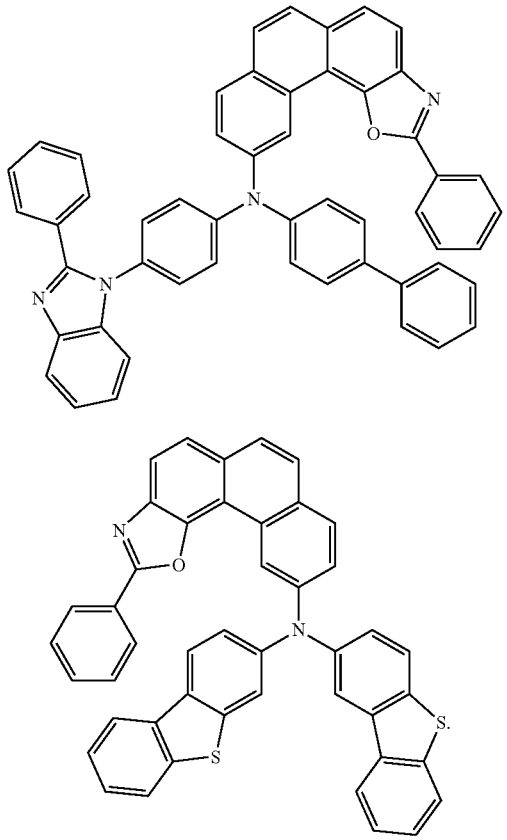
9. An organic electroluminescent device comprising the organic electroluminescent compound according to claim 1.
* * * * *